US012257090B2

(12) United States Patent
Altunbas

(10) Patent No.: US 12,257,090 B2
(45) Date of Patent: Mar. 25, 2025

(54) SCANNER UTILIZING BEAM COMPUTED TOMOGRAPHY AND ANTISCATTER GRID

(71) Applicant: The Regents of the University of Colorado, Denver, CO (US)

(72) Inventor: Cem Altunbas, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 203 days.

(21) Appl. No.: 18/151,363

(22) Filed: Jan. 6, 2023

(65) Prior Publication Data
US 2023/0225685 A1    Jul. 20, 2023

Related U.S. Application Data

(63) Continuation-in-part of application No. 17/572,718, filed on Jan. 11, 2022, now Pat. No. 11,723,612,
(Continued)

(51) Int. Cl.
*A61B 6/42* (2024.01)
*A61B 6/40* (2024.01)
(Continued)

(52) U.S. Cl.
CPC .......... *A61B 6/4291* (2013.01); *A61B 6/4035* (2013.01); *A61B 6/4216* (2013.01);
(Continued)

(58) Field of Classification Search
CPC ... A61B 6/4291; A61B 6/4035; A61B 6/4216; A61B 6/4283; A61B 6/032;
(Continued)

(56) References Cited

U.S. PATENT DOCUMENTS

| 4,866,744 A | 9/1989 | Yoshida |
| 5,712,483 A | 1/1998 | Boone et al. |

(Continued)

FOREIGN PATENT DOCUMENTS

| WO | 2003/055393 A1 | 7/2003 |
| WO | 2005/058164 A1 | 6/2005 |

(Continued)

OTHER PUBLICATIONS

Altunbas, Cem et al., "A Unified Scatter Rejections And Correction Method For Cone Beam Computed Tomography," Medical Physics, vol. 48, No. 3, pp. 1211-1225, Mar. 2021.

(Continued)

*Primary Examiner* — Kiho Kim

(57) ABSTRACT

A portable computed tomography (CT) system includes an O-shaped gantry defining an opening, an x-ray source operably coupled to the O-shaped gantry, and a flat panel detector (FPD) coupled to the O-shaped gantry and having a two-dimensional anti-scatter grid (2D ASG) coupled to a side of the FPD facing the opening. With the O-shaped gantry having the FPD, the object may be imaged in a first field of view (FOV) with the detector arranged in a centered geometry. Then, the detector may be arranged in an offset geometry, through-holes of the ASG may be aligned with x-ray emission paths of the x-ray source, and the object may be imaged in a second FOV with the detector arranged in the offset geometry.

8 Claims, 52 Drawing Sheets

Related U.S. Application Data which is a continuation of application No. 16/606,141, filed as application No. PCT/US2018/027660 on Apr. 13, 2018, now Pat. No. 11,224,389.

(60) Provisional application No. 62/576,265, filed on Oct. 24, 2017, provisional application No. 62/573,021, filed on Oct. 16, 2017, provisional application No. 62/486,113, filed on Apr. 17, 2017.

(51) Int. Cl.
 *G01T 1/20* (2006.01)
 *G01T 7/00* (2006.01)

(52) U.S. Cl.
 CPC .......... *A61B 6/4283* (2013.01); *G01T 1/2002* (2013.01); *G01T 1/2006* (2013.01); *G01T 7/00* (2013.01)

(58) Field of Classification Search
 CPC ... A61B 6/4085; A61B 6/4233; A61B 6/4405; G01T 1/2002; G01T 1/2006; G01T 7/00; G01T 1/2985; G01T 1/20188
 See application file for complete search history.

(56) References Cited

U.S. PATENT DOCUMENTS

| | | |
|---|---|---|
| 5,864,146 A | 1/1999 | Karellas |
| 2002/0003863 A1 | 1/2002 | Ohkoda |
| 2004/0232342 A1 | 11/2004 | Aykac et al. |
| 2006/0023832 A1 | 2/2006 | Edic et al. |
| 2009/0304142 A1 | 12/2009 | Ruimi et al. |
| 2010/0127180 A1 | 5/2010 | Lifshitz et al. |
| 2011/0081004 A1 | 4/2011 | Harding et al. |
| 2011/0142316 A1 | 6/2011 | Wang et al. |
| 2011/0274246 A1 | 11/2011 | Maschke |
| 2012/0049074 A1 | 3/2012 | Luhta et al. |
| 2012/0132833 A1 | 5/2012 | Freund et al. |
| 2012/0132834 A1 | 5/2012 | Freund et al. |
| 2012/0257710 A1 | 10/2012 | Funk |
| 2012/0300898 A1 | 11/2012 | Kreisler et al. |
| 2014/0048713 A1 | 2/2014 | Liu et al. |
| 2014/0177789 A1 | 6/2014 | Baturin et al. |
| 2014/0321610 A1 | 10/2014 | Ueki et al. |
| 2015/0119704 A1 | 4/2015 | Roth et al. |
| 2016/0148375 A1 | 5/2016 | Oh et al. |
| 2016/0328836 A1 | 11/2016 | Hsieh |
| 2017/0097425 A1 | 4/2017 | Shedlock et al. |
| 2017/0203125 A1 | 7/2017 | Amato et al. |
| 2017/0209714 A1 | 7/2017 | Bennett et al. |
| 2017/0209715 A1 | 7/2017 | Ruebel et al. |
| 2017/0216632 A1 | 8/2017 | Lee et al. |
| 2017/0259084 A1 | 9/2017 | Bennett et al. |
| 2017/0259085 A1 | 9/2017 | Bennett et al. |
| 2017/0312253 A1 | 11/2017 | Wang et al. |
| 2018/0217734 A1 | 8/2018 | Koenig et al. |
| 2018/0271459 A1 | 9/2018 | Wang et al. |
| 2018/0360400 A1 | 12/2018 | Simon et al. |
| 2021/0045707 A1* | 2/2021 | Sosenko .................. A61B 6/06 |

FOREIGN PATENT DOCUMENTS

| | | | |
|---|---|---|---|
| WO | 2017/023105 A1 | 2/2017 | |
| WO | 2017/165487 A1 | 9/2017 | |
| WO | WO-2021108715 A1 * | 6/2021 | ............. A61B 6/027 |

OTHER PUBLICATIONS

International Application No. PCT/US2018/027660, International Search Report & Written Opinion, 11 pages, Jul. 9, 2018.

Radiological Imaging Technology, Inc., "RITG142," 1 page, 2021.

Rumboldt, Z. et al., "Review Of Portable CT With Assessment Of A Dedicated Head CT Scanner," Am J Nueroradiol, vol. 30, No. 9, pp. 1630-1636, Oct. 2009.

Tyrrell, Glenn C., "Phosphors And Scintillators In Radiation Imaging Detectors," Nuclear Instruments and Methods in Physics Research A, vol. 546, pp. 180-187, 2005

* cited by examiner

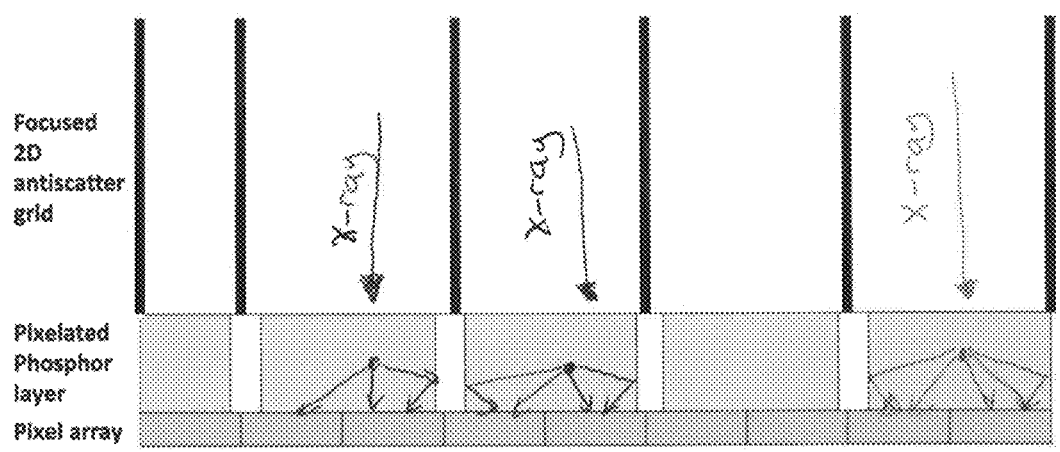
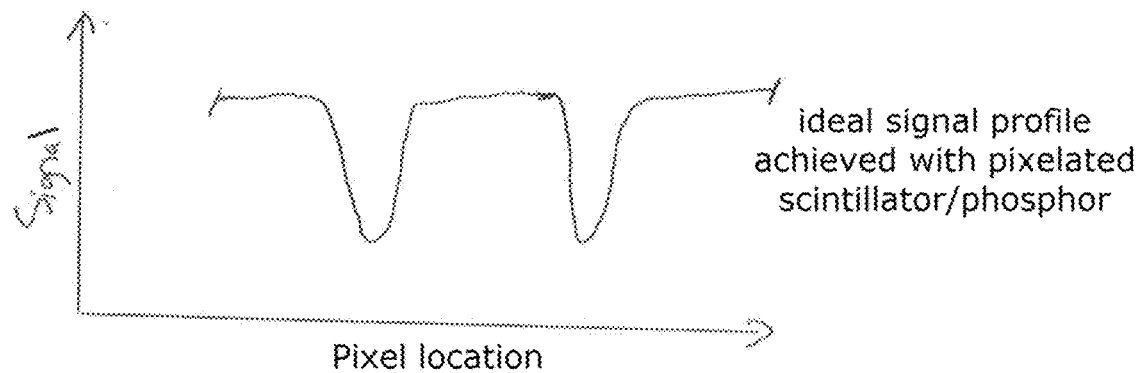
FIGURE 22

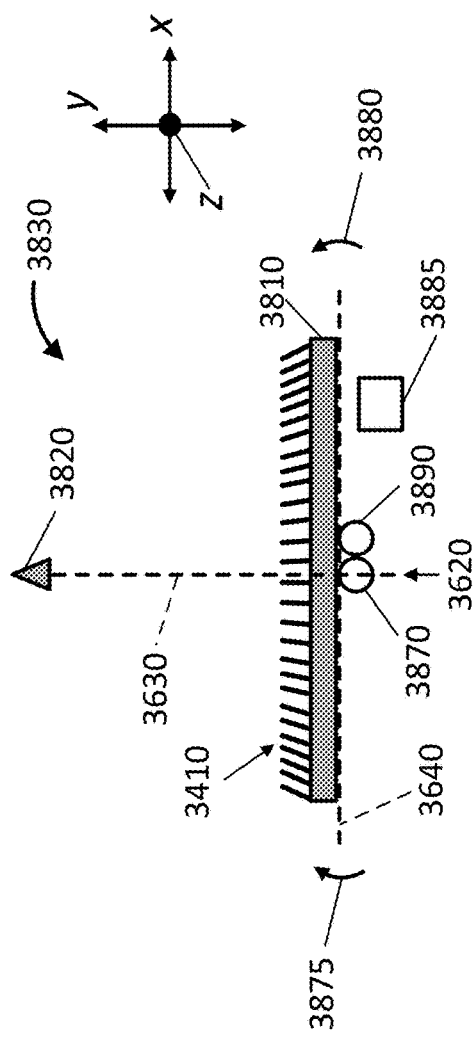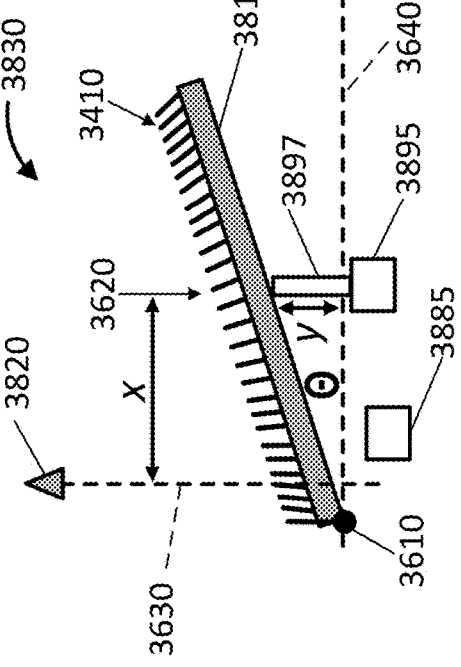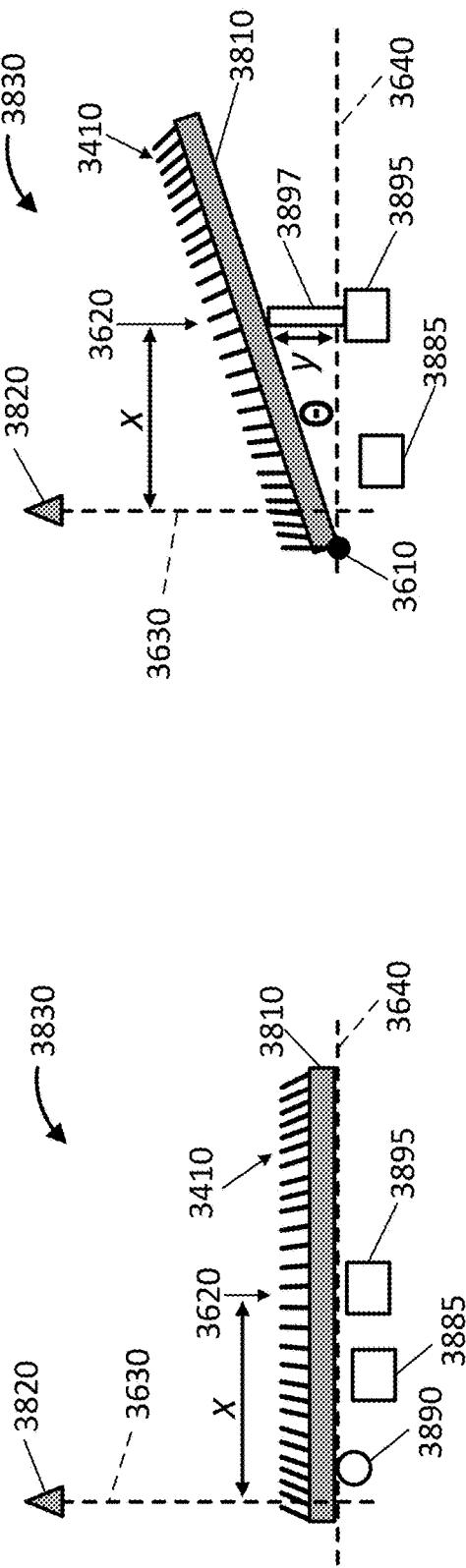
FIGURE 38B
FIGURE 38C
FIGURE 38D

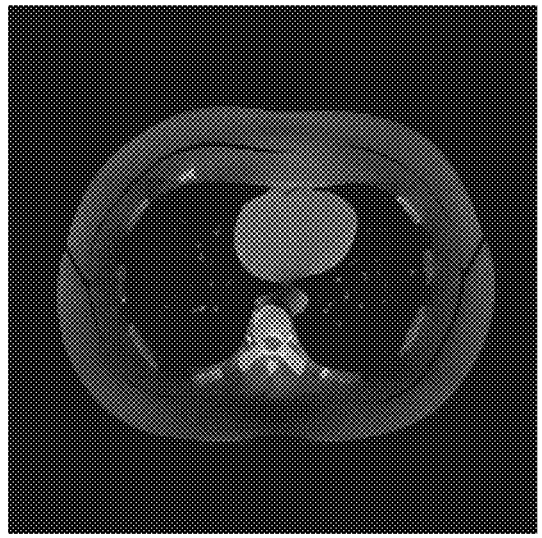 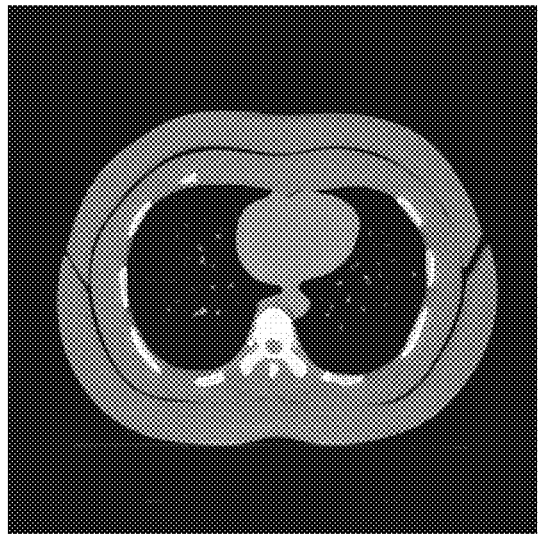
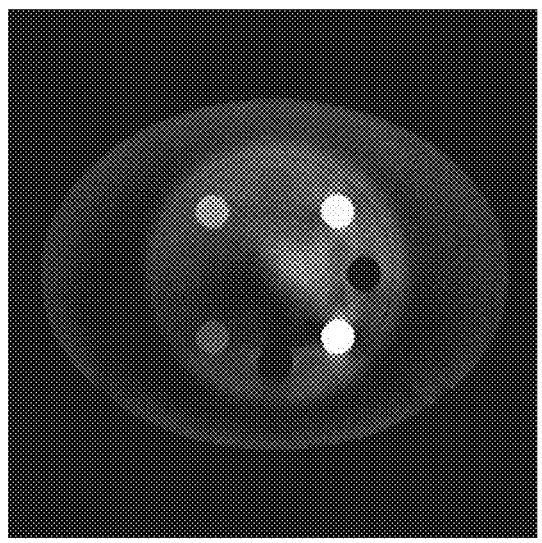 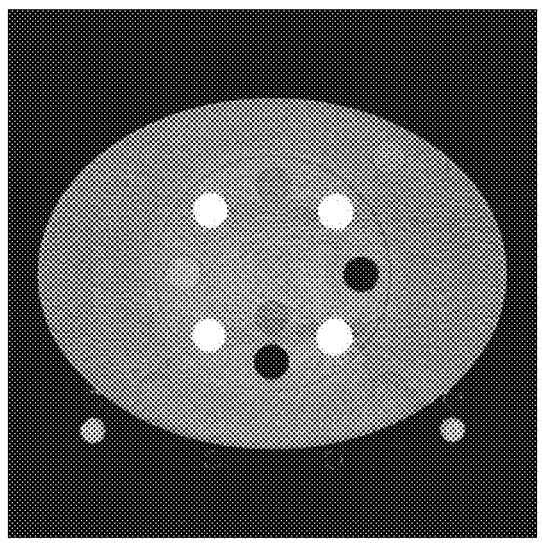
FIGURE 41A  FIGURE 41B

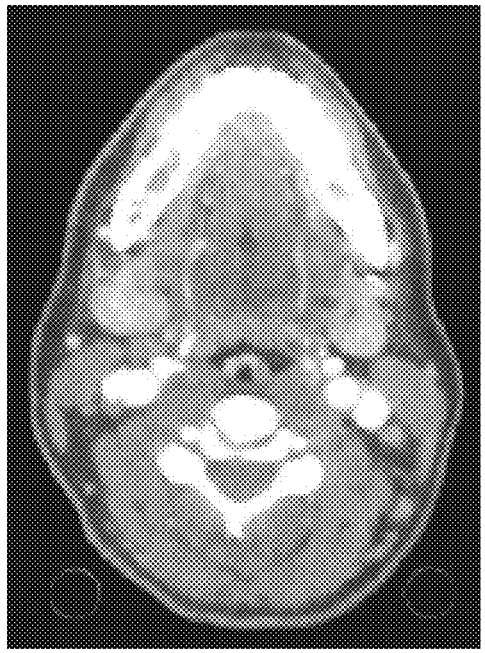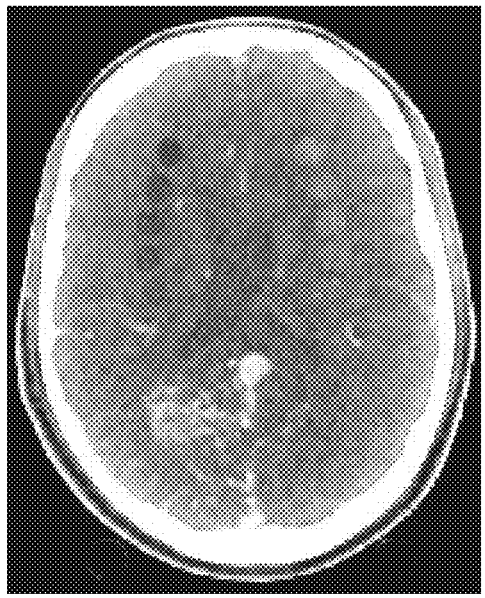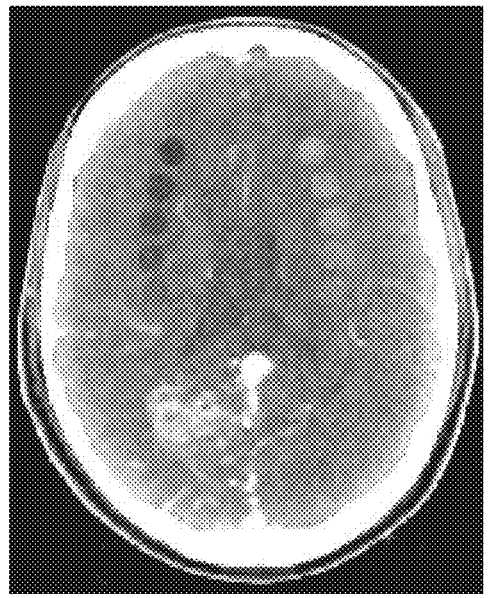
FIGURE 42A                    FIGURE 42B

SCANNER UTILIZING BEAM COMPUTED TOMOGRAPHY AND ANTISCATTER GRID

CROSS-REFERENCE TO RELATED APPLICATIONS

This application is a continuation-in-part of U.S. patent application Ser. No. 17/572,718 filed Jan. 11, 2022; which is a continuation of U.S. patent application Ser. No. 16/606,141 filed Oct. 17, 2019, and issued as U.S. Pat. No. 11,224,389 on Jan. 18, 2022; which is a national stage of International Patent Application No. PCT/US2018/027660 filed Apr. 13, 2018; which claims the benefit of and priority to U.S. Provisional Patent Application Nos. 62/486,113 filed Apr. 17, 2017, 62/573,021 filed Oct. 16, 2017, and 62/576,265 filed Oct. 24, 2017; the entire contents of each of which is incorporated herein by reference herein.

STATEMENT OF GOVERNMENTAL SUPPORT

This invention was made with government support under grant numbers R21CA198462 and R01CA245270 awarded by the National Cancer Institute of the National Institutes of Health. The government has certain rights in the invention.

FIELD OF THE INVENTION

The present invention relates generally to X-ray detectors and more particularly to a system and a method for integrating an antiscatter grid with scintillators to significantly enhance the performance of a flat panel X-ray detector in portable computed tomography (CT) scanners. In particular, the performance of a flat panel X-ray detector in a portable CT scanner may be enhanced by integrating the flat panel detector with 2D antiscatter grid.

BACKGROUND OF THE INVENTION

The purpose of a 2D antiscatter grid is to stop scattered x-rays reaching a flat panel detector, and improve the image quality. However, the design of the 2D antiscatter grid and the method to combine it with the subcomponents of the x-ray detector is important to maximize the image quality. Moreover, a fraction of scattered x-rays can still pass through a 2D grid, and reach the detector. As a result, the image quality can be deteriorated. Although, 2D grid's height (or grid ratio) can be increased to reduce the transmission of scatter, such a grid design will lead to other technical and practical challenges, which deteriorates image quality. Therefore, a correction algorithm is required to correct the residual scatter intensity transmitted through the 2D grid. What is needed is a 2D grid and methods that improve image quality and performance of flat panel X-ray detector systems.

Additionally, a new function for the 2D grid is disclosed in this invention; a 2D grid generates high and low fluence regions in the x-ray detector due to the footprint of the 2D grid on the x-ray detector. This modulated fluence pattern can be used to solve the "pulse pile-up" problem in photon counting x-ray detectors.

Cone beam computed tomography (CBCT) is a compact 3D imaging technology that has been utilized in a broad set of medical and industrial imaging applications including dentistry, orthopedics, and interventional radiology, among others. While CBCT provides cost efficient volumetric imaging capability, its main drawback is its relatively poor image quality due to a large volume of x-ray illumination and scattered radiation. In recent years, antiscatter grids have been a focus of research to reduce X-ray scattering in CBCT imaging. However, the benefits offered by commercially-available antiscatter grids do not sufficiently improve quality of soft tissue images for quantitative measurement. In clinical applications, poor soft tissue visualization and reduced quantitative accuracy in CBCT impacts clinical decision-making. There exists a need to improve upon the antiscatter grid technology to increase CT number accuracy and contrast sensitivity in soft tissue imaging.

SUMMARY

One aspect of the disclosure provides a method of operating an x-ray imaging system. The method may include the step of arranging an x-ray source and a detector having an antiscatter grid (ASG) in a centered geometry wherein through-holes of the ASG are aligned with x-rays emission paths of the x-ray source. The method may include the step of positioning an object between the detector and the x-ray source. The method may include the step of imaging the object in a first field of view (FOV) with the detector and the x-ray source arranged in the centered geometry. The method may include the step of arranging the x-ray source and the detector in an offset geometry wherein the through-holes of the ASG are at least partially unaligned with the x-rays emission paths of the x-ray source. The method may include the step of moving the detector in the offset geometry to realign the through-holes of the ASG with the x-ray emission paths of the x-ray source. The method may also include the step of imaging the object in at least a second FOV with the detector and the x-ray source arranged in the offset geometry.

Another aspect of the disclosure provides a portable computed tomography (CT) system. The system may include an O-shaped gantry defining an opening for a to-be-imaged object to be placed. The system may include an x-ray source operably coupled to the O-shaped gantry. The system may include a flat panel detector (FPD) operably coupled to the O-shaped gantry. The FPD may include an x-ray absorbing sensor layer and a detector pixel array. The system may include an antiscatter grid (ASG) operably coupled to a side of the FPD facing the opening of the O-shaped gantry. The ASG may include a plurality of vertical walls defining open-ended channels and formed of a radiation-absorbing material. The open-ended channels may be arranged in a geometric pattern pointed toward the x-ray source to receive x-rays in an x-ray emission path from the x-ray source. A pitch between the vertical walls of the ASG may be larger than a pitch of the detector pixel array.

Yet another aspect of the disclosure provides an image data correction method for an x-ray imaging system. The method may include the step of receiving, from a flat panel detector (FPD) of the x-ray imaging system, data representative of an x-ray image of at least a portion of an object. The method may include the step of estimating a residual scatter intensity of x-ray radiation reaching the FPD from an x-ray source of the x-ray imaging system. Using the portable CT scanner according to the present technology, for example, correction of the residual scatter intensity may be accomplished, at least in part, by measuring signal intensity variations in the FPD or detector pixel array to facilitate an improvement in the quality of the x-ray image.

A portable CT system according to the present technology may use an O-shaped gantry, which allows for a robust implementation of an antiscatter grid (ASG) (e.g., a 2D ASG) and the disclosed residual scatter correction method.

Correction of the residual scatter intensity according to the present technology may be accomplished, at least in part, by measuring signal intensity variations in the FPD or detector pixel array to facilitate an improvement in the quality of the x-ray image An O-shaped gantry is mechanically more stable; a position of the x-ray source in relation to the detector does not change during gantry rotation. As a result of this mechanical stability, an O-shaped gantry makes sure that a 2D-ASG's footprint (or shadow) does not change during gantry rotation, which aids in the reliability of the disclosed scatter correction method. Hence, image quality can be improved substantially.

The O-shaped gantry design according to the present technology also advantageously provides sufficient mechanical support to x-ray tube and detector, such that: a footprint of the ASG (e.g., 2D ASG) in the x-ray image remains stationary throughout the gantry rotation, and the performance of residual scatter intensity estimation method as disclosed herein may be improved.

The CT scanners and associated methods according to the present technology may utilize flat panel detectors (FPDs) to enable imaging the whole brain with one or two gantry rotations. This makes the electromechanical system simpler and lighter. A lighter CT scanner is more portable. Such a light gantry can also allow tilting of the gantry to accommodate patients who cannot lay flat. Known portable CT scanners need a fast-rotating gantry that need to rotate many times (10-15 times) to be able to scan the whole brain. As a result, the gantry of such a known system must be strong to handle the g-forces. In addition, they require more x-ray output and a larger x-ray generator because they scan a small portion of the brain per gantry rotation.

Known portable CT systems use conventional CT detectors that are custom designed for each CT scanner. They are heavy and more expensive as compared to the CT scanners of the present technology, which employ FPDs that are lighter and cheaper than custom CT detectors. The CT scanner according to the present technology may be more suitable for CT perfusion and CT angio imaging than current portable CT scanners because 3-5 cm thick brain tissue in the craniocaudal direction needs to be imaged repeatedly for perfusion CT imaging. Such a 3-5 cm thick field of view can be achieved with the use of FPDs in the disclosed CT system, whereas existing CT systems may only cover 1-2 cm thick brain tissue during perfusion CT imaging, which is suboptimal.

The disclosure also relates generally to X-ray detectors and more particularly to a system and methods for using an anti-scatter grid to significantly enhance the performance of flat panel X-ray detector. In one embodiment, the invention comprises two major components: 1) an antiscatter grid design, which aims to reduce scatter intensity reaching the flat panel detector (Schemes for integration of the antiscatter grid with the flat panel detector are described. Additionally, a method to correct residual scatter intensity transmitted through the antiscatter grid are described). 2) a new anti-scatter grid design and method were described to solve the pulse pile-up problem in photon counting x-ray detectors.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The present invention relates generally to X-ray detectors and more particularly to a system and a method for using antiscatter grids to significantly enhance the performance of flat panel X-ray detector. In one embodiment, the invention relates to a novel flat panel detector, which integrates a two dimensional (2D) antiscatter grid and a phosphor layer with the detector's pixel array. In one embodiment, the two dimensional anti scatter grid of apertures separated by radio-opaque, or at least radiation-absorbing, septa, placed over, on, or in contact with, the flat panel detector (FPD). In an example, a gap may exist between the ASG and the FPD. In one embodiment, 3D printing is used construct a 2D aperture array, such that each aperture may be precisely aligned towards the x-ray focal spot. In one embodiment, lithographic techniques are used construct a 2D aperture array, such that each aperture may be precisely aligned towards the x-ray focal spot. In one embodiment, the presence of thin septa combined with the absence of inter-septal spacers improves primary transmission, while the two dimensional aperture array provides efficient scatter rejection capability at levels not achievable with current scatter rejection devices.

In one embodiment, the invention relates to a signal adjustment mechanism to counteract the shadow effect that the antiscatter grid may have on the detector. In one embodiment, the flat panel detector is be redesigned such that the 2D grid is directly placed on the phosphor layer. In one embodiment, the normal flat panel detector continuous phosphor layer is replaced with a pixelated phosphor layer. In one embodiment, the pixels in the phosphor are separated with reflective septa, preventing diffusion of visible light photons neighboring detector pixels. In one embodiment, all or some of the walls of the 2D grid are aligned with the septa in the phosphor layer, minimizing the "inactive" area of the flat panel detector. It is believed that benefit cannot be achieved with the conventional approach where the grid is mounted on the top of the protective detector cover because the walls cannot be perfectly aligned with the septa of phosphor layer. It is believed that advantages of this hybrid design over existing flat panel detectors include: Pixelated phosphor structure reduces cross-talk between detector pixels, improves spatial resolution; 2D grid provides better scatter absorption and improved primary x-ray transmission with respect to conventional antiscatter grids. In return, it reduces noise in x-ray images. Integration of pixelated phosphor with the 2D antiscatter grid reduces the percentage of "inactive" detector area, thus more primary x-rays will be detected by the detector.

In one embodiment the present invention contemplates an x-ray imaging device, comprising: a) an x-ray source; b) a two dimensional selective electromagnetic radiation transmission grid comprising: i) a plurality of vertical walls, wherein the walls are connected to each other in a geometric pattern and pointed towards the x-ray source; ii) a plurality of open ended channels, wherein the open ended channels are defined by the plurality of vertical walls; and c) a flat panel detector comprising a phosphor layer and a detector pixel array, wherein the grid is in contact with the flat panel detector. In one embodiment, the vertical walls comprise an essentially radiation-opaque, or at least radiation-absorbing, material. In one embodiment, the vertical walls comprise an at least partially radiation-opaque, or at least radiation-absorbing, material. In one embodiment, the phosphor layer is composed of pixels, and pixels are separated with reflective walls. In one embodiment, the vertical walls of the grid are aligned with the reflective walls of the phosphor layer. In one embodiment, the phosphor layer is continuous, and the grid is placed directly on the phosphor layer. In one embodiment, the separation (pitch) between the grid's vertical walls is larger than the pitch of the detector's pixel array, and vertical walls are not aligned with detector's pixel array. In one embodiment, the grid's pitch and height may vary spatially across the flat panel detector. In one embodiment, there is a gap between the grid and phosphor layer. It is believed that this approach makes integration of large area grids with large area flat panel detectors feasible. In one embodiment, the flat panel detector comprises amorphous silicon pixel array. In one embodiment, the flat panel detector further comprises a complementary metal oxide semiconductor (CMOS) pixel array. In one embodiment, the geometric pattern is rectangular. In one embodiment, geometric pattern is hexagonal. In one embodiment, the at least one structural element comprises a plurality of radio-opaque, or at least radiation absorbing, sheets, such as metal sheets. In one embodiment, the element extends at least between two of the plurality of radio-opaque, or at least radiation-absorbing, sheets and on both sides of at least one of the radio-opaque, or at least radiation absorbing, sheets. In one embodiment, the grid is a scatter measurement and correction grid, such as described in Example 7. In one embodiment, the device further comprises a correction algorithm. In one embodiment, the correction algorithm corrects a transmitted residual scatter intensity.

In one embodiment, the present invention contemplates an x-ray imaging device, comprising: a) an x-ray source; b) a two dimensional selective electromagnetic radiation transmission grid comprising: i) a plurality of septa, wherein the septa are connected to each other in a geometric pattern and pointed towards the x-ray source; ii) a plurality of open ended channels, wherein the open ended channels are defined by the plurality of septa; and c) a flat panel detector configured underneath the plurality of septa and comprising a plurality of photon counting pixels, wherein the grid is over, on, or in contact with, the flat panel detector. In an example, a gap may exist between the ASG and the FPD. In one embodiment, there is a gap between the grid and the flat panel detector (or sensor). In one embodiment, the septa comprise an essentially radiation-opaque, or at least radiation-absorbing, material. In one embodiment, the flat panel detector comprises a Cadmium Telluride x-ray sensor. In one embodiment, the flat panel detector comprises Cadmium Zinc Telluride x-ray sensor. In one embodiment, the flat panel detector comprises a Silicon x-ray sensor. In one embodiment, the flat panel detector further comprises a complementary metal oxide semiconductor (CMOS) pixel array. In one embodiment, the geometric pattern is rectangular. In one embodiment, the geometric pattern is hexagonal. In one embodiment, the at least one structural element comprises a plurality of radio-opaque, or at least radiation absorbing, sheets. In one embodiment, the sintered element extends at least between two of the plurality of sheets and on both sides of at least one of the sheets. In one embodiment, the grid is a scatter measurement and correction grid. In one embodiment, the device further comprises a correction algorithm. In one embodiment, the correction algorithm corrects a transmitted residual scatter intensity. Correction of the residual scatter intensity may be accomplished, at least in part, by measuring signal intensity variations in the FPD or detector pixel array to facilitate an improvement in the quality of the x-ray image. In one embodiment, each radio-opaque, or at least radiation-absorbing, sheet in the grid is composed of sections with different height and thicknesses. In one embodiment, the grid's shadow generates high and low x-ray fluence regions, or fluence modulation, incident on the flat panel detector. It is believed that the fluence modulation pattern is controlled by changing the physical properties of the grid. In one embodiment, the modulation pattern is used to correct pulse pile up in the photon counting pixels.

In one embodiment, the present invention contemplates an x-ray imaging device, comprising: a) an x-ray source; b) a two dimensional selective electromagnetic radiation transmission grid comprising: i) a plurality of vertical walls, wherein the walls are connected to each other in a geometric pattern and pointed towards the x-ray source; ii) a plurality of open ended channels, wherein the open ended channels are defined by the plurality of vertical walls; and c) a flat panel detector comprising a phosphor layer and a detector pixel array, wherein the grid is over, on, or in contact with, the flat panel detector. In an example, a gap may exist between the ASG and the FPD. In one embodiment, the vertical walls comprise an essentially radiation-opaque, or at least radiation-absorbing, material. In one embodiment, the phosphor layer is divided into pixels with reflective walls. In one embodiment, the vertical walls of the grid are aligned with the reflective walls of the phosphor layer. In one embodiment, the phosphor layer is continuous, and the grid is placed directly on the phosphor layer. In one embodiment, there is a gap between the phosphor layer and the grid. In one embodiment, the separation (pitch) between the grid's vertical walls is larger than the pitch of the detector's pixel array, and vertical walls are not aligned with detector pixel array. In one embodiment, the grid's pitch and height may vary spatially across the flat panel detector. In one embodiment, there is a gap between the grid and phosphor layer. In one embodiment, the flat panel detector comprises amorphous silicon pixel array. In one embodiment, the flat panel detector further comprises a complementary metal oxide semiconductor (CMOS) pixel array. In one embodiment, the flat panel detector further comprises a solid-state x-ray sensor. In one embodiment, the geometric pattern is rectangular. In one embodiment, the geometric pattern is hexagonal. In one embodiment, at least one structural element comprises a plurality of radio-opaque, or at least radiation-absorbing, sheets. In one embodiment, the structural element extends at least between two of the plurality of radio-opaque, or at least radiation-absorbing, sheets and on both sides of at least one of the radio-opaque, or at least radiation-absorbing, sheets. In one embodiment, the grid is a scatter measurement and correction grid. In one embodiment, the device further comprises a correction algorithm. In one embodiment, the correction algorithm corrects a transmitted residual scatter intensity.

In one embodiment, the present invention contemplates an x-ray imaging device, comprising: a) an x-ray source; b) a two dimensional selective electromagnetic radiation transmission grid comprising: i) a plurality of septa, wherein the septa are connected to each other in a geometric pattern and pointed towards the x-ray source; ii) a plurality of open ended channels, wherein the open ended channels are defined by the plurality of septa; and c) a flat panel detector configured underneath the plurality of septa and comprising a plurality of photon counting pixels, wherein the grid is over, on, or in contact with, the flat panel detector. In an example, a gap may exist between the ASG and the FPD. In one embodiment, the two dimensional grid further comprises at least one structural element. In one embodiment, the septa comprises an essentially radiation-opaque, or at least radiation-absorbing, material. In one embodiment, the flat panel detector comprises silicon x-ray sensor. In one embodiment, the flat panel detector comprises a cadmium telluride x-ray sensor. In one embodiment, the flat panel detector comprises a cadmium zinc telluride x-ray sensor. In one embodiment, the flat panel detector further comprises a complementary metal oxide semiconductor (CMOS) pixel array. In one embodiment, the geometric pattern is rectangular. In one embodiment, the geometric pattern is hexagonal. In one embodiment, at least one structural element comprises a plurality of radio-opaque, or at least radiation-absorbing, sheets. In one embodiment, the radio-opaque, or at least radiation-absorbing, sheet in the grid is composed of sections with different height and thicknesses. In one embodiment, the grid's shadow generates high and low x-ray fluence regions, or fluence modulation, incident on the flat panel detector. In one embodiment, the modulation pattern is used to correct pulse pile up in the photon counting pixels. In one embodiment, the structural element extends at least between two of the plurality of radio-opaque, or at least radiation-absorbing, sheets and on both sides of at least one of the radio-opaque, or at least radiation-absorbing, sheets. In one embodiment, the grid is a scatter measurement and correction grid. In one embodiment, the device further comprises a correction algorithm. In one embodiment, the correction algorithm corrects a transmitted residual scatter intensity. In one embodiment, the grid provides a fluence modulation on the flat panel detector. In one embodiment, the grid has septa with uniform thickness. In one embodiment, the grid comprises different thicknesses and heights in septa to control x-ray fluence modulation pattern. In one embodiment, the grid's septal shadows provide lower fluence.

In one embodiment, the present invention contemplates an x-ray imaging device, comprising: a) an x-ray source; b) a two dimensional selective electromagnetic radiation transmission grid comprising: i) a plurality of vertical walls, wherein the walls are connected to each other in a geometric pattern and pointed towards the x-ray source; ii) a plurality of open ended channels, wherein the open ended channels are defined by the plurality of vertical walls; and c) a flat panel detector comprising a phosphor layer, wherein the grid is over, on, or in contact with, the flat panel detector. In an example, a gap may exist between the ASG and the FPD.

Other objects, advantages, and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "3D printing" describes a manufacturing process for metals or metal containing compounds to fabricate antiscatter grids.

As used herein, the term "sintered element" describes a material which may be used as a source material in a 3D printing process, such as direct metal laser sintering. Selective laser sintering allows for a large design freedom. Having a structural element that is built by selective laser sintering, the grid may be a highly complex three-dimensional structure that is not easily achievable by conventional molding or milling techniques. Therein, the technology of selective laser sintering, sometimes also known as direct metal laser sintering, is not any longer a prototype technology but becomes a production technology for the manufacturing of three-dimensional devices with demanding geometries.

As used herein, the term "essentially radiation-opaque material" is used herein to describe a material, which does not allow for the transmission of x-ray radiation. Examples of such materials are tungsten, tantalum, and lead. On the other hand, a "radiation-absorbing material" may absorb some, but not all, x-rays. The ASG according to the present technology may achieve its technically advantageous functions without being made of a "radiation-opaque material" that fully absorbs the x-rays, but rather in some embodiments can at least partially be made of a "radiation-absorbing material."

As used herein, the term "metal oxide semiconductor (CMOS)" is used herein to describe a technology for constructing integrated circuits. CMOS is also sometimes referred to as complementary-symmetry metal-oxide-semiconductor (or COS-MOS). The words "complementary-symmetry" refer to the fact that the typical design style with CMOS uses complementary and symmetrical pairs of p-type and n-type metal oxide semiconductor field effect transistors (MOSFETs) for logic functions. Two important characteristics of CMOS devices are high noise immunity and low static power consumption.

As used herein, the term "amorphous silicon (aSi) pixel array" is used herein to describe a technology for constructing flat panel x-ray detectors. aSi is often used in construction of photodiodes and thin film transistor (TFT) arrays employed in flat panel x-ray detectors.

As used herein, the term "energy integrating" is used herein to describe a type of x-ray detector, where only the accumulated x-ray energy in the x-ray detector is used to form the image. The number and energy of individual x-rays absorbed by the detector are not registered. An aSi pixel array integrated with a phosphor layer is an example for an energy integrating detector.

As used herein, the term "photon counting" is used herein to describe a type of x-ray detector, where energy of individual x-rays and the number of x-rays interacting with the detector are recorded. Cadmium Zinc Telluride (CZT) or Cadmium Telluride (CdTe) x-ray sensors integrated with energy resolving readout electronics are examples for photon counting x-ray detectors.

As used herein, the term "flat panel x-ray detector (FPD)" is used herein to describe an "area" x-ray detector that can generate a two dimensional x-ray image. FPD can be an energy integrating or a photon counting x-ray detector.

Abbreviations

ASG=antiscatter grid
2D ASG=two-dimensional antiscatter grid
FPD=flat panel detector
FDK=filtered backprojection
ART=adaptive radiation therapy
CT=computed tomography
CBCT=Cone beam computed tomography (also referred to as C-arm CT, cone beam volume CT, or flat panel CT)
MDCT=multi-detector CT
CTDI=CT dose index
CAX=projected location of the beam's central axis
SPR=Scatter-to-Primary ratio
SNR=signal-to-noise ratio
$K_{SNR}$=SNR improvement factor
$T_S$=scatter transmission fraction
$T_P$=primary transmission fraction
$I_S$=average scatter intensity
ROI=region of interest
BT=bow tie
DMLS=direct metal laser sintering
RT=radiation therapy
MTF=modulation transfer function
CT-to-ED=CT number to electron density
DVH=dose volume histograms
PTH=primary transmission histograms
MLEM=maximum likelihood expectation maximization

BRIEF DESCRIPTION OF THE DRAWINGS

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

FIG. 22 shows the diffusion of x-rays with a focused 2D antiscatter grid with a pixelated phosphor layer and pixel array. This shows that signal cross-talk may be eliminated with this design.

FIG. 24A: A 2D antiscatter grid comprised of a series of parallel hexagonal holes (red center line).

FIG. 24B. An image intensity profile generated by x-ray intensity through the hexagonal grid of FIG. 24A is shown as an orange line.

FIG. 28B shows a magnification of the red inset box in FIG. 28A, with a US quarter coin shown for dimensional purposes.

FIG. 30A: Without an antiscatter grid.

FIG. 30B: With conventional 1D ASG.

FIG. 30C: With a 2D ASG prototype, presented in this invention.

FIG. 31A: Standard constant septal thickness (e.g., without a footing). X-ray counts in pixel underneath the septal footprint is lower due to partial obstruction of fluence by septa. To reduce x-ray counts further, septal thickness should be increased.

FIG. 31B: An alternative solution is to use septa with a footing. Since the height of footing is 0-3 mm, it partially transmits x-rays.

FIG. 31C: Representative X-ray count profiles for septa configurations shown in FIG. 31A and FIG. 31B.

FIGS. 38A-38D present an x-ray imaging system utilizing a flat panel detector (FPD) with a 2D ASG as shown in FIG. 34A, according to some embodiments of the present technology.

FIGS. 41A and 41B present a comparison of images obtained using a CBCT system and processed without and with, respectively, the techniques of the method 3902 shown in FIG. 39G.

FIGS. 42A and 42B present a comparison of images obtained using the standard CBCT scanner and ultracompact CT scanner, respectively, according to the present technology.

DETAILED DESCRIPTION

Figure 1:
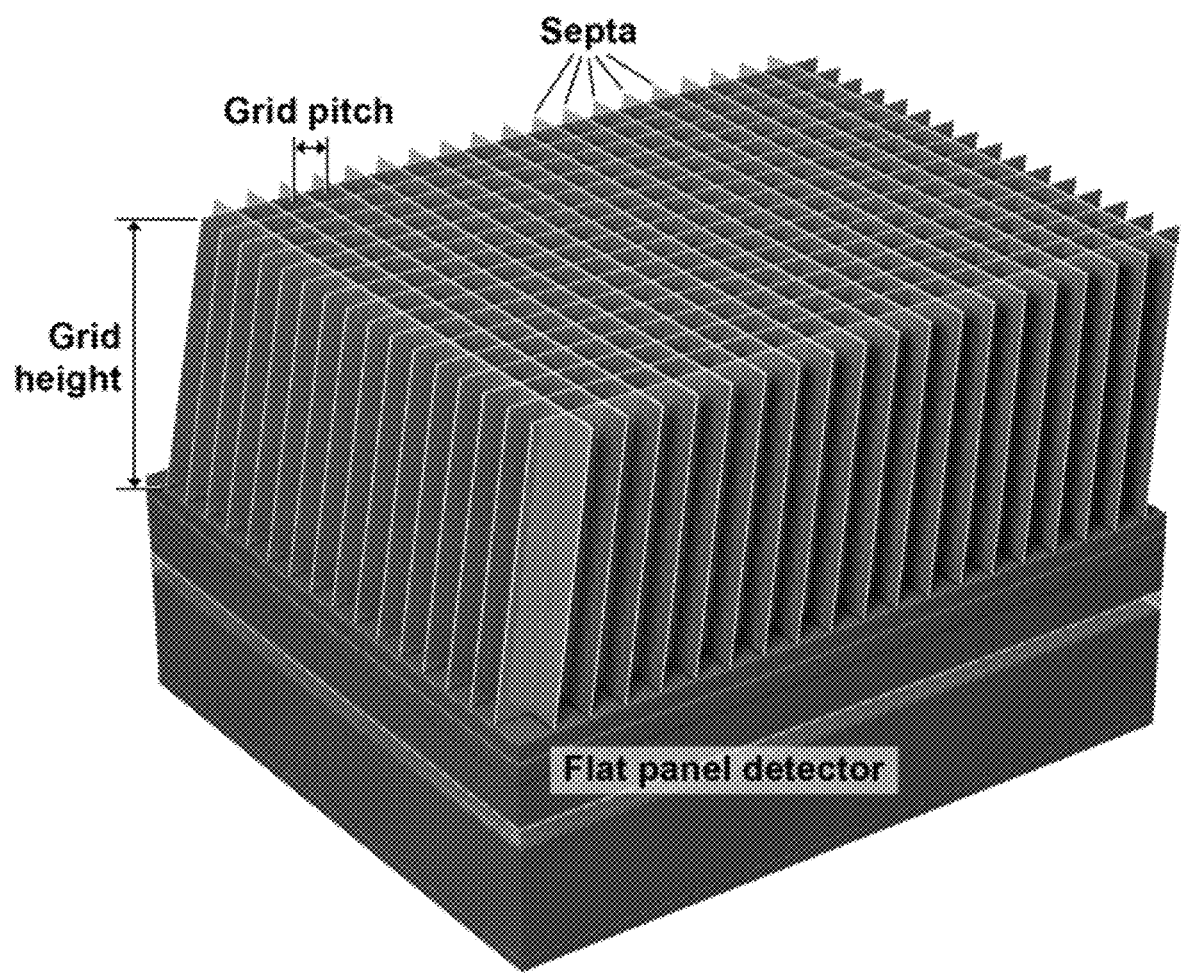
FIG. 1 shows an illustration of one embodiment of the two-dimensional focused antiscatter grid (2D ASG). Note the focusing property of the 2D array: each grid element (i.e. through-hole) is aligned, or pointed, towards the x-ray source to account for the divergence of the x-ray beam.

A portable CT system according to the present technology may use an O-shaped gantry, which allows for a robust implementation of an antiscatter grid (ASG) (e.g., a 2D ASG) and the disclosed residual scatter correction method. Correction of the residual scatter intensity according to the present technology may be accomplished, at least in part, by measuring signal intensity variations in the FPD or detector pixel array to facilitate an improvement in the quality of the x-ray image An O-shaped gantry is mechanically more stable; a position of the x-ray source in relation to the detector does not change during gantry rotation. As a result of this mechanical stability, an O-shaped gantry makes sure that a 2D-ASG's footprint (or shadow) does not change during gantry rotation, which aids in the reliability of the disclosed scatter correction method. Hence, image quality can be improved substantially.

The CT scanners and associated methods according to the present technology may utilize flat panel detectors (FPDs) to enable imaging the whole brain with one or two gantry rotations. This makes the electromechanical system simpler and lighter. A lighter CT scanner is more portable. Such a light gantry can also allow tilting of the gantry to accommodate patients who cannot lay flat. Known portable CT scanners need a fast-rotating gantry that need to rotate many times (10-15 times) to be able to scan the whole brain. As a result, the gantry of such a known system must be strong to handle the g-forces. In addition, they require more x-ray output and a larger x-ray generator because they scan a small portion of the brain per gantry rotation.

Known portable CT systems use conventional CT detectors that are custom designed for each CT scanner. They are heavy and more expensive as compared to the CT scanners of the present technology, which employ FPDs that are lighter and cheaper than custom CT detectors. The CT scanner according to the present technology may be more suitable for CT perfusion and CT angio imaging than current portable CT scanners because 3-5 cm thick brain tissue in the craniocaudal direction needs to be imaged repeatedly for perfusion CT imaging. Such a 3-5 cm thick field of view can be achieved with the use of FPDs in the disclosed CT system, whereas existing CT systems may only cover 1-2 cm thick brain tissue during perfusion CT imaging, which is suboptimal.

The disclosure also relates generally to X-ray detectors and more particularly to a system and a method for integrating an antiscatter grid with flat panel X-ray detectors to significantly enhance the performance of flat panel X-ray detector. In addition, the count rate and energy resolution performance of a photon counting flat panel X-ray detector may be enhanced by using the disclosed antiscatter grid.

For a specific example, in recent years, the utility of in-room CBCT imaging has been extensively investigated in the context of novel treatment strategies in radiation oncology. In the framework of adaptive radiation therapy (ART), patient treatments can be monitored for tumor and normal tissue anatomic changes by utilizing CBCT images acquired during the course of treatment. The role of CBCT imaging can be further expanded to modify treatment plans to account for anatomic changes, and hence, improve tumor control and reduce toxicity. Although much research has been done on evaluating the potential benefits of patient-specific treatment monitoring and ART in general, the utilization of CBCT images in the context of ART did not translate into clinical practice due to poor quality of CBCT images. Currently, the utility of CBCT imaging is limited to in-room patient setup corrections only.

Scattered radiation is widely acknowledged to be a major cause of image quality degradation in CBCT [4, 5]. Scatter leads to poor soft tissue visualization, reduces CT number accuracy, and generates image artifacts in CBCT images. To mitigate the scatter problem, last decade has seen widespread investigation of scatter suppression methods and devices. However, the desired improvement in CT number (Hounsfield Unit) accuracy and low contrast sensitivity has not been achieved.

To overcome the shortcomings of current scatter suppression methods, the present invention relates to a scatter rejection device: a two-dimensional focused antiscatter grid (2D ASG), for FPDs and CBCT systems. With respect to existing antiscatter grids (ASG), one embodiment the present invention design has fundamentally different properties: it consists of a 2D array of apertures separated by radio-opaque, or at least radiation-absorbing, septa, placed over, on, or in contact with, the flat panel detector (FPD). In an example, a gap may exist between the ASG and the FPD. In one embodiment, each aperture may be 2-5 mm in width, and 20-50 mm in height, and its central axis oriented toward the x-ray focal spot to match the divergence of the imaging beam. Furthermore, aluminum or fiber inter-septal spacers (used in radiographic ASGs) will be eliminated due to the mechanical strength of the tungsten 2D array.

In one embodiment, DMLS enables construction of a 2D aperture array with septal thicknesses down to 100 microns, and each aperture will be precisely aligned towards the x-ray focal spot. The presence of thin septa combined with the absence of inter-septal spacers may improve primary transmission, while the 2D aperture array will provide efficient scatter rejection capability at levels not achievable with current scatter rejection devices. Based on preliminary investigations, one embodiment of the current invention 2D ASG reduces scatter-to-primary ratio (SPR) by a factor of 30, whereas SPR reduction factor with radiographic ASGs is limited to 5 to 10. Additionally, 2D ASG may transmit 85% to 90% of the primary x-rays to the FPD in contrast to 60-70% primary transmission through radiographic ASGs.

Given the high level of primary transmission and efficient scatter suppression capability of the 2D ASG, it was determined that one embodiment of the current design enables significant enhancement in soft tissue visualization, and permit high level CT number accuracy. To assess this, several steps were taken:

Step 1 A range of 2D ASG prototypes with varying grid size and grid ratios were designed and constructed. Scatter rejection and primary transmission properties of the prototypes were characterized to determine the optimal 2D ASG geometry.

Step 2. Evaluate the impact of 2D ASG on CBCT image quality. In a comprehensive set of experiments, the improvement in CBCT image quality metrics were evaluated with respect to the gold standard, multi-detector CT (MDCT) images.

It is important to note that CBCT is utilized in other applications such as vascular imaging [6], maxillofacial surgery [7], and spinal procedures [8]. The results of this investigation will therefore apply to other CBCT systems that use fixed source-detector geometry.

significance

While CBCT is the most frequently used in-room 3D imaging modality for patient setup corrections in radiation therapy (RT) [9], it additionally provides unique clinical information, thus far not exploited in the clinical practice of radiation therapy; CBCT images are acquired periodically during patient setups, often on a daily basis, capturing 3D anatomy of both normal tissue and tumors throughout treatment. It has been widely suggested that CBCT images can be utilized in treatment monitoring and plan modifications to enhance therapeutic ratio, key concepts in the adaptive radiation therapy paradigm (ART) [10]. Briefly, ART aims to improve tumor control and reduce toxicity by monitoring changes in normal tissues and tumors, and adapting treatment plans to such changes during the course of treatment.

The benefits of various ART approaches have been investigated for numerous disease sites; for example, Yang et al. showed that adaptive treatment replanning significantly improved quality of life in patients with nasopharyngeal carcinoma [11]. Several studies indicated that ART approach can significantly reduce parotid dose and improve dose coverage of targets in Head and Neck cancer [12-16]. In Bladder cancer, Foroudi et al. concluded that ART can provide better normal tissue sparing ratio than conventional approaches [17]. In cervix cancer, Tyagi et al. stated that ART approach is needed to prevent suboptimal treatment coverage and excessive toxicity [18].

The utility of CBCT in ART has been severely limited due to poor image quality. In treatment response monitoring, assessment of changes in anatomy is challenging due to poor soft tissue visualization [18-20]. At both the treatment replanning and adaptation phases, accuracy of structure delineation and deformable image registration deteriorate [21-24], and CBCT-based dose calculations are not clinically acceptable due to lack of CT number accuracy [24]. Due to poor image quality, clinical scope of CBCT has been limited to patient setup corrections since its introduction to clinical practice.

Due to the CBCT image quality issues described above, the vast majority of ART research is performed in academic centers using repeat higher-quality helical CT scans (rather than readily available in-room CBCT images). This approach is not feasible for most RT clinics due to personnel and resources needed to handle the increased workload. Moreover, some of the ART methods, such as online treatment adaptations before treatment delivery [17], cannot be deployed without an in-room imaging system such as CBCT. Thus if the image quality of CBCT were to be improved sufficiently, this would represent a breakthrough in enabling wide-spread implementation of ART strategies in clinical practice. Although not all RT patients may benefit from the ART approach, high quality CBCT images are still essential for identifying potential patients for treatment adaptations [19, 20, 25, 26].

Scattered radiation is one of the leading causes of poor image quality in CBCT [4, 5]. As each CBCT projection has a large field of view, significant amounts of scattered radiation originating from the patient reach the flat-panel detector (FPD), contaminating the image signal. Depending on the imaged anatomy and imaging geometry, the magnitude of scatter may exceed primary x-ray intensity by a factor of 3 to 5 in CBCT projections [4, 27-29]. Scattered radiation impacts 3 important aspects of image quality: 1) Scatter deteriorates the contrast between soft tissue structures. 2) Scatter greatly reduces accuracy of CT numbers, which is critical to accurate dose calculations in CBCT images. 3) Scatter induces image artifacts that impact both tissue visualization and quantitative accuracy.

To improve CT number accuracy in CBCT, a wide range of scatter correction methods have been investigated in the past decade, and such methods have been shown to improve CBCT image quality [29, 35-38]. However, the improvements have been insufficient due to two fundamental problems: 1) All scatter correction methods use a model to estimate the scatter signal as a function of multiple model parameters. Assumptions made in the model lead to discrepancies between the estimated scatter and true scatter under real imaging conditions. 2) In scatter correction methods, "scatter-free" image signal is restored after detection of scatter by the FPD. Thus, even an ideal correction method can only account for the bias in image signal amplitude due to scatter, and stochastic noise due to scatter cannot be removed from the image signal. Thus, soft tissue visualization cannot be improved due to stochastic noise of scatter [5, 28, 29]. To physically suppress scatter, conventional radiographic ASGs (constructed from alternating layers of lead septa and spacer strips) were extensively investigated for CBCT [39-41]. While reduction in image artifacts and improvement in accuracy of CT numbers were demonstrated, these fell short of desired image quality levels in CBCT [27, 42]. Due to relatively poor primary transmission through the radiographic ASGs, only modest improvements in low contrast resolution were achieved, and only under high scatter conditions [39, 43, 44].

An ideal solution would be to remove scatter before it is detected by the FPD, using an efficient scatter suppression device, which also maintains high primary transmission efficiency. Thus, the present invention a two dimensional focused antiscatter grid (2D ASG) dedicated for CBCT systems was investigated and developed. The preliminary assessment of the present invention indicates that the performance of the design may significantly close the gap in quantitative accuracy between CBCT and MDCT, and improve low contrast resolution to levels not achieved by existing scatter suppression devices and correction methods. Fabrication of the advanced design is not feasible using standard manufacturing techniques, and therefore new 3D printing technology may be used to construct the current invention 2D ASG.

Innovation

The present invention antiscatter grid design has the promise to significantly improve CT number accuracy and low contrast resolution for CBCT systems.

The present invention grid architecture represents a fundamental departure from existing antiscatter grid designs for FPDs. All current antiscatter grids for FPDs are based on the 1D Potter-Bucky grid architecture [2, 45] (i.e. a 1D grid is formed by stacking alternating strips of lead and spacers made from aluminum or fiber). The Potter-Bucky grid's inherent physical characteristics make it unsuitable for construction of 2D anti-scatter grids.

Thus, in the present invention, a novel grid architecture is utilized (FIG. 1): The present invention device consists of 2D array of square cross-sectioned grid elements separated by tungsten septa. The grid can be attached to the protective cover of the FPD, or it can be directly integrated with the x-ray absorbing sensor layer. To account for x-ray divergence in cone beam geometry, each grid element is aligned, or focused, towards the point x-ray source to maximize transmission of primary x-rays across the FPD. With respect to 1D Potter-Bucky grid, we reduced the grid pitch by more than an order of magnitude, and increased the septal thickness by a factor of 3 to 5 in the 2D grid (details described in Step 1). A radio-opaque, or at least radiation-absorbing, material, such as tungsten, was utilized to provide mechanical strength and higher radio-opacity, and eliminated inter-septal spacers. These design choices in the 2D ASG design were made to achieve both favorable imaging performance and ease of fabrication.

In the present invention, 2D ASG's septa do not have to be aligned with the pixel array in the flat panel detector. This is due to the pixel architecture in flat panel detectors and unique design of the 2D ASG: 2D ASG's septal pitch is in the order of several mms, which is a factor of 10 or more than the pitch of photodiode pixel array in the detector. As alignment of the 2D ASG's septa and detector's pixel array alignment is not needed, it is feasible to combine a 2D ASG with a flat panel detector. In contrast to the present invention, 2D antiscatter collimators.

Figure 11:
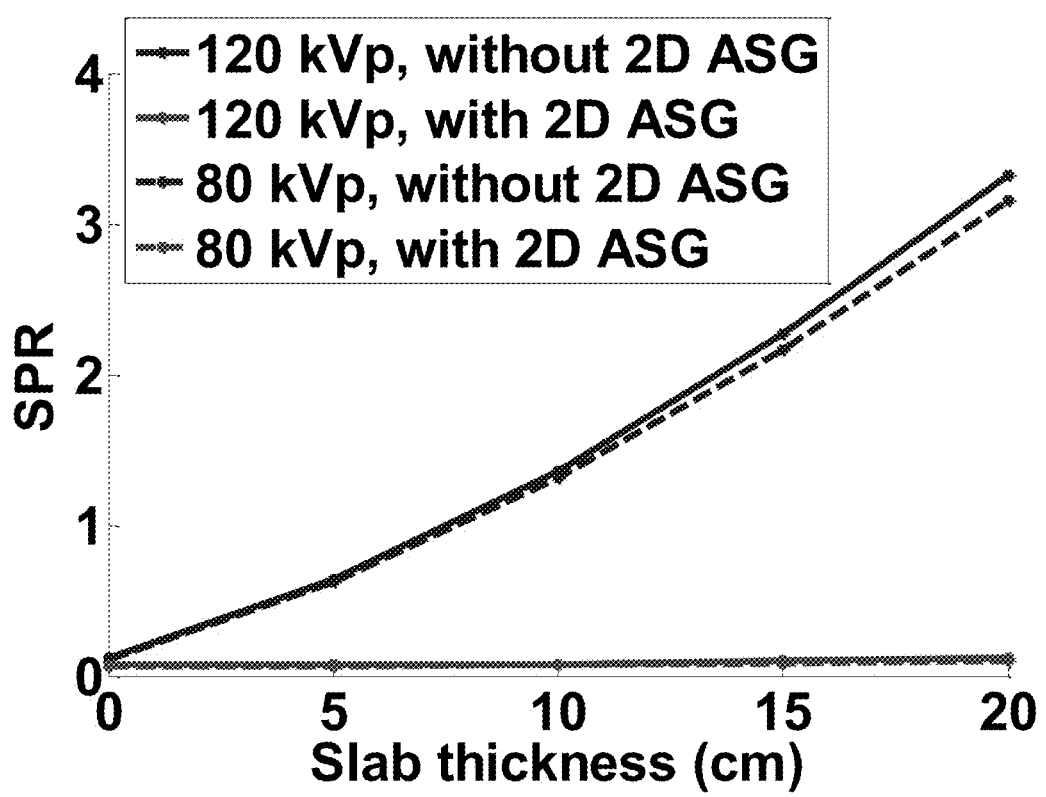
FIG. 11 shows measured SPR with and without 2D ASG prototype versus thickness of slab phantom. At 20 cm phantom thickness, the 2D ASG suppressed SPR from 3 to 0.1 at both 80 and 120 kVp [1].
Figure 12:
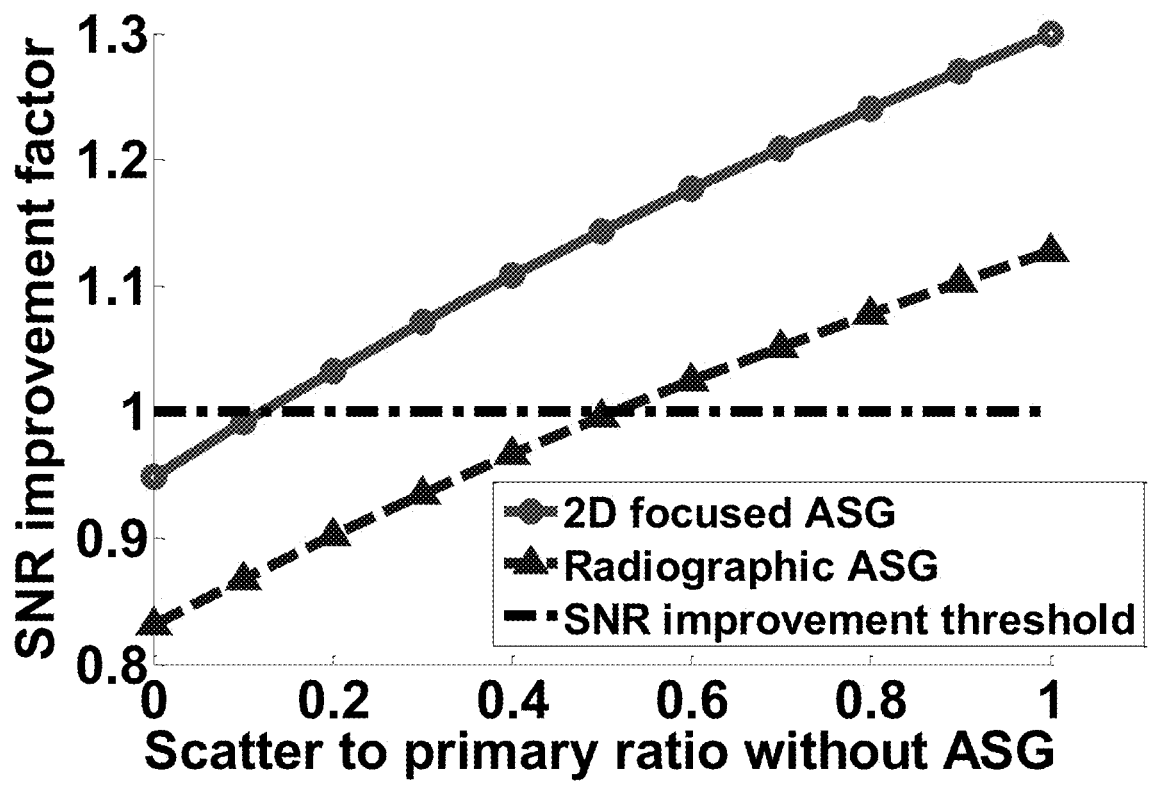
FIG. 12 shows SNR improvement factor of one embodiment of the 2D ASG (solid line, circles) and a radiographic ASG with 1D lead septa (dotted line, triangles) [1-3]. Both ASGs have the same grid ratios (i.e. 12). SNR improvement factor below 1 at a given scatter to primary ratio indicates that ASG degrades the SNR.

In preliminary experiments with lead based 2D grids that mimicked scatter suppression properties of the proposed design, scatter-to-primary ratio (SPR) was suppressed from 3 to about 0.1 (FIG. 11). Also it was predicted that signal-to-noise ratio (SNR) improvement provided by the 2D ASG will be higher than a radiographic ASG with comparable grid ratio (FIG. 12).

Fabrication of a 2D grid from thin enough radio-opaque, or at least radiation-absorbing, septa is a challenging problem due to limitations in conventional fabrication and machining methods. However, rapid progress in additive manufacturing methods for metals made in recent years now makes manufacturing of 2D ASGs viable [46]. In the current invention, advances in additive manufacturing technologies were exploited (also known as 3D printing) to build one embodiment of the 2D ASG. Specifically, Direct Metal Laser Sintering (DMLS) methods were utilized, which uses a focused, computer guided laser beam to sinter powdered tungsten to generate the ASG from a 3D computer model. DMLS processing of tungsten is a new, but commercially available technology, suitable for both rapid prototyping and serial production of 2D ASGs.

The high mechanical strength of the 2D grid obviates the need for inter-septal spacers. Commonly used in radiographic ASGs to provide mechanical support for 1D array of lead septa, inter-septal spacers contribute significantly to attenuation of the primary x-rays. They also impose a limit on the grid ratio, or grid height, as the thickness of spacers also increases with grid height, further reducing primary transmission. Due to absence of inter-septal spacers in the current invention 2D ASG, increasing grid height to improve scatter suppression is not penalized by reduced primary transmission. Another unique aspect of the current invention design is its focused grid geometry; each grid element will be aligned towards a true point x-ray source in the 3D computer model of the proposed design. Alignment of individual grid elements will be precisely replicated during manufacturing, since the DMLS process is directly driven by the 3D model of the current invention 2D ASG. Hence, high primary transmission property of the current invention design will be maintained across the active area of the FPD.

Figure 13:
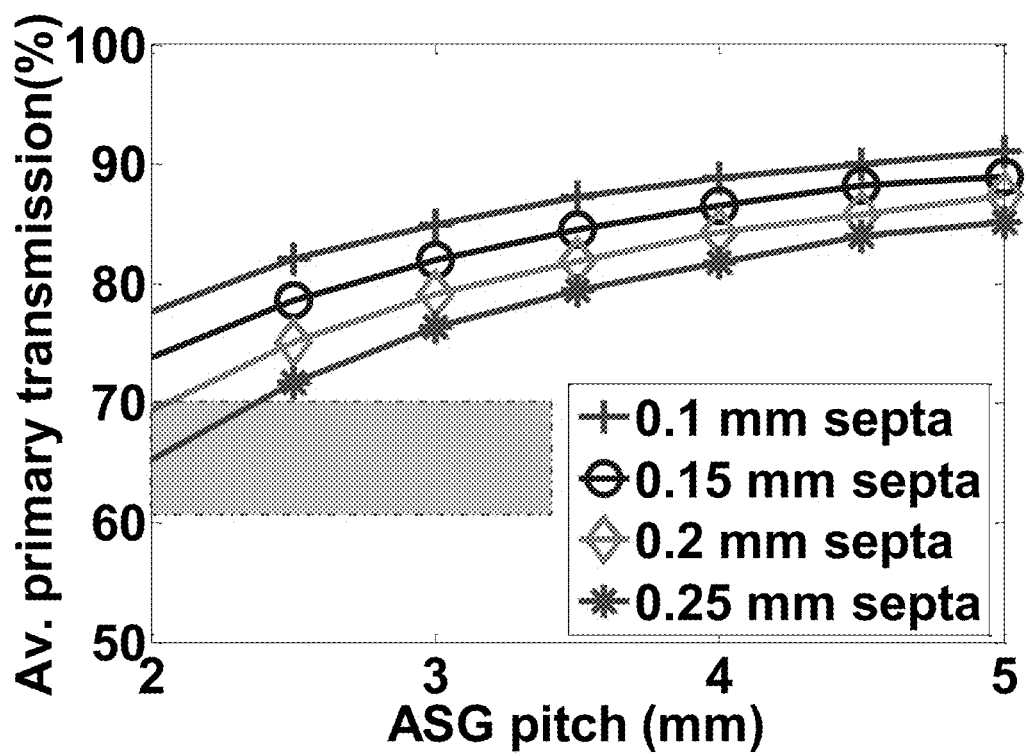
FIG. 13 shows the average primary transmission fraction through one embodiment of the 2D ASG as a function of ASG's grid pitch and septal thickness. The average primary transmission fraction of radiographic ASGs is 60-70%, indicated by red rectangle.

As a cumulative effect of the design properties described above, the primary transmission through the current invention design is predicted to be 20%-50% higher than current radiographic ASGs (FIG. 13). Due to the 2D grid structure, the current invention design with a grid ratio of 12 is expected to suppress the scattered radiation intensity by more than a factor of 2 when compared to a radiographic ASG with the same grid ratio [1, 2]. Given the high primary transmission and scatter suppression efficiency of the proposed 2D ASG, a robust improvement in low contrast resolution and CT number accuracy will be achieved in CBCT images. It is believed that the level of quantitative accuracy provided by the 2D ASG will enable accurate CBCT-based dose calculations in RT.

While two other 2D ASGs have been investigated for mammography, and MDCT systems in recent years, their applicability to FPD-based CBCT systems is not feasible. The 2D ASG for mammography systems is fabricated from copper [47], which is not radio-opaque, or radiation-absorbing, enough in the energy range of 60 to 125 keV used in CBCT systems for RT. Moreover, the x-ray lithographic process used in fabrication of the mammographic grid is not suitable for fabrication at the physical dimensions of the current invention, for processing of tungsten. The 2D ASG for the third generation MDCT is built from a tungsten polymer blend using a micro-molding technology [48]. While the ASG for MDCT systems may appear similar to the current invention design, parallel (i.e. not focused) grid elements make it unsuitable for use with a flat detector CBCT system.

Research Approach

Step 1. Simulate and Build 2D ASG Prototypes Using DMLS Technology, and Characterize their Signal Transmission Properties.

The goal of Step 1 is to determine the optimal physical properties, or geometry parameters, of the 2D ASG that would provide the desired improvement in CT number accuracy and low contrast resolution within the constraints of the CBCT system and of DMLS technology. Scatter and primary transmission properties are primarily determined by four parameters: grid ratio (i.e. height-to-width ratio of the grid element), septal thickness, grid pitch (i.e. sum of grid element width and septal thickness), and grid height. The impact of these geometry parameters on the CBCT image quality metrics will be investigated, and optimal values for each geometry parameter will be determined as outlined below.

Simulation of 2D ASG by Monte Carlo calculations: Optimization of ASG's geometry covers a large parameter space that might be expensive to explore by brute-force experimental approach. As outlined in the next paragraphs, preliminary experiments were performed and a computational ASG model developed to better understand the signal transmission characteristics of 2D ASG. While these studies will be useful to guide the development of prototypes, a Monte Carlo based ASG model was also developed to better understand the physics behind 2D ASG's x-ray transmission properties. This way, a better prediction the transmission properties of the subsequent prototypes can be made. The EGSnrc package [49] was employed for simulations, which was validated for CBCT [50]. Herein, the simulated 2D ASG was validated against the measurements performed with the first 2D ASG prototype.

Optimization of grid ratio for desired accuracy in CT numbers: The scatter component in image signal, commonly quantified by SPR metric, dominates the degradation in CT number accuracy. Siewerdsen and Jaffray's work [4] showed that suppressing the SPR down to 0.1 in CBCT projections kept the overall CT number accuracy within 2-4% of true CT numbers. An aim was to suppress SPR level to 0.1 with the 2D FASG. This level of accuracy would be sufficient for CBCT based RT dose calculations (this was evaluated in Step 3).

The level of SPR suppression is directly correlated with the grid ratio of the ASG. In preliminary experiments with a 2D ASG prototype casted from lead [1], it was observed that SPR was suppressed from 3 to 0.1 with a grid ratio of 12 (see FIG. 11). It was predicted that the 2D ASG with a grid ratio of 12 can suppress SPR even below 0.1 for the same imaging conditions in [1], due to its higher primary transmission fraction than the lead based 2D ASG prototype. Thus, the grid ratio of 12 was used in the first prototype. Based on the measured SPR suppression levels and SPR levels predicted by Monte Carlo simulations, a grid ratio range of 8 to 16 will be investigated in the subsequent ASG prototyping cycles to suppress the SPR to 0.1.

Optimization of grid pitch and septal thickness for improved visualization of low contrast objects: Percentage of primary x-rays transmitted through the grid plays a key role in the improvement in CNR and SNR metrics (i.e. metrics to quantify the improvement in low contrast visualization). Based on the computational 2D ASG model [1], septal thickness and the grid pitch of the first 2D ASG prototype will be 100 microns and 3 mm, respectively. With this grid geometry, primary transmission fraction can be improved to >85% (FIG. 13), which is expected to provide significant SNR improvement over radiographic ASG.

Figure 14A:
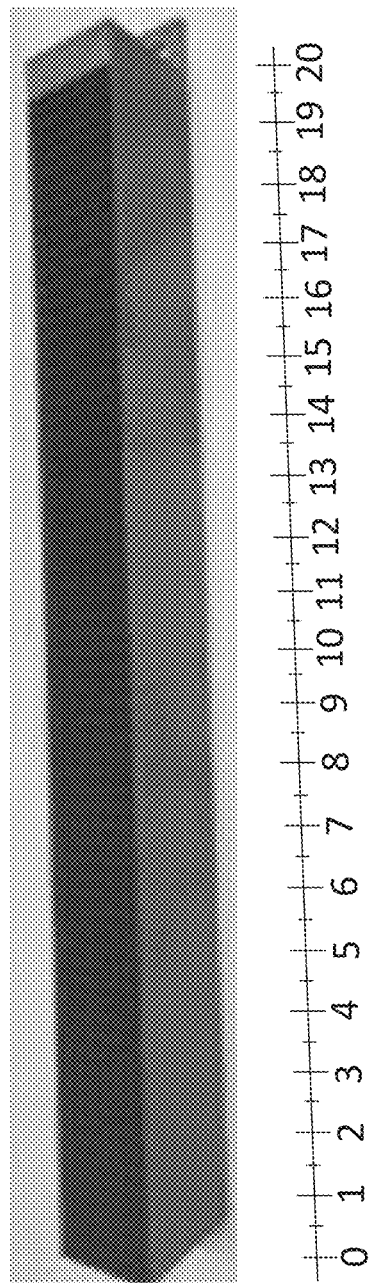
FIG. 14A shows one embodiment of the 2D ASG built for FPD and CBCT applications.
Figure 14B:
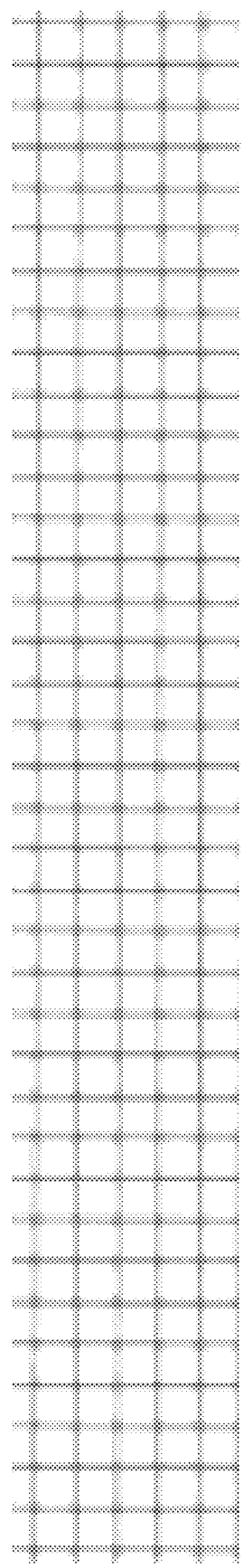
FIG. 14B shows the shadow, or footprint, of the 2D ASG appears as a darker grid pattern in the FPD image. X-ray intensity reaching the FPD is lower in the shadow, since 2D ASG's septa partially block primary x-rays. If this intensity variation is not corrected, it will lead to image artifacts, and makes the use of 2D ASG unfeasible.

Depending on the primary transmission measurements, grid pitches will be explored down to 5 mm to achieve primary transmission fraction of 85 to 90%. Tungsten thickness of 100 microns is more than sufficient to absorb scattered radiation in the diagnostic x-ray energy range. Radiographic ASGs typically consist of 25 to 35 microns thick lead septa. FIG. 14A shows one embodiment of the 2D ASG built for FPD and CBCT applications. FIG. 14B shows the shadow, or footprint, of the 2D ASG appears as a darker grid pattern in the FPD image. X-ray intensity reaching the FPD is lower in the shadow, since 2D ASG's septa partially block primary x-rays. If this intensity variation is not corrected, it will lead to image artifacts, and makes the use of 2D ASG unfeasible.

The limit on grid height for physical clearance between the patient and the CBCT gantry: Given the geometry of linac mounted CBCT systems, the maximum grid height may be limited to 5 cm to maintain sufficient physical clearance between the patient and the FPD/ASG assembly. The first 2D ASG prototype will have a grid ratio of 12, grid pitch of 3 mm, and grid height of 36 mm. Although the grid height limit also implies limits on the grid pitch and ratio, it is expected that the optimum grid pitch and ratio will be achieved without increasing the grid height beyond the 5 cm limit.

Does the ASG's tungsten footprint introduce dead pixel zones in the FPD? The signal will be reduced in detector pixels underneath the footprint of tungsten septa. If the signal reduction is severe enough, pixels underneath the footprint of 2D ASG would appear as dead zones, which may negatively impact both spatial and low contrast resolution in CBCT images. Based on computer simulations [1], it is not anticipated that this problem will occur due to the relatively thin septa with respect to detector pixel size; less than 5% of all detector pixels are expected to have signal reduction by more than 50% due to proposed FASG's footprint. Even if these pixels are treated as "dead" pixels, the signal at dead pixel locations can be easily recovered by the remaining 95% of pixels using interpolation methods.

Construction of 2D ASG prototypes using DMLS technology: The ASG prototypes used in Step 1 were initially 10×10 cm$^2$ in size to minimize production costs. This size will be more than sufficient to measure the primary and scatter transmission characteristics of the design.

Experiment setup: Throughout this invention, ASGs were evaluated in a clinical, linac mounted CBCT system (TrueBeam, Varian Medical Systems, Palo Alto, CA). This approach enabled evaluation of the 2D ASG using clinical imaging geometry, system components, and protocols [51]. Two utilized TrueBeams have "research mode" capability, which allowed full control the CBCT system parameters, and image processing outside the clinical CBCT system. In all experiments through Step 1 to 3, directly mounted the prototype 2FASGs on the FPD, and was employed with the "offset detector" CBCT geometry (also known as half-scan geometry) in TrueBeam linacs. It is envisioned that half-scan geometry is the optimal choice for the 2D ASG as it provides the largest field of view. While Varian's CBCT platform was selected for this project, the current invention design can be adapted to other CBCT systems, such as XVI (Elekta Oncology Systems, Norcross, GA).

Experimental details: With each ASG prototype, the scatter transmission fraction, average primary transmission fraction, and SPR suppression levels were characterized. Measurement of primary and scatter transmission will be performed in CBCT projections using established techniques, such as the beam-stop method [52]. The full detector area (30×40 cm$^2$) will be exposed to simulate imaging conditions in clinical systems, and SPR suppression characteristics of each prototype will be investigated for patient thicknesses up to 50 cm, where the goal is to limit SPR to 0.1 even in high SPR environments. The signal reduction due to ASG's footprint will also be evaluated and results will be compared to the Monte Carlo model. Based on the scatter suppression and primary transmission properties of the first prototype, the geometry of the subsequent prototype will be generated to minimize the discrepancy between the desired and measured ASG performance metrics. It is estimated that 4 to 6 cycles of ASG prototype construction and characterization will be performed to determine the optimal ASG geometry parameters.

Step 2. Evaluate the Impact of 2D ASG on CBCT Image Quality.

In Step 2, improvements in CBCT image quality provided by the 2D ASG were characterized. The prototype to be used in Step 2 will be based on the optimal ASG geometry parameters determined in Step 1, and it will cover the entire active area of the FPD to reflect the image quality improvements in clinical CBCT systems.

Experiment setup: As in Step 1, experiments will be performed in "offset detector" CBCT geometry using the CBCT system in TrueBeam linac. To emulate clinical CBCT imaging protocols, the bowtie filter was employed to demonstrate the combined effects of bowtie filter and 2D ASG on scatter suppression and CBCT image quality. CBCT images will be reconstructed using the FDK filtered back-projection algorithm [53]. Beam hardening [54], image lag [55], and ring artifact correction [56] algorithms will be implemented in the post-processing stage of CBCT projections to further improve CT number accuracy.

Is 2D ASG's weight an issue for the CBCT gantry? For the geometry parameter ranges outlined in Step 1, the maximum weight of detector and grid assembly will be 18.1 kg, which is below the CBCT detector arm's payload limit of 20 kg in the TrueBeam linac [51].

Correction of 2D ASG's footprint in CBCT projections in the presence of gantry flex: Linac gantry and the CBCT imaging arms flex (or sag) slightly due to gravity as they rotate around the patient. Projected location of x-ray source on the FPD will vary due to flex, and footprint (x-ray shadow) of the ASG's septa projects to slightly different locations on the FPD as a function of gantry angle.

The characteristics of linac-CBCT gantry flex are reproducible, or "systematic", as a function of gantry angle, which makes the correction of 2D ASG's footprint feasible [57-61]. A gantry angle-specific flat field correction method was first implemented, which has been shown to successfully correct the footprint of radiographic ASGs in the presence of gantry flex [40, 62]. This process correction can easily be automated and needed calibration images can be acquired during routine monthly linac-CBCT QA sessions. Although gantry flex is quite reproducible over extended periods of time, small "random" variations in gantry flex exist [57], which may lead to ring artifacts in CBCT images. To account for this, a post-reconstruction ring artifact suppression algorithm, [63]. Such algorithms have already been successfully implemented in clinical CBCT systems will be implemented [51, 64]. It is worth mentioning that gantry flex will be insignificant in a ring based linac gantry (rather than c-arm like gantry), which may negate the need for the ASG footprint correction methods described above. Ring based linacs have been readily offered by a linac Vendor (Vero, BrainLab, Munich, Germany).

Studies to be performed: The studies in Step 2 will be an extensive set of CBCT image quality characterization experiments. The magnitude and effects of scattered radiation on image quality strongly depend on the size, shape, and composition of the imaged anatomy. Thus, we will employ a comprehensive set of anatomy and patient size specific phantoms to evaluate the imaging performance. To assess the effect of anatomy, head, thorax, and pelvis anthropomorphic phantoms will be utilized. To assess the effect of phantom size and measure various image quality metrics, the Catphan phantoms will be utilized (The Phantom Laboratory, Salem, NY). Catphan can be fitted into various size "body" phantoms mimicking pelvis/abdomen anatomy. With body phantoms, we will simulate patient sizes up to 55 cm lateral and 45 cm anteroposterior separation. Catphan phantoms were evaluated at 3 different body sizes. Imaging technique (tube kVp, mAs) will be determined based on the clinical protocols in TrueBeam.

For each phantom, the following 3 sets of images: 1) CBCT with radiographic ASG, 2) CBCT with the proposed 2D ASG, 3) MDCT using the CT simulator was acquired. MDCT image represents the gold standard in image quality, thus, image quality of CBCT images will be benchmarked against the MDCT images in each imaging experiment. The CT dose index (CTDI) was similar for both CBCT and MDCT to suppress the impact of imaging dose on image quality.

Established methods and metrics were employed for image quality evaluations [4, 28]; contrast to noise ratio (CNR) was measured, a surrogate for improvement in soft tissue visualization, using contrast objects embedded in phantoms. Statistics of CT numbers (mean and standard deviation) were measured in 10-15 different regions of interest to assess the accuracy of CT numbers. In experiments with Catphan phantoms, modulation transfer function (MTF), were also measured in addition to the metrics mentioned above.

Measurements in CBCT and MDCT images will enable us to precisely characterize the difference in image quality metrics across 3 different systems (i.e. radiographic ASG, proposed 2D ASG, and MDCT) for different anatomies and patient sizes. To identify the similarities (and differences) among different systems (2D ASG vs. MDCT and 2D ASG vs. radiographic ASG), the differences in image quality metrics will tested for statistical significance.

Step 3. Validate Improvements in the Accuracy of Radiation Therapy Dose Calculations.

Achieving clinically acceptable dosimetric accuracy in CBCT-based treatment plans is an important milestone for the invention. In Step 3, whether improved CBCT image quality is sufficient for treatment dose calculations in megavoltage external beam RT will be tested.

Experiment setup: Step 3 will employ the image sets acquired in Step 2 for treatment plan dose calculations. The only new imaging experiments in Step 3 will be with CT number to electron density (CT-to-ED) phantoms; to be able to calculate dose in CBCT or CT image, CT numbers are converted to either electron or mass density values in the treatment planning system. To achieve this, CBCT and MDCT images of CT-to-ED phantoms will be acquired, and CT-to-ED tables will be established [65].

Evaluation of dosimetric accuracy in CBCT: In the Radiation Oncology Clinic, dosimetric accuracy analysis has been routinely performed for both clinical cases and research projects [66-68]. The same tools and methodology will be utilized, such as point-by-point dosimetric comparisons and analysis of dose volume histograms (DVH) [69, 70], to quantify the dosimetric accuracy provided by 2D ASG. As in Step 2, MDCT-based treatment plans and dose distributions are considered the gold standard. For a given phantom, CBCT-based dose distributions will be directly compared to the MDCT-based dose in each treatment plan. Below, the general method for dose accuracy evaluations for each anatomical site or phantom is provided.)

For each phantom, all 3 sets of images acquired were utilized in Step 2 (i.e. CBCT with radiographic ASG, CBCT with 2D ASG, MDCT). To generate radiation treatment plans, images will be imported into a clinical treatment planning system (Eclipse, Varian Medical Systems, Palo Alto, CA). 2) Depending on the anatomy depicted in the phantom, relevant targets and organs at risk structures were generated. 3) In each CBCT image, treatment plans will be generated using both 3D conformal and intensity modulated radiation therapy techniques. Attention will be paid to emulate realistic treatment plan scenarios. A clinically employed list of organs at risk and target dose constraints was used to optimize the plans. Once the plan was optimized, final treatment plan and dose calculation parameters were copied to the corresponding MDCT image set, and the dose will be recalculated to obtain the "ground truth" dose distributions. This way, the dose difference between CBCT and MDCT-based plans will only be due to differences in CT numbers of image sets. 4) As in clinical plans, DVHs will be calculated for organs at risk and targets in both CBCT and MDCT based plans. A set of site-specific DVH metrics were selected to assess the dose distributions as in clinical cases (such as dose covering 95% of the target volume, mean lung dose etc.). Also, point-by-point dose comparisons will be performed between the CBCT and MDCT dose distributions. The statistical significance of differences in point-by-point dose distributions of CBCT and MDCT-based plans was tested. Statistical analysis will allow us to identify anatomies and imaging conditions that lead to dosimetric differences between CBCT and MDCT 5) From a clinical perspective, evaluation of "clinical" significance of dose differences by expert clinicians is a more relevant approach (e.g. Statistically significant differences at very low doses that occur close to skin may not be considered clinically significant). The differences in DVH metrics and dose distributions of CBCT and MDCT-based plans were evaluated from a clinical standpoint. With this approach, we Step to map out the anatomical sites, patient sizes, and treatment techniques that provide clinically acceptable treatment plans with the use of the proposed 2D ASG.

The impact of improved CBCT image quality may be moderate in the context of current clinical use of CBCT, which has been limited to in-room patient setup corrections. However, it is believed that the impact of improved CBCT image quality is best viewed in the context of enabling new paradigms in clinical practice, such as adaptive radiation therapy (ART). In-room CBCT imaging plays a key role in various components of ART framework, such as monitoring of normal tissue and tumor changes, and assessing dosimetric consequences during the course of treatment. Although much work has been done on the key tools for ART (e.g. deformable image registration, dose accumulation, and tissue segmentation tools), such tools don't work reliably with today's CBCT images due to lack of soft tissue visualization and inaccuracy of CT numbers. Furthermore, assessment of tumor response by a physician, and decision for treatment modification are also challenged by poor CBCT quality.

The lack of CBCT utilization in ART is a major roadblock to wider clinical implementation of ART, and poor CBCT image quality due to scatter is a major contributor to the problem. When successfully implemented, the current invention 2D ASG design represents a breakthrough in CBCT image quality improvement, in turn enabling treatment response monitoring and adaptation methods by using increasingly common linac-mounted CBCT systems. Also, CBCT is utilized in clinical applications outside radiation oncology, such as transarterial chemoembolization and maxillofacial surgery, where poor image quality due to scatter is considered a major drawback. Successful completion of this project will impact such applications of CBCT outside radiation therapy.

The current invention proposes both a novel architecture and use of a novel 3D printing technique, known as Direct Metal Laser Sintering (DMLS), for tungsten. The current invention grid architecture represents a fundamental departure from existing 1D antiscatter grid designs. All current antiscatter grids in CBCT are based on the 1D Potter-Bucky grid design, which is unsuitable for design of 2D antiscatter grids. The current invention architecture reduces the grid pitch by more than an order of magnitude, and increases the septal thickness by a factor of 3 to 5. Importantly, tungsten has been chosen to provide mechanical strength, higher radio-opacity, and eliminate inter-septal spacers. It is the use of DMLS which permits realization of a 2D grid and allows fabrication with tungsten. These deliberate design choices have been made to achieve both favorable imaging performance and fabrication feasibility.

Septal Shadow Aft Fluence Modulation

While Cone Beam Computed Tomography (CBCT) is routinely used as a 3D in-room imaging modality in radiation therapy, its poor soft tissue visualization and lack of material composition information is believed to prevent implementation of improvements in radiation therapy, such as CBCT-based treatment monitoring and treatment plan adaptations.

Currently used x-ray imagers utilize energy integrating detectors that create a 2D map of total energy deposited within an x-ray sensor. Consequently, information about the number of x-rays and the energy of each x-ray absorbed in the sensor is lost. This shortcoming of energy integrating detectors deteriorate image quality, prevent implementation of new technology for x-ray imaging, and increase radiation doses to patients during imaging procedures.

To address these shortcomings of energy integrating detectors, photon counting detectors were developed. For example, photon counting detectors can quantitate the energy of individual x-rays and count each x-ray that interacts with a detector. Although it is not necessary to understand the mechanism of an invention, it is believed that photon counting detectors will be integrated into future computed tomography and radiography systems, especially those contemplated herein.

Figure 23:
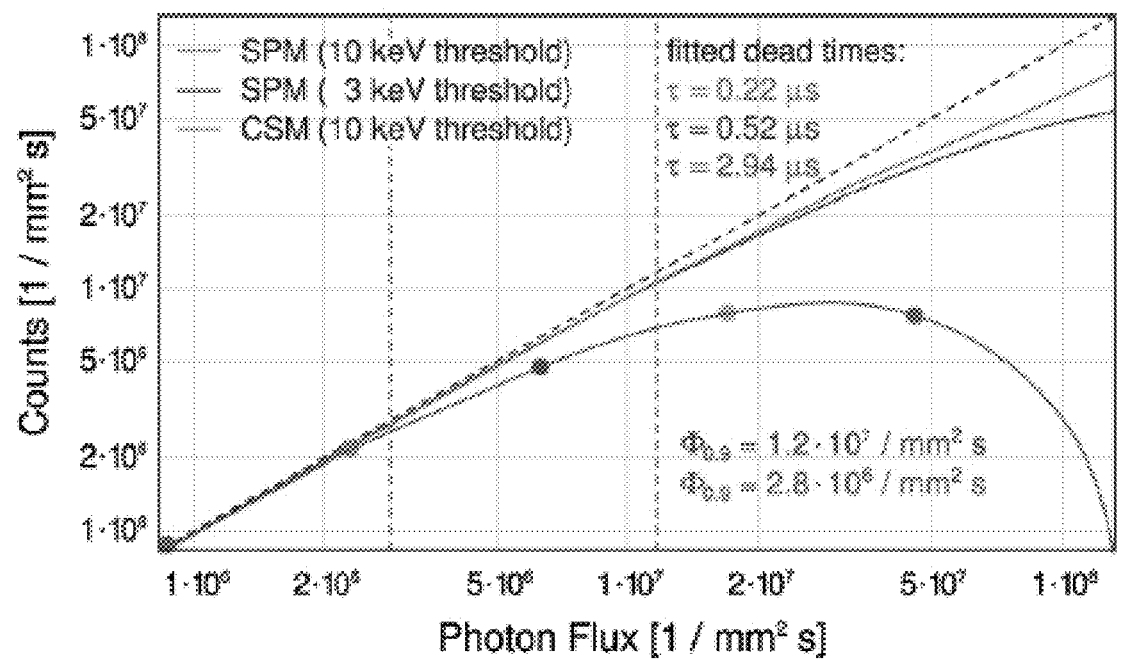
FIG. 23 presents a representative x-ray fluence chart demonstrating the "pulse pile-up" problem.
Y axis: Counts recorded by the "photon counting" detector
X axis: True number of counts incident on the detector
Ideal detector response is the dashed black line
Colored lines are the actual detector responses for 3 different detectors.
In the region indicated by the red transparent rectangle, detectors can significantly "underestimate" the true x-ray counts.

However, currently available photon counting detectors have several technical challenges that interfere with their utilization in clinical imaging systems. For example, in clinical imaging scenarios, x-ray incident flux on a detector can be quite high (e.g., up to $10^8$-$10^9$ x-rays per mm$^2$ per second). At this high x-ray flux photon counting detectors are unable to accurately count the individual x-rays (e.g., commonly referred to as a "pulse pile-up") and, in addition, the detected number of x-rays can be significantly different than the actual number of x-rays (e.g., a significant error rate). FIG. 23. Although it is not necessary to understand the mechanism of an invention, it is believed that this problem prevents the reconstruction of high quality x-ray images.

Figure 24A:
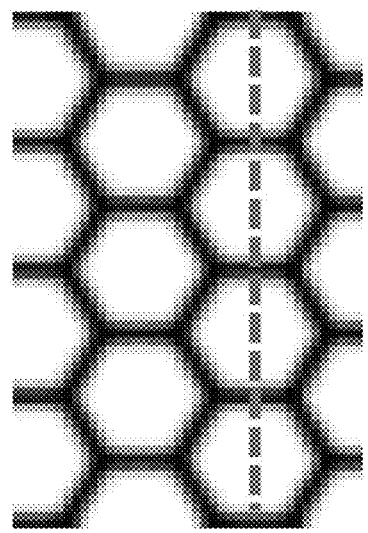
FIGS. 24A and 24B presents the generation of an x-ray image by a 2-D hexagonal grid.
Figure 24B:
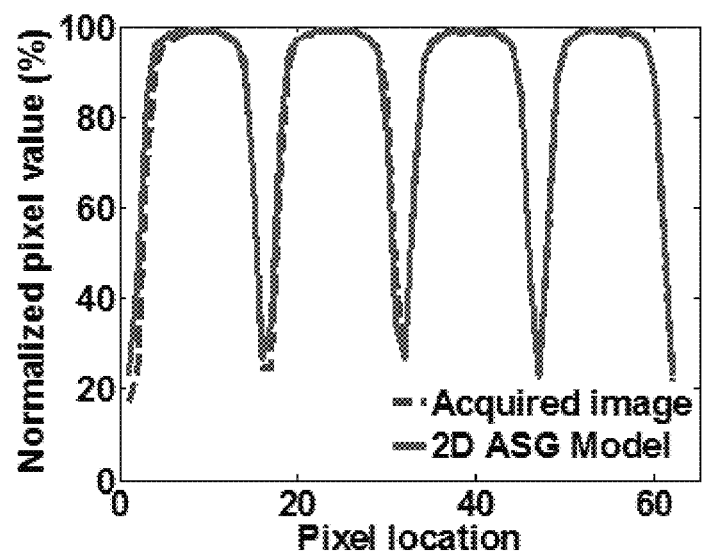

In one embodiment, a 2D anti-scatter grid comprises series of holes separated by a radio-opaque, or at least radiation-absorbing, septa (dashed red line). FIG. 24A. In one embodiment, the holes comprise any shape, but are preferably either square or hexagonal. See, FIG. 1. An image profile of one of these hexagonal hole series demonstrates the variations in x-ray flux depending on the pixel position within the hexagonal hole. FIG. 24B (orange line). It can be seen that a darker region of the hexagonal hole series in FIG. 24A corresponds to a 2D grid footprint (e.g., septal shadow) indicating a lower x-ray flux or intensity. Consequently, the pixels within the septal shadow encounter a significantly reduced x-ray flux as compared to pixels located within the 2D grid's radio-opaque, or at least radiation-absorbing, walls. (e.g., lighter regions of FIG. 24A). In one embodiment, the radio-opaque, or at least radiation-absorbing, walls include a material including, but is not limited to, tantalum, tungsten or lead. In other words, a 2D grid acts as spatial modulator of x-ray flux, having specific regions of high or low intensity.

Dual energy CT techniques, such as material decomposition and virtual monoenergetic imaging, can play a role in mitigating such shortcomings of CBCT imaging. However, dual energy imaging in flat panel detector (FPD) based CBCT systems faces major challenges: since image acquisition rates of FPDs is a factor of 30-60 slower than conventional CT detectors, consistency of CT numbers needed for dual energy processing cannot be achieved in the presence of organ motion. One current dual energy method, projection domain, has proved challenging to implement with FPDs. This is because high and low energy projections cannot be acquired at similar source-detector positions. Additionally, a sufficient number of dual energy projections may not be acquired due to slow image acquisition, which may lead to under-sampling problems. To address these problems, one embodiment of the present invention contemplates a photon counting and energy resolving detector that is needed in CBCT imaging. In contrast to FPDs, photon counting detectors acquire high/low energy projections simultaneously and thereby eliminates organ motion in such projection pairs. Hence, dual energy CBCT can be enabled via implementation of projection domain dual energy processing methods.

In one embodiment, the present invention contemplates a photon counting detector that improves low contrast resolution. Although it is not necessary to understand the mechanism of an invention, it is believed that low contrast resolution improvement is due to an immunity to electronic noise and/or higher x-ray detection efficiency than FPDs. A further advantage is that photon counting detectors negate a need for rapid x-ray tube voltage-switching, where adequate dose allocation and spectral separation between in high/low energy images can be challenging to achieve.

The data presented herein demonstrate that the contemplated 2D antiscatter grid and aft fluence modulation method have overcome two major roadblocks known in the art. First, a "scattered radiation" intensity can exceed a primary intensity by a factor of 5 to 8, which severely biases the counts in high/low energy bins and makes dual energy imaging unfeasible. Second, a "limited count rate" (e.g., a "pulse pile-up" effect) is a major limitation of photon counting detectors, where the quantity and energy of x-rays cannot be accurately resolved at high x-ray fluence imaging conditions.

In one embodiment, the present invention contemplates devices and methods that overcome the above discussed problem of "scattered radiation" when using photon counting detectors. As detailed above, the present invention contemplates a two-dimensional antiscatter grid comprising a grid architecture that fundamentally differs with respect to radiographic 1D antiscatter grids. Although it is not necessary to understand the mechanism of an invention, it is believed that a 2D ASG as contemplated herein provides superior scatter suppression characteristics when compared to conventional radiographic grids and conventional scatter correction methods.

In one embodiment, the present invention contemplates devices and methods that overcome the above discussed problem of "limited count rate" when using photon counting detections. In one embodiment, the present invention contemplates a method comprising an aft fluence modulation. Although it is not necessary to understand the mechanism of an invention, it is believed that an aft fluence modulation utilizes a septal shadow of the 2D ASG where detector pixels underneath a grid's septa are exposed to significantly lower x-ray fluence than adjacent pixels in the center of 2D grid's cells.

Figure 25:
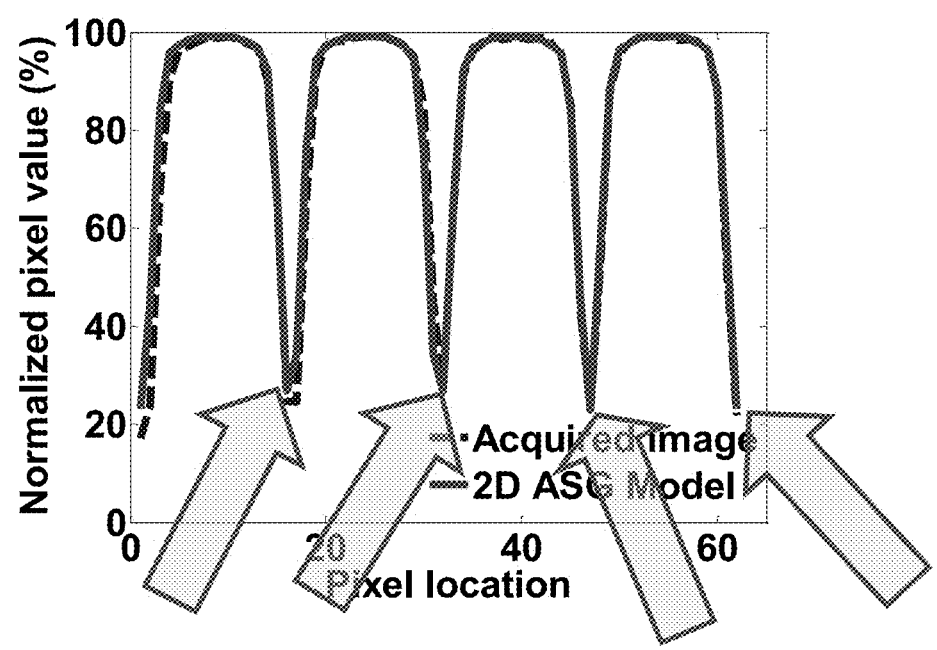
FIG. 25 illustrates one embodiment of aft fluence modulation regions (yellow arrows) resulting from pixels within the septal shadow of a 2D ASG grid.

Although it is not necessary to understand the mechanism of an invention, it is believed that in one embodiment, a 2D ASG grid is configured as an x-ray flux modulator. In one embodiment, a plurality of detector pixels are configured underneath a septal shadow such that the incident flux is reduced and x-rays can be accurately counted at each specific pixel. See, FIG. 25 (yellow arrows). Furthermore, X-ray counts in other pixels (i.e. pixels in the center of the holes) can be corrected by using the accurate count information in pixels underneath the grid's footprint or septal shadow.

Hence, an improved count accuracy and energy information may be extracted from pixels within the septal shadow. In one embodiment, the improved count accuracy and energy information is processed to correct high fluence region pixels that are biased by the "pulse pile-up" effect. Besides improving count rate capability, it is believed that septal shadows of a 2D ASG as contemplated herein can also reduce charge sharing among neighboring pixels, a known source of energy resolution degradation in photon counting detectors.

While various fluence modulation methods were previously proposed, all were based on pre-patient attenuators, such as dynamic bow tie filters. However, dynamic filters require a predictive algorithm and prior patient information to determine a patient specific modulation pattern, and can be electromechanically complex to achieve the desired fluence modulation. The presently disclosed configuration of pixels within the septal shadow of a 2D ASG as contemplated herein support an aft fluence modulation method that is not predictable from known dynamic pre-patient attenuators as a stationary 2D ASG is mechanically simple and prior patient knowledge is not required.

In one embodiment, the present invention contemplates a 2D ASG comprising a photon-counting detector wherein a plurality of pixels are within a septal shadow of the 2D ASG. In one embodiment, the septal shadow reduces x-ray scatter intensity. In one embodiment, the septal shadow reduces spatial variation in x-ray fluence. In one embodiment, the pixels within the septal shadow improve energy resolution performance. The data provided herein experimentally validated aft fluence modulation and characterized an improvement in count rate and energy resolution performance. Also evaluated are fluence conditions observed in clinical CBCT imaging.

The data provided herein will experimentally evaluate scatter reduction effects provided by 2D ASG. These data will be fabricated on 2D ASG prototypes and integrated with a photon counting detector.

Photon Counting Detectors

Figure 26:
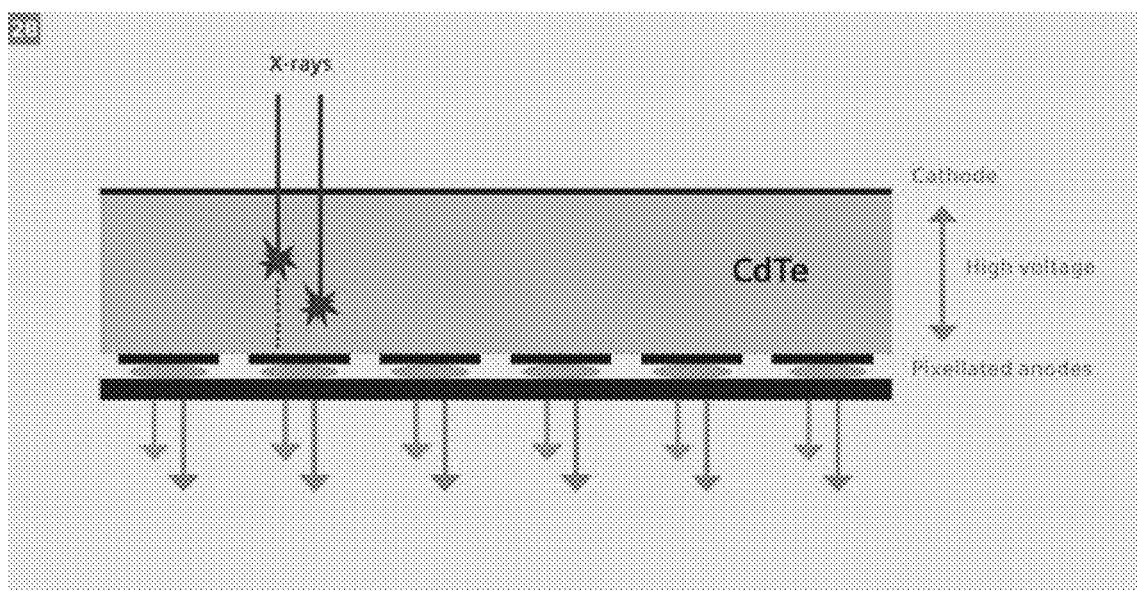
FIG. 26 presents one embodiment of a photon counting detector.

In one embodiment, the present invention contemplates an x-ray device comprising a 2D antiscatter grid and a hybrid flat panel detector, wherein the detector comprises a plurality of photon counting detectors. In one embodiment, the photon counting detector comprises a substrate (e.g., a cadmium telluride substrate) positioned between a cathode plate and an anode plate. In one embodiment, the anode plate comprises a plurality of pixels. Although it is not necessary to understand the mechanism of an invention a photon (e.g., an x-ray photon) impinging upon the substrate is detected by a pixel, such that it emits signal proportional to the energy of each photon (blue arrow). See, FIG. 26. In one embodiment, the photon counting detectors are positioned below a radio-opaque, or at least radiation-absorbing, area of the 2D ASG.

Current CBCT systems based on flat panel detectors (FPD) exhibit a poor low contrast visualization and lack CT number accuracy, which constitutes a barrier to implementation of treatment strategies in radiation therapy. When compared to MDCT detectors, amorphous silicon FPDs have significantly higher electronic noise, lower quantum efficiency, and lower digitization range [1]. These problems cumulatively contribute to degradation of low contrast object visualization in CBCT images [2]. One drawback of FPD is a relatively low projection acquisition rate (15-40 projections/sec) as compared to MDCT (2000-3000 projections per sec) [3]. Lower frame rates, combined with the safety-mandated slow gantry rotation speeds of linac gantries (60 secs per rotation) result in the presence of organ motion in CBCT images, which in turn prevents implementation of dual-energy CT (DECT) techniques. Among clinically available DECT acquisition techniques, only rapid kVp switching would be potentially applicable to FPD based CBCT [4, 5]. In this method, the tube voltage is switched between high and low kVp values (e.g. 80 and 140 kVp) to acquire high and low energy projections at a periodicity corresponding to the frame rate of the detector. However, due to the limitations of FPDs described above, low/high energy projections cannot be acquired fast enough, or at sufficiently similar gantry angles. As a result, dual energy processing may not be directly performed on low/high energy projections pairs, which has been reported to require pairs to be acquired at the same gantry, or source/detector position [4].

A potential alternative to DECT acquisition techniques is dual energy processing in the image domain (i.e. after the reconstruction of high and low energy CBCT images). However, in the clinical context of CBCT, this is complicated by organ motion. In addition to severely reducing CT number accuracy, organ motion may introduce pronounced motion artifacts in high and low energy reconstructions, which prevents accurate estimates of monoenergetic or material-specific CBCT images.

In one embodiment, the present invention contemplates a hybrid flat panel detector comprising a plurality of photon counting detectors. Although it is not necessary to understand the mechanism of an invention, it is believed that photon counting detectors de-couple dual-energy processing from organ motion artifact. For example, it is believed that each photon counting detector projection contains both high and low energy images acquired at the same time [6]. Hence, each projection is free of organ motion, and dual energy processing can be performed directly on each projection individually. Subsequently, material specific or monoenergetic CBCT images can be reconstructed. While effects of organ motion is present in a material-specific CBCT image (due to the slow rotation of CBCT gantry) it will not interfere with projection domain dual energy processing.

Photon counting detector based CBCT systems face two major barriers:
 a) High scattered radiation intensity is an inherent problem of CBCT [2, 9]. Scatter contaminates the energy spectrum such that dual energy processing may not be performed accurately. As such, it is currently believed that DE CBCT research is limited to imaging of small objects, such as extremities or small animals, where scatter intensity is relatively lower [5, 10, 11]; and
 b) CBCT count rate limitation due to pulse pile-up. Pulse pile-up occurs when two or more x-ray events are absorbed in the x-ray sensor with a very small temporal separation, and hence register as a single x-ray event leading to x-ray counts being underestimated [6, 12]. The incident x-ray fluence in CBCT can be as high as $10^7$-$10^8$ x-rays per second/mm$^2$. Such incident count rates are still high enough to cause considerable pile-up and count rate losses.

Figure 27:
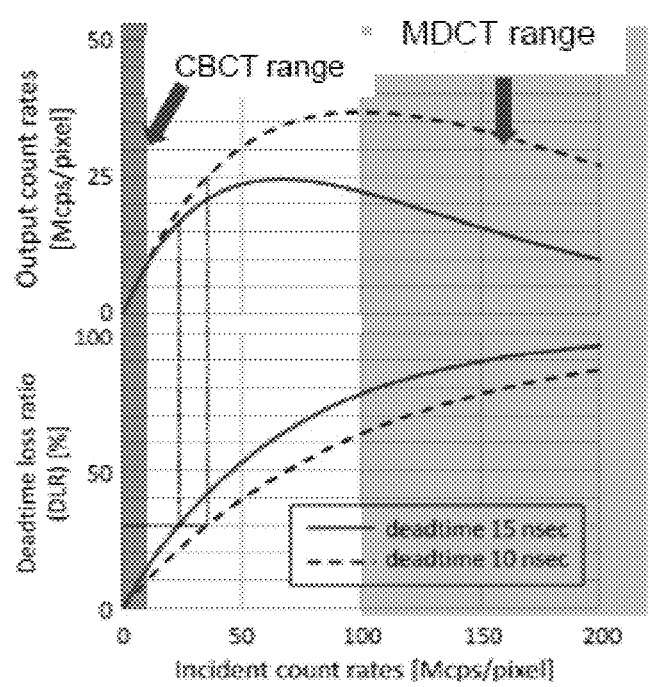
FIG. 27 presents exemplary data of the range of maximum incident count rates in MDCT and CBCT and the corresponding output count rates. Incident count rates in MDCT (red region) is in the range of $10^8$-$10^9$ per sec/mm$^2$, whereas count rates in CBCT (green region) is $10^7$ per sec/mm$^2$ or less (each pixel is assumed be 1 mm$^2$ in the graph). [6]

In photon counting MDCT, pulse pile up is particularly a big problem as maximum fluence incident on the detector can be in the order of 108-109 counts per second/mm2 and, as a result, x-ray counts are under-measured due to pulse pile-up. See, FIG. 27. In CBCT, the incident x-ray fluence is much lower than MDCT, about 107 counts per second/mm2. It is believed that this low fluence may be due to a factor of 30 to 100 lower tube currents and a consequent a slower gantry rotation time (e.g., 60 seconds in CBCT vs 0.5 seconds in MDCT). However, such incident count rates are still high enough to cause considerable pile-up and count rate losses.

In one embodiment, the present invention contemplates both devices and methods to solve the CBCT problems regarding both the scattered radiation and limited count rate problems for photon counting detectors. In one embodiment, these devices and methods comprise photon counting detectors. In one embodiment, these devices and method comprise dual energy techniques. In recent years, many clinical studies have been published on improving soft tissue visualization by synthesizing low keV monoenergetic images, and the benefits of material decomposition, all enabled by DECT [13-16]. It is currently believed that translation of DECT techniques to a CBCT domain requires overcoming the above defined CBCT image quality barriers. In one embodiment, the present invention contemplates a photon counting method based upon dual energy processing.

In some embodiments, a CBCT photon counting approach has advantages over energy integrating CBCT; i) as x-rays are counted, photon counting eliminates a readout noise problem associated with FPDs; ii) an X-ray counting approach provides much higher dynamic range than energy integrating FPDs; iii) X-rays are directly converted to electrical charge, i.e. scintillators are eliminated, and thus, sensor thickness can be increased to 2 mm or more to improve quantum efficiency above 90%, without sacrificing spatial resolution [6].

Figures 28A, 28B:
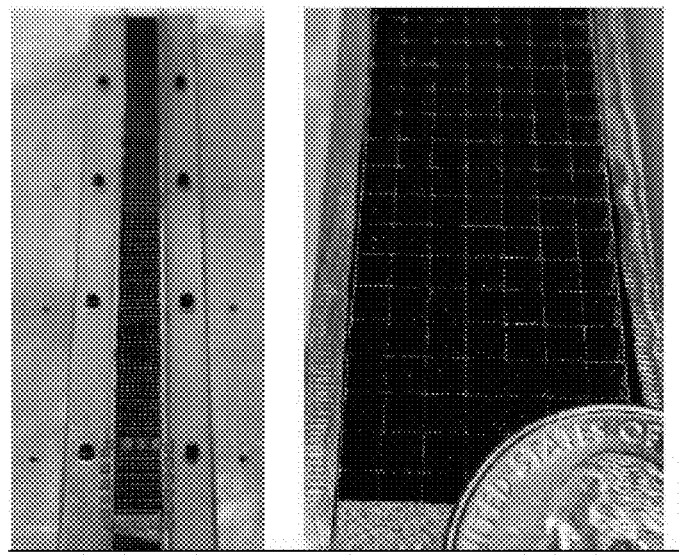
FIGS. 28A and 28B present one embodiment of a 2D ASG.

In one embodiment, the present invention contemplates a 2D ASG as a two-dimensional array of through-holes separated by radio-opaque, or at least radiation-absorbing, septa. See, FIG. 1. In one embodiment, each through-hole is aligned, or focused, towards an x-ray source. Moreover, the 2D ASG contemplated herein lacks an interseptal spacer as an optimized grid design that provides a high primary transmission. In one embodiment, the present invention contemplates a 2D ASG comprising a CBCT flat panel detector. FIG. 28A and FIG. 28B. Although it is not necessary to understand the mechanism of an invention, it is believed that a 2D ASG reduces scatter contamination to levels that has not been achievable with any existing CBCT scatter mitigation approaches. It is further believed that a two-dimensional array of septa as presented herein is a more efficient configuration to stop radiation scatter than any one-dimensional septa array currently used in CBCT radiographic imaging ASGs.

Figure 29:
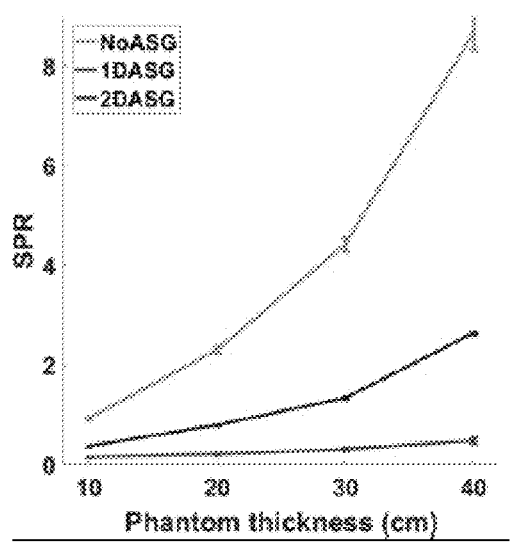
FIG. 29 presents exemplary data of a scattered radiation to primary radiation ratio (SPR) as a function of slab phantom thickness. Note: Radiographic 1D ASG and 2D ASG have SPR ratios of 10 and 8, respectively. [17].
Figure 30A:
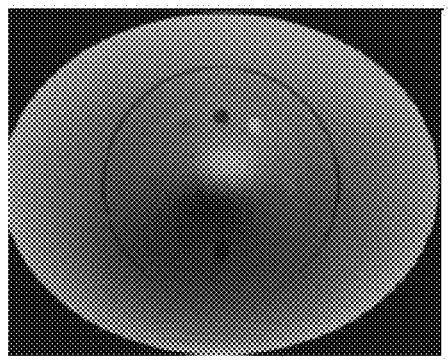
FIGS. 30A, 30B and 30C present representative images showing improved CBCT image quality with 2D ASG. Images were acquired using a linac mounted CBCT system, and hence, the effect of gantry sag were included. Elliptical phantom mimics human torso dimensions (30 cm×38 cm).
Figure 30B:
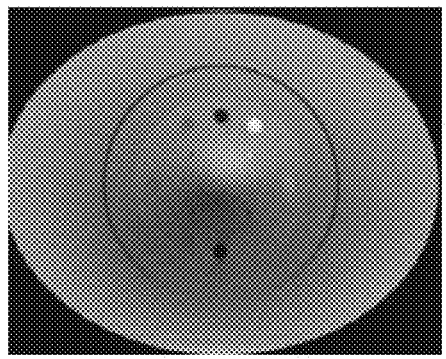
Figure 30C:
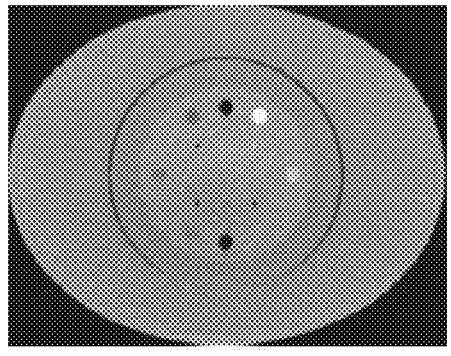

It has been reported that a 2D ASG with a grid ratio of 8 provided a factor of 3 to 6 lower SPR than a radiographic 1D ASG with a grid ratio of 10. FIGS. 29, and [17]. This is further evidenced by an improved quality of CBCT images when using a 2D ASG with a hybrid flat panel photon counting detector versus a 1D ASG with radiation gathering detectors and a radiation gathering detector without an ASG. FIGS. 30A, 30B and 30C.

A reduced scatter fluence by a 2D ASG is also expected to reduce the photon "pulse pile-up" problem. A scattered radiation to primary radiation ratio measured using a 30 cm phantom thickness exceeds four (4), which indicates that scattered radiation increases x-ray intensity incident on the detector by a factor of 4. Since scattered x-rays increase the x-ray fluence incident on a detector, this phenomenon contributes to a pulse-pile up problem. FIG. 29. However, with a 2D ASG as contemplated herein, a scattered radiation-to-primary radiation ratio is reduced to 0.31. Consequently, a 2D ASG configuration leads to an almost factor of four reduction in scattered radiation intensity incident on a detector, and hence, reduces photon pulse pile-up. With radiographic 1D ASGs, this effect will be less pronounced as they transmit high fraction of scattered x-rays. Software based scatter correction strategies cannot reduce the scatter induced pulse pile-up, as scatter correction is performed after the detection of scattered x-rays by the x-ray sensor.

With respect to a 1D ASG, scatter suppression efficiency of 2D ASG was particularly better at higher scatter intensity environments; as the angular distribution of radiation scatter is larger for thicker objects, septa configured in two dimensions is more efficient in stopping scattered x-rays than one-dimensional a septa configuration.

As mentioned above, a 2D ASG provides a higher primary radiation transmission than 1D ASGs. It is believed that the higher primary radiation transmission is due to: i) an absence of interseptal spacers; and ii) a larger grid pitch (2.9 mm). In one embodiment, a 2D ASG as contemplated herein comprises an 85% primary transmission (averaged over the entire area of 2D ASG), whereas a conventional 1D ASG with fiber spacers has a 71% primary transmission.

The implementation of 2D ASGs in the context of photon counting detectors and dual energy imaging is believed to have advantages over 1D ASGs and 2D ASGs configures with energy gathering detectors. These advantages include, but are not limited to: a) a reduction of energy spectrum contamination; b) a reduction in scattered radiation fluence contamination that is characteristic of x-rays emitted from tungsten grid septa; c) a reduction in radiation backscatter from photon-counting detector on an incident x-ray energy spectrum; and d) preferred grid septa positioning with respect to photon counting detector pixel positions to optimally process x-ray fluence and energy spectrum.

In one embodiment, the present invention contemplates an aft fluence modulation method comprising a 2D ASG and a photon counting detector for improving radiation count rate and energy resolution. In one embodiment, a 2D ASG footprint creates a plurality of septal shadows. In one embodiment, a 2D ASG comprises a plurality of photon counting detectors comprising pixels are located underneath 2D ASG vertical septa. As such, these photon counting detector pixels are exposed to a significantly lower fluence than pixels in the center of the 2D ASG through-holes. See, FIG. 24 and FIG. 25. Thus, pixels in septal shadows are less likely to be affected by the pulse-pile up problem. In high fluence regions of a projection, such as skin-air boundaries, pixels in the center of through-holes exhibit photon pulse pile-up, and they will be excluded from the projection image. Image signal in these locations may be estimated by image signals from septal shadows surrounding that location. As the grid pitch will be in the order of 1-3 mm, we believe that interpolation may be a feasible approach to estimate image signal in the center of the through-holes by using image signal in surrounding septal shadows.

Figure 31A:
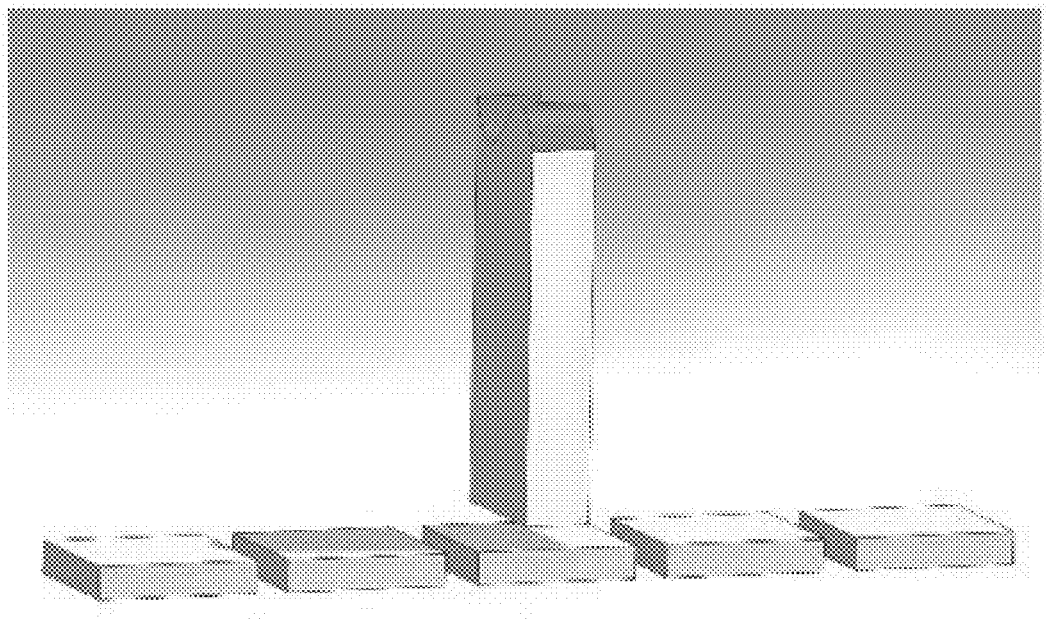
FIGS. 31A, 31B and 31C present two septa embodiments configured to perform an aft fluence modulation method.
Figure 31B:
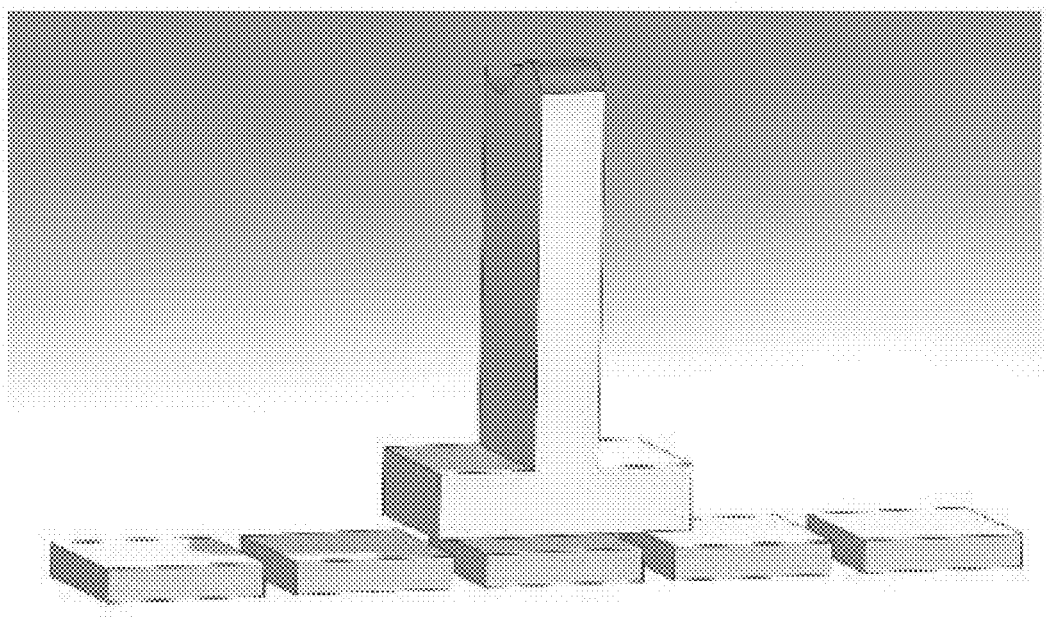
Figure 31C:
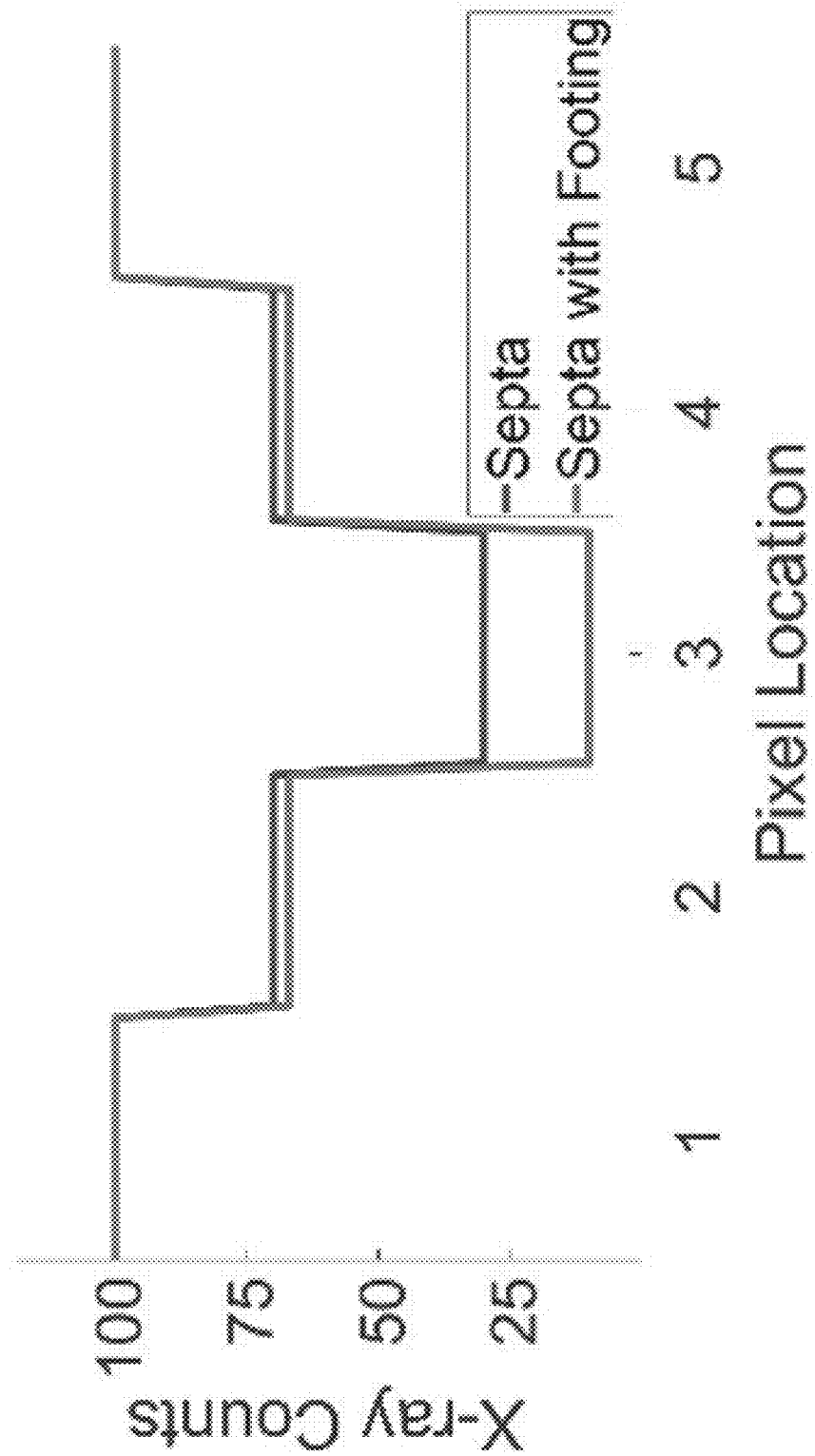

As the above-described method will be used only in high fluence regions that exhibit photon pulse pile-up. However, to solve this problem also involves locating high fluence regions within a projection. In one embodiment, an aft fluence method comprises detecting regions exhibiting photon pulse-pile up. FIGS. 31A, 31B, and 31C. For example, SPR ratio of counts in pixel 5 (high fluence region) as compared to pixel 3 (low fluence region) is not constant, i.e. will change as a function of incident fluence. The count ratio of pixel 5 to pixel 3 at low incident fluences is expected to be higher than the ratio at high fluences. This is due to the fact that pixel 5 will exhibit more count loss, or have a relatively lower counts, due to pulse pile-up. The count ratio between pixels 5 and 3 can be established for varying fluence levels, and this calibration data can be utilized as a "pulse pile-up detector" during CBCT scans.

In one embodiment, the present invention contemplates an aft fluence grid configuration. For example, as both grid geometry and pixel dimensions play a role in fluence modulation in septal shadows, various grid septa configurations are contemplated. FIGS. 31A and 31B. In one embodiment, septal thickness is increased to further reduce fluence within septal shadows. This way, a larger portion of each pixel is shadowed by thicker septa, where a small portion pixel surface is exposed to incident x-rays. However, unobstructed areas of pixels are located on or near the edges of pixels, and a charge cloud created by x-ray absorption in this region is more likely to spread onto neighboring pixels, which may lead to spectral degradation due to charge sharing. A more optimal solution to reduce fluence in septal shadows is to employ grid septa with a footing. FIG. 31B. In one embodiment a footing has a height of approximately between 0.3 to 2 mm. Although it is not necessary to understand the mechanism of an invention and it is believed that the footer attenuates the radiation beam, rather than fully obstructing x-rays. By using a septal footing, fluence reduction can be better controlled, and a large portion of the pixel surface may be exposed to incident x-rays, potentially reducing the charge sharing problem. With this approach, fluence within septal shadows can be reduced by an order of magnitude lower when compared to fluence at the center of septal through-holes.

Additive manufacturing methods are used to create grid geometries and septa configurations. Powder bed laser melting (PBLM) method is used to fabricate our 2D ASG prototypes. PBLM for tungsten is compatible with an additive manufacturing process, as challenges due to the high melting point of tungsten have been addressed in recent years. In PBLM, tungsten powder is spread over a built platform, and a high power laser beam traces and melts the tungsten powder based on the CAD design. The grid is built layer by layer, by lowering the built platform, adding a new layer of tungsten powder, and repeating the laser tracing process. Finished products are accurate in dimensions within 20 microns, and minimum septal thickness of 100 microns has been achieved. PBLM provides large design freedom, which enables fabrication of complex grid geometries, such as focusing of individual through-holes, spatially varying grid pitch and height. PBLM may also enable fabrication of our proposed septa with footing for Aft Fluence Modulation. PBLM is a scalable manufacturing process, which is suitable for both rapid prototyping and serial production of 2D ASGs.

To reduce high x-ray fluence, dynamic beam attenuators were proposed and investigated by various research groups in the context of MDCT [18, 19]. Such attenuators are placed between the x-ray tube and the patient, where fluence is modulated spatially and temporally, to reduce fluence in less attenuating regions of the patient. Some examples of this approach are dynamic bow tie filters and beam-attenuating rods that move in and out of x-ray beam.

Implementation of such techniques may have major limitations, particularly in the context of CBCT. First, dynamic beam filters are aimed for fan beam CT geometry, where fluence modulation is needed in one dimension. In contrast to MDCT, fluence modulation in CBCT is needed in two dimensions, and the desired fluence pattern may not be achieved by a linear array of beam attenuators. For example, in thorax, high fluence regions due to lungs are surrounded by low fluence regions due to mediastinum and chest wall. Such high fluence "islands" are challenging to compensate using a linear array of dynamic beam attenuators. Second, determination of modulation pattern requires prior knowledge about the patient attenuation characteristics. If a patient's prior CT scan is employed for this purpose, differences in patient position and geometry can lead to regions with under-, over-modulation. Third, since dynamic beam filters are placed close to the x-ray tube, any filter positioning errors will be magnified in the detector plane. The effects of gantry sag and associated effects on positioning errors are magnified as well. The mismatch between the expected and actual position of attenuators will lead to high gradient spikes and dips in fluence, which may cause severe artifacts in images. Lastly, proposed dynamic attenuators are electromechanically complex. Fabrication of such devices remains to be an area to be investigated.

In the presently contemplated Aft Fluence Modulation method, the electromechanical complexity of dynamic attenuators is not present, as fluence is always modulated, in two dimensions, by the 2D grid pattern attached to the detector. The methods described herein do not require prior information about patient attenuation characteristics either. Since the 2D ASG is placed close the detector plane, any adverse effects of gantry sag or flex are much less pronounced with respect to pre-patient beam attenuators.

EXAMPLES

The following examples are provided in order to demonstrate and further illustrate certain preferred embodiments and aspects of the present invention and are not to be construed as limiting the scope thereof.

Example 1

Figure 20:
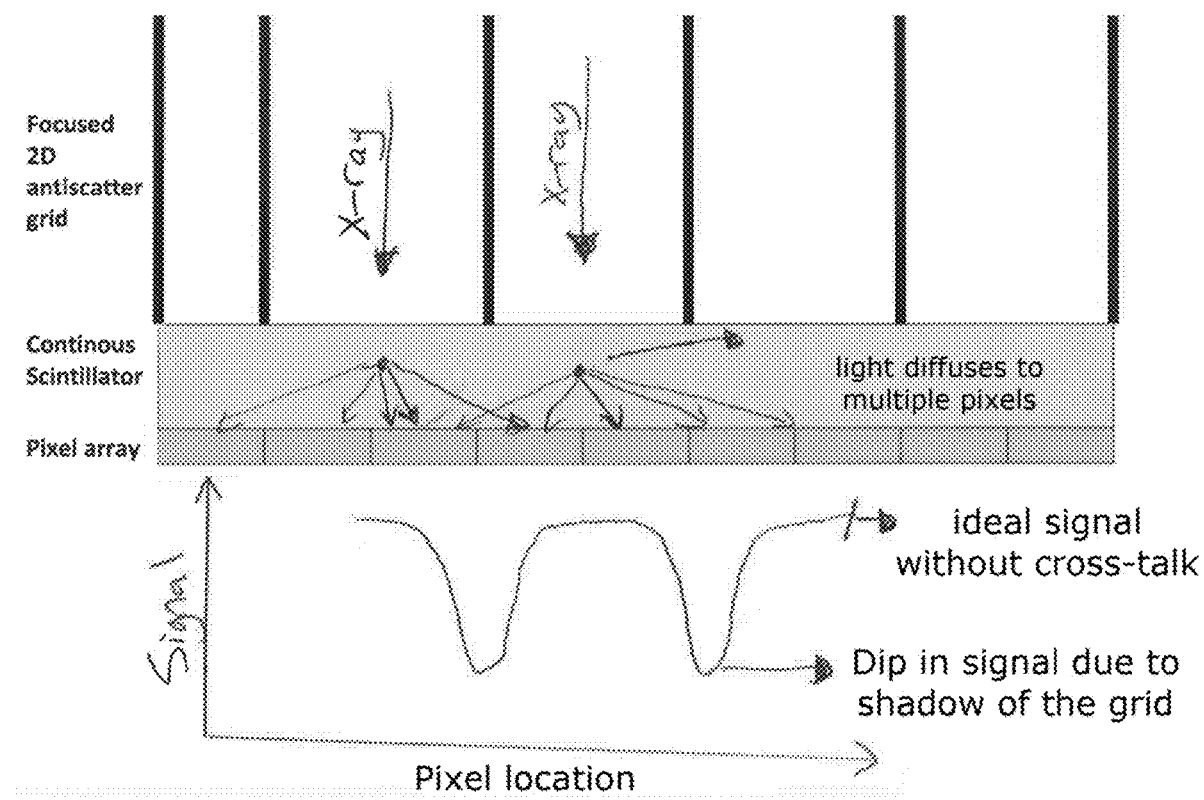
FIG. 20 shows the diffusion of x-rays with a focused 2D antiscatter grid with a continuous scintillator and pixel array. This shows that there can be a dip in signal due to shadow of the grid, depending on pixel location.
Figure 21:
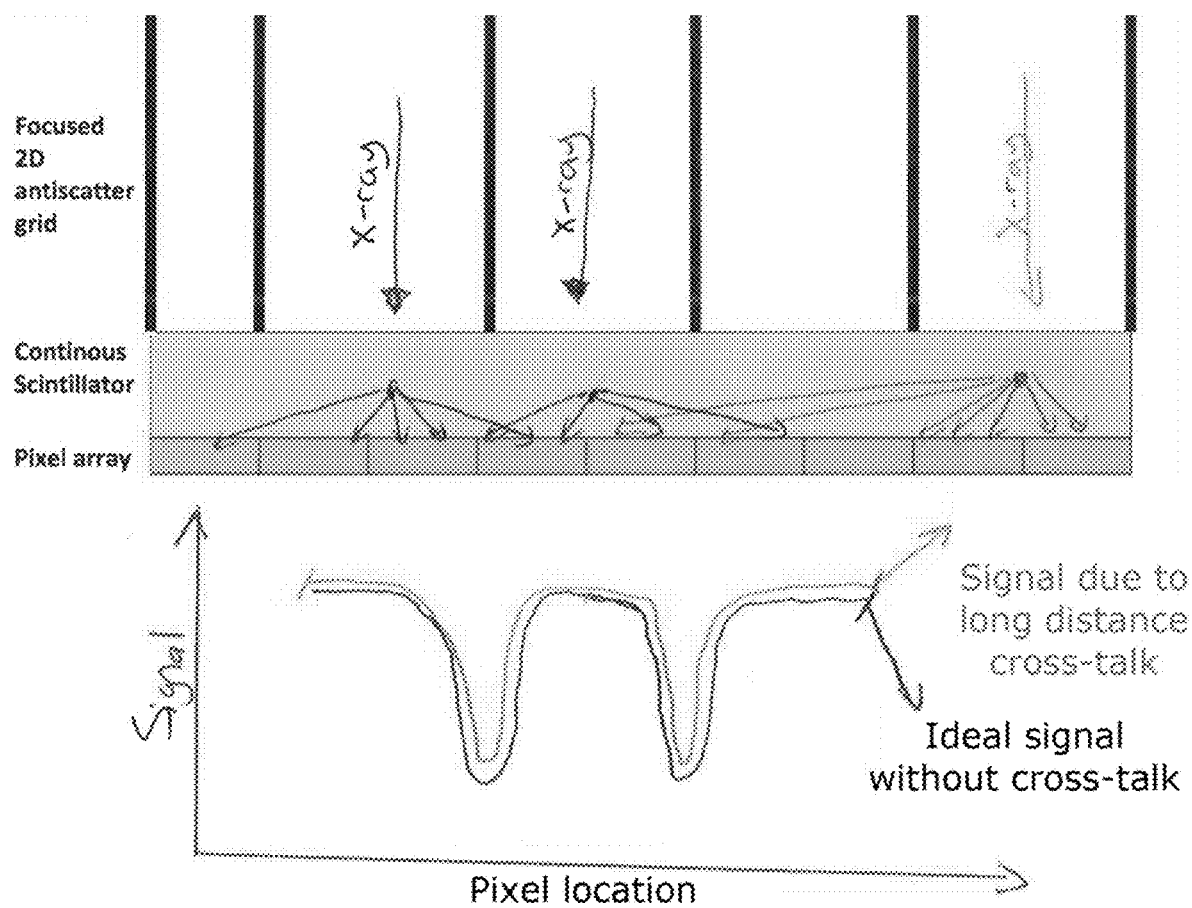
FIG. 21 shows the diffusion of x-rays with a focused 2D antiscatter grid with a continuous scintillator and pixel array. This shows that there can be signal interference due to long-distance cross-talk.

In one embodiment, the invention relates to a two-dimensional antiscatter grid, wherein the two-dimensional antiscatter grid is installed on top of a flat panel detector protective cover. In one embodiment, the two-dimensional antiscatter grid is described in FIG. 20, FIG. 21, and FIG. 22. In one embodiment, some basic x-ray transmission characteristics of the two-dimensional antiscatter grid are described in Example 2. In one embodiment, the hybrid flat panel detector is described in Example 3 & Example 4. In one embodiment, the two-dimensional antiscatter grid unique qualities and grid parameters are described in Example 5 & Example 6. In one embodiment, a method to correct scatter using a 2D antiscatter grid is described in Example 7. In one embodiment, an illustration of a pixelated scintillator is found in FIG. 20, FIG. 21, and FIG. 22. A more expansive description of one embodiment of the current invention is described in Example 2. Previous explorations of antiscatter grid prototypes are described by Altunbas [1, 71].

A. A Flat Panel Detector that is "Directly" Integrated with 2D ASG, Referred as "Hybrid" FPD While 2D ASG's purpose is to block scattered (or contaminant) x-rays, it also partially blocks primary x-rays (i.e. desired x-rays that form the x-ray image). 2D ASG's septa create a shadow that appears as a grid pattern in FPD images. This shadow is due to the lower x-ray intensity reaching the FPD, as the 2D ASG's septa partially blocks the primary x-rays. 2D ASG's shadow, i.e. variation in primary x-ray intensity, creates two major problems from image quality point of view: 1) The 2D ASG's shadow will cause severe artifacts in images, which makes the use of 2D ASG unfeasible. Therefore, the shadow of the 2D ASG must be corrected by means of software or hardware methods. 2) Even if the 2D ASG's shadow is corrected, 2D ASG continue to block primary x-rays, and reduced intensity of primary x-rays will reduce image quality: Lower the intensity of primary x-rays reaching the FPD, the noisier the image gets. This problem can be compensated by increasing the x-ray dose to the patient; this is not, however, a preferred solution. 3) When 2D ASG/FPD combo is employed in a CBCT system, the position of 2D ASG's shadow will shift slightly in relation to the pixels in the FPD, as the CBCT gantry rotates around the patient during image acquisition. As a result, grid shadow correction methods may not work at all, or may correct grid shadows sub optimally.

The shift in grid shadow position is due to the CBCT gantry flex, which is caused by forces exerted by gravity on the gantry during gantry rotation. As a result, the x-ray source will change position with respect to 2DASG/FPD combo, and the 2D ASG's shadow will project to a slightly different location. If the 2D ASG's shadow shifts during image acquisition, correction of the shadow may become quite challenging.

Possible Solutions:

A. 2D ASG's shadow should be minimized as much as possible. To achieve this, it is possible to directly place the 2D ASG on the scintillator/pixel array in the FPD. The shadow size is a function of the "distance" between the top surface of the 2D ASG and the FPD pixel array. Smaller this distance, smaller the shadow gets. Currently, standard one-dimensional ASGs and FPDs are manufactured independently, and the 1D ASG is integrated on the protective cover of the FPD. Someone experienced in this Art is likely to follow the same approach to integrate a 2D ASG with a FPD. As described in Example 4, such an approach increases the distance between the top surface of the 2D ASG and the pixel array due to the air gap and protective cover of the FPD. As a result, 2D ASG's septa appear thicker in images than its physical thickness. For example, 0.1 mm thick septa can appear as thick as 0.24 mm in FPD images based on experiments.

If the 2D ASG is placed on the scintillator/pixel array, the distance between the top of the ASG and pixel array can be reduced by about 40% (the actual reduction depends on the properties of the FPD and 2d ASG).

One approach of the current invention also helps to reduce the change in 2D ASG's shadow position due to gantry flex. Smaller the distance between top of the 2D ASG and pixel array, smaller the shift in shadow gets. As a result, grid shadow correction may be more robust.

B. The 2D ASG's septa not be aligned with detector pixel array and the grid channel size is much larger than the detector pixel size. This way, 2D ASG blocks less primary x-rays, and hence, improve image quality (See Example 5 and Example 6 for more details). One of the current invention prototype 2D ASG demonstrates the benefits of this approach. In Example 5 and Example 6, it is shown that the presently disclosed 2D ASG provides 19% more primary x-ray intensity than a conventional 1D ASG.

This approach also brings a large flexibility to grid/detector design. Grid channel shapes do not need to be square, they can be hexagonal etc. (for example, hexagon shaped grid channels can produce smaller footprint than square shaped grid channels). Also channel width (or grid pitch) can be varied across the detector (for example, grid height can be kept the same channel width can be made smaller towards the central section of the detector where the scatter is highest. Channel widths can be made larger at the periphery of the detector, where the scatter is lower. Variable grid channel width can reduce the cost of the 2D ASG).

C. To help to correct the 2D ASG's shadow, the current invention utilizes pixelated scintillators rather than continuous scintillators in energy integrating FPDs. Pixel walls are aligned with the septa of the 2D ASG. As described in Example 5 and Example 6 and FIG. 22, this approach reduces the long-range cross talk within the scintillator, and thus, reduces the intensity variations in 2D ASG's shadow.

Reduced cross talk also improves the spatial resolution to some extent.

A Method to Estimate and Correct Scatter Intensity Transmitted Through 2D ASG.

Briefly, this method corrects the residual scatter intensity that was transmitted through the 2D ASG. The method exploits the properties of 2D ASG's shadow in FPD images, to estimate the residual scatter intensity. The details of the method are described in Example 7.

Besides correcting the residual scatter in images and improving image quality, this method relaxes the technical requirements on 2D ASG fabrication and its potential implications on image quality.

For example, a 2D ASG with a given channel width, can be fabricated with significantly less height; aspect ratio of grid channels, known as grid ratio, will be reduced which makes it technically less challenging and cheaper to fabricate. Moreover, lower grid ratio makes it easier to correct the grid shadows (i.e. the distance between the top of the ASG and pixel array reduced). While more residual scatter will reach the FPD due to lower grid ratio, it can be "corrected" using the proposed method in Example 7.

Example 2

Transmission Characteristics of a Two Dimensional Antiscatter Grid Prototype for CBCT [102]

Aim: High fraction of scattered radiation in CBCT imaging degrades CT number accuracy and visualization of low contrast objects. To suppress scatter in CBCT projections, a focused, two-dimensional antiscatter grid (2D ASG) prototype was developed. In this Example, the primary and scatter transmission characteristics of the 2D ASG prototype aimed for linac mounted, offset detector geometry CBCT systems in radiation therapy, are described and compared its performance to a conventional one-dimensional ASG (1D ASG).

Methods: The 2D ASG is an array through-holes separated by 0.1 mm septa that was fabricated from tungsten using additive manufacturing techniques. Through-holes' focusing geometry was designed for offset detector CBCT in Varian TrueBeam system. Two types of ASGs were evaluated: a) a conventional 1D ASG with a grid ratio of 10, b) the 2D ASG prototype with a grid ratio of 8.2. To assess the scatter suppression performance of both ASGs, Scatter-to-primary ratio (SPR) and scatter transmission fraction ($T_S$) were measured using the beam stop method. Scatter and primary intensities were modulated by varying the phantom thickness between 10 and 40 cm. Additionally, the effect of air gap and bow tie (BT) filter on SPR and $T_S$ were evaluated. Average primary transmission fraction ($T_P$) and pixel specific primary transmission were also measured for both ASGs. To assess the effect of transmission characteristics on projection image signal-to-noise ratio (SNR), SNR improvement factor was calculated.

Results: In comparison to 1D ASG, 2D ASG reduced SPRs by a factor of 3 to 6 across the range of phantom setups investigated. $T_S$ values for 1D and 2D ASGs were in the range of 21 to 29%, and 5 to 14%, respectively. 2D ASG continued to provide lower SPR and $T_S$ at increased air gap and with BT filter. $T_P$ of 1D and 2D ASGs were 70.6% and 84.7%, respectively. Due to the septal shadow of the 2D ASG, its pixel specific primary transmission values varied between 32.5% and 99.1%. With respect to 1D ASG, 2D ASG provided up to factor of 1.7 more improvement in SNR across the SPR range investigated.

Conclusions: When compared to a conventional 1D ASG, 2D ASG prototype provided noticeably lower SPR and $T_S$ values, indicating its superior scatter suppression performance. 2D ASG also provided 19% higher average primary transmission that was attributed to the absence of interseptal spacers and optimized grid geometry. The results indicate that the combined effect of lower scatter and higher primary transmission provided by 2D ASG may potentially translate into more accurate CT numbers and improved contrast resolution in CBCT images.

1. Introduction

High scattered radiation intensity is one of the major causes of image quality degradation in FPD based CBCT, which leads to loss of contrast resolution, reduced CT number accuracy, and scatter induced image artifacts [4]. Two major approaches, knows as scatter rejection and scatter correction methods, have been heavily investigated in the last decade to address this problem [5, 29, 36]. For scatter rejection purposes, ASGs developed for radiography and fluoroscopy have been employed in CBCT [27, 28, 39, 41, 42]. These ASGs consists of a one-dimensional array of radio-opaque, or at least radiation-absorbing, septa separated by aluminum or fiber spacers that support septa (such ASGs are referred as 1D ASG in the rest of the text).1D ASGs typically provide a factor of 2 to 5 reduction in SPR values, and subsequently improve CT number accuracy and reduce image artifacts. Moreover, bow tie filters were also employed in CBCT, and they were shown to reduce scatter fraction in sections of the object close to the CBCT isocenter [28, 72-75]. While such scatter suppression devices help to reduce relative scatter intensity, residual scatter reaching the FPD is still high enough to deteriorate CBCT image quality. Scatter correction methods, which refers to correcting the effects scatter after its detection by the image receptor, are often employed to correct the residual scatter [37, 38, 76-84]. Generally, both of these approaches have been used together in CBCT systems for radiation therapy. However, the improvement in image quality is not at the desired level to achieve highly accurate CT numbers or improved visualization of low contrast objects [21, 23, 65, 85].

To improve scatter suppression in CBCT, 2D ASGs may be viable alternative to 1D ASGs, since two-dimensional septa can potentially provide better scatter rejection performance than one-dimensional septa employed in 1D ASGs. With recent advances in advanced manufacturing methods, 2D ASGs were introduced for mammography [86], breast tomosynthesis [87], and MDCT [88]. These 2D ASGs were fabricated using lithographic techniques, and composed of copper (for mammography) or tungsten infused polymer (for tomosynthesis and MDCT) to achieve low septal thickness, high radio-opacity and geometric accuracy of the 2D grid. Moreover, due to the self-supporting structure of a 2D grid, interseptal spacers were eliminated in 2D ASGs, which may help to improve 2D ASGs' primary transmission properties.

To assess the feasibility of 2D ASGs in the context of CBCT imaging, a 2D ASG prototype was designed and fabricated to be employed in a linac mounted CBCT system. In contrast to 2D ASGs cited above, one embodiment of the current invention may be fabricated from pure tungsten using laser sintering based additive manufacturing methods. In this work, its scatter and primary transmission characteristics under various imaging conditions were evaluated, and compared it with a standard 1D ASG employed in the clinical CBCT system. Additionally, the impact of transmission characteristics on the SNR improvement in projection images was assessed.

2. Materials and Methods

2.1. 2D ASG Prototype

Figure 2:
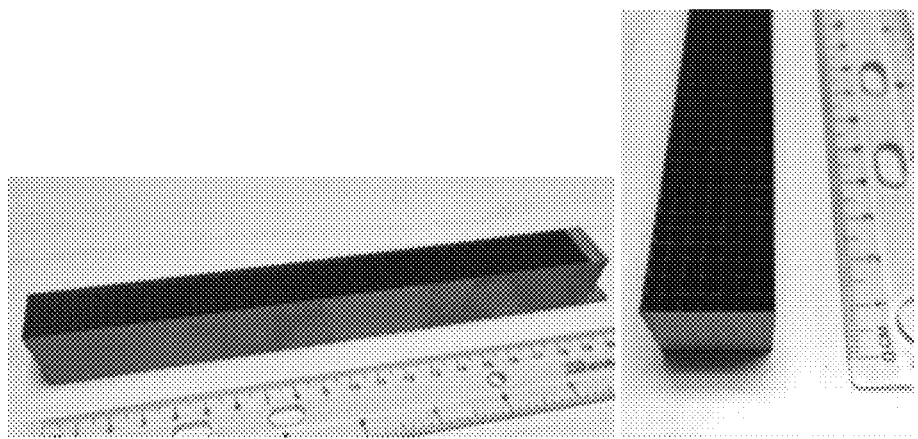
FIG. 2 shows two pictures of a 2×20 cm2 2D antiscatter grid (ASG) module. Each grid hole has a unique slant, or angle, such that they are aligned towards the focal spot in half-fan CBCT geometry.

The 2D ASG prototype was composed of a rectangular array of square, through-holes, separated by tungsten septa (FIG. 2). To minimize the shadow of septa in projection images, through-holes were aligned, or focused, in two dimensions towards the x-ray source, and focusing geometry was matched to TrueBeam's "half-fan" CBCT geometry (Varian Medical Systems, Palo Alto, CA). It was composed of two, 2 cm wide by 20 cm long modules, and they were glued together to achieve 2×40 cm² coverage on the FPD plane. 2D ASG has a grid pitch of 2.91 mm, grid height of 23 mm, and a septal thickness of 0.1 mm, resulting in a grid ratio of 8.2 (i.e. the ratio of grid height to through-hole width). 2D ASG was fabricated using the Powder Bed Laser Melting (PBLM) process, and it was manufactured by Smit Röntgen (Best, Netherlands). PBLM process is similar to direct metal laser sintering, where a computer guided laser beam driven by the CAD model of the ASG traces and melts the tungsten powder that is placed on a built platform. The grid structure is built on a layer-by-layer basis by lowering the platform, adding a new layer of tungsten powder, and repeating the laser melting process.

2.2 Experimental Setup and Data Acquisition

Figure 3:
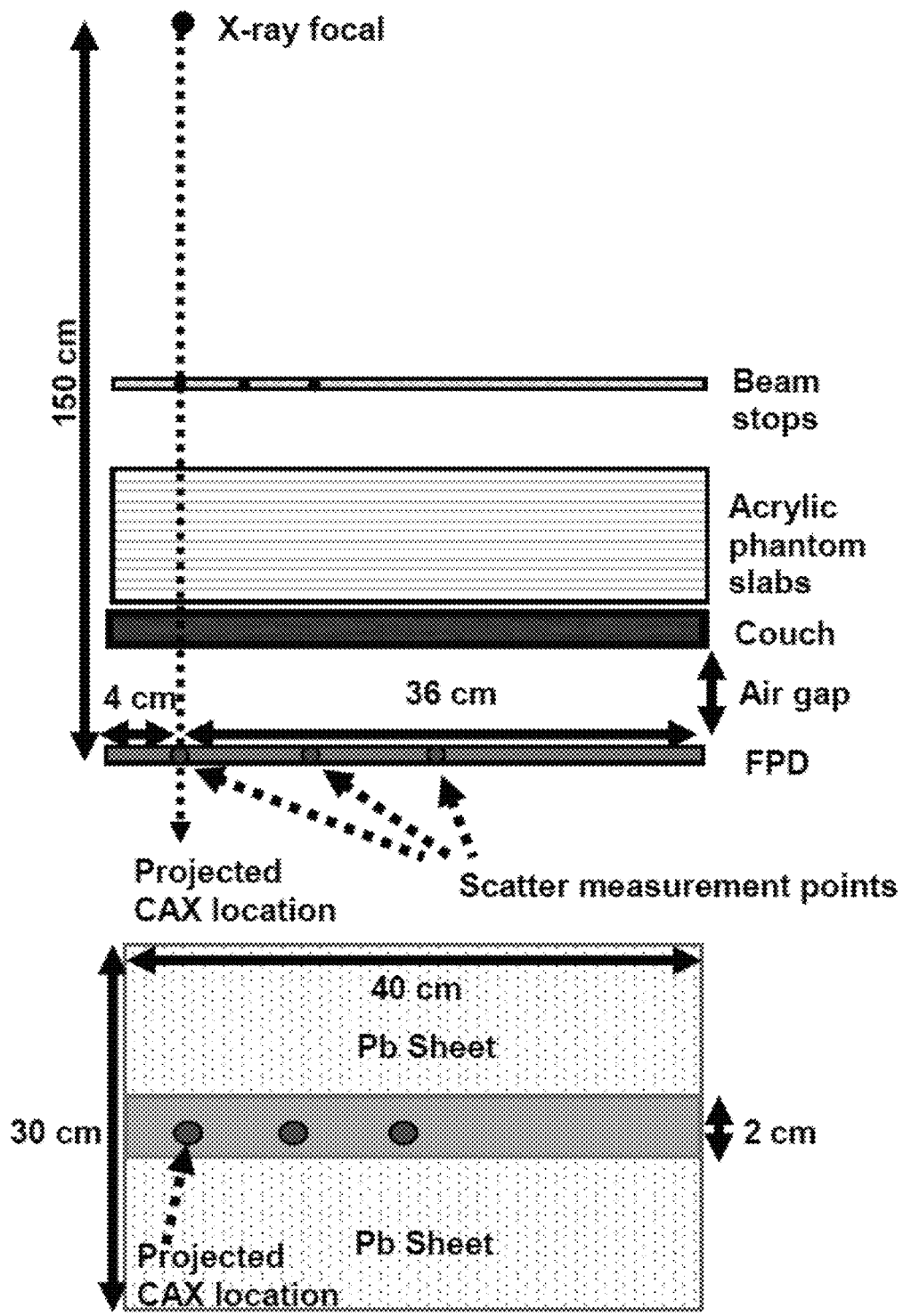
FIG. 3 shows (Top) Side view of the experimental setup. Red circles correspond to measurement points, and they are located at CAX, 10 cm, and 20 cm off-axis from CAX at detector plane. (Bottom) Beam eye view of the FPD. 2×40 cm2 wide "measurement area" of the FPD is shown in gray. Rest of the FPD was covered with Pb sheet.

Experiments were performed using the CBCT system in a Varian TrueBeam STx linac. The CBCT system utilizes a PaxScan 4030CB FPD (Varian Medical Systems, Palo Alto, CA) with an imaging area of 40×30 cm², and a GS-1542 x-ray tube (Varian Medical Systems, Palo Alto, CA). In all experiments, half-fan CBCT geometry (also known as offset detector geometry) was utilized (FIG. 3), where the center of FPD was shifted by 16 cm in the transverse direction with respect to imaging isocenter. Thus, the projected location of the beam's central axis (CAX) was 4 cm from the short edge of the FPD as indicated in FIG. 3. Projected location of CAX was simply referred as "CAX" in the rest of the text. In all experiments, central 2×40 cm² section of the FPD was exposed to x-rays, and this section was referred as "measurement area" in the rest of text. The remainder of the FPD was covered with 3.2 mm thick lead sheet that blocked 99.7% of the primary beam. TrueBeam CBCT system comes with a focused, radiographic ASG (1D ASG), that was composed of a 1D array of fiber interspaced lead septa. It has a grid ratio of 10, line rate of 60 l/cm, and septal thickness of 0.036 mm. In experiments with the 2D ASG, 1D ASG was removed, and the 2D ASG was directly mounted on the protective cover of the FPD. Three different ASG configurations were evaluated: 1) Without ASG (NO ASG) 2) With 1D ASG, (i.e. the standard ASG in TrueBeam CBCT) 3) With 2D ASG.

To modulate primary and scatter intensity, 30×30 cm² acrylic slab phantoms were employed, and they placed on the carbon-fiber treatment couch. The x-ray source was positioned at "0" degree gantry angle, such that the central axis of the x-ray beam was orthogonal to the couch surface. As described further in Section 2.4, scatter intensity was measured using lead beam stops, and they were placed between the phantom and the x-ray tube. To better visualize the spatial variations in scatter intensity, beam stop measurements were performed at 3 different locations (at CAX, 10 and 20 cm lateral to CAX) as indicated by red circles in the detector plane.

All imaging experiments were performed at 125 kVp beam energy and with 0.9 mm thick built-in titanium beam filter. The x-ray tube was operated in pulsed mode, and tube current and pulse duration were adjusted to achieve sufficient signal intensity in images without saturating the FPD. The CBCT system comes with a built-in ion chamber placed on the x-ray tube exit window; the output of the ionization chamber was used to normalize the projections due to changes in mAs settings and temporal variations in tube output. The FPD was operated at 2×2 pixel binning mode (i.e. pixel size: 0.388 mm). For each measurement, 50 frames were acquired, offset and flat field corrected, corrected for tube output variations, and averaged to reduce image noise. Corrected and averaged images were used in extraction of primary and scatter intensities as described in Sections 2.3 and 2.4. In FIG. 3, the top side view of the experimental setup. Red circles correspond to measurement points, and they are located at CAX, 10 cm, and 20 cm off-axis from CAX at detector plane. In FIG. 3, the bottom side beam eye view of the FPD. 2×40 cm² wide "measurement area" of the FPD is shown in gray. Rest of the FPD was covered with Pb sheet.

2.3 Measurement of Primary Transmission

For primary transmission measurements, phantoms and the couch between the x-ray source and FPD/ASG assembly were removed (Experiment setup 1 in Table 1), and two image sets were acquired: one with and one without an ASG. The ratio of images acquired with and without ASG yielded the primary transmission map. Average primary transmission fraction, ($T_P$), was obtained by averaging the values within a 1.6×1.6 cm² region of interest (ROI) in the primary transmission map, $$T_P = (I(\text{with ASG}))/(I(\text{without ASG})) \times 100 \quad \text{Equation 1}$$

where I is the average of pixel values within the pre-defined ROI. The center of the ROI was centered across the short edge (2 cm) of the measurement area, and shifted along the long edge (40 cm) to calculate $T_P$ as a function of ROI location along the measurement area.

Since FPD pixels underneath the 2D ASG's septa receive lower intensity of primary x-rays, primary transmission varies spatially on a pixel-by-pixel basis, which was not reflected in $T_P$ values. To evaluate this variation, primary transmission values extracted from the primary transmission map were presented in cumulative histograms, referred as primary transmission histograms (PTH).

2.4 Measurement of Scatter Transmission Fraction and Scatter-to-Primary Ratio (SPR)

Figure 4A:
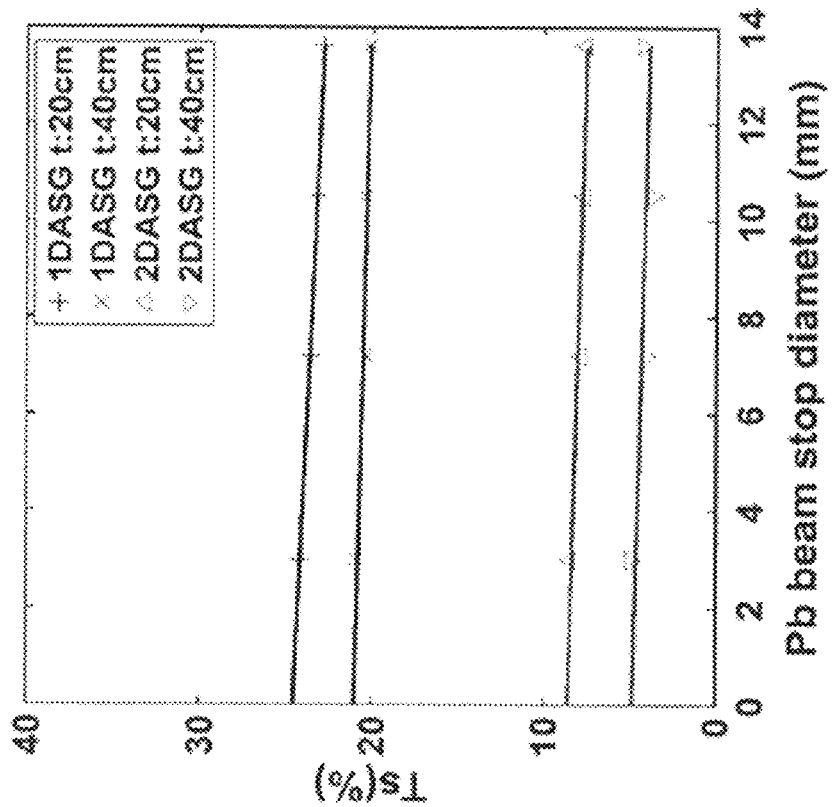
FIG. 4A shows SPR values for 20 and 40 cm thick phantoms were plotted as a function of beam stop diameter. Linear fits were used to extrapolate SPR and $T_S$ values to "0" beam stop diameter. Measurements were performed at 10 cm from CAX, and using Experiment Setup 2 in Table 1.

For scatter intensity measurements, 3.2 mm thick, disc shaped Pb beam stops were mounted on a thin acrylic plate, between the phantom and the x-ray focal spot (FIGS. 4A&B). Beam stops attenuated 99.7% of the primary beam, and the signal intensity in the beam stop shadow yielded the scatter intensity. In each beam stop shadow, a circular region of interest (ROI) was selected with a radius half of beam-stop shadow's radius, and average scatter intensity, $I_S$, was calculated by averaging the pixel values within ROI. To keep the radii of beam stop shadows consistent across all scatter intensity measurements, the beam stop tray was placed at 85 cm from the x-ray focal spot. This way, magnification of beam stop shadows was kept constant at the detector plane.

For Scatter-to-Primary ratio (SPR) measurements, two sets of images were acquired at each experiment setup (Setups 2-4 in Table 1), one with and one without beam stops. SPR was calculated using following, $$SPR = (I_S)/(I_{P+S} - I_S) \quad \text{Equation 2}$$

IS was obtained from images with beam stops as described above, whereas scatter plus primary intensity, IP+S, was obtained by averaging the image signal at the same ROI location in images acquired without beam stops. To quantify the scatter suppression difference between the 1D and 2D ASGs, SPR reduction factor was calculated, which was the ratio of SPRs measured with 1D A and 2D ASGs.

Scatter Transmission fraction, $T_S$, is the fraction of scatter intensity transmitted through an ASG, and it is a key metric in quantifying the scatter suppression performance of ASGs. $T_S$ was calculated using following, $$T_S = (I_S(\text{with ASG}))/(I_S(\text{without ASG})) \times 100 \quad \text{Equation 3}$$

Where IS was obtained from images acquired with and without ASG in place.

As the beam stop size affects scatter intensity, SPR and $T_S$ measurements were performed using 4 different diameter beam stops (their diameters were 3.5, 7.2, 10.5, and 13.6 mm at the detector plane), and they were linearly extrapolated to "0" beam stop diameter by using least squares polynomial fitting [2, 89, 90]. In the Results section, SPR and $T_S$ values at "0" beam stop diameter, and their standard errors were presented. An example of measured SPR and $T_S$ values versus beam stop diameter was shown in FIGS. 4A&B. The data was measured using 20 and 40 cm thick phantoms. Y-axis intercepts of linear fits yielded "0" beam stop diameter SPR and $T_S$ values.

The effect of air gap on SPR and $T_S$ was evaluated using 20 and 35 cm air gaps, and 20 cm thick phantom (Experiment setup 3 in Table 1). Air gap was the distance between the bottom surface of the treatment couch and the FPD plane. The effect of half-fan BT filter was evaluated using 20 cm thick phantom and 20 cm air gap (Experiment setup 4 in Table 1).

TABLE 1

Experiment setups used during primary and scatter transmission measurements

| Setups | Phantom thickness (cm) | Air gap (cm) | BT filter |
|---|---|---|---|
| Setup 1 | No object | N/A | No |
| Setup 2 | 0-40 | 20 | No |
| Setup 3 | 20 | 20 and 35 | No |
| Setup 4 | 20 | 20 | Yes |

Figure 4B:
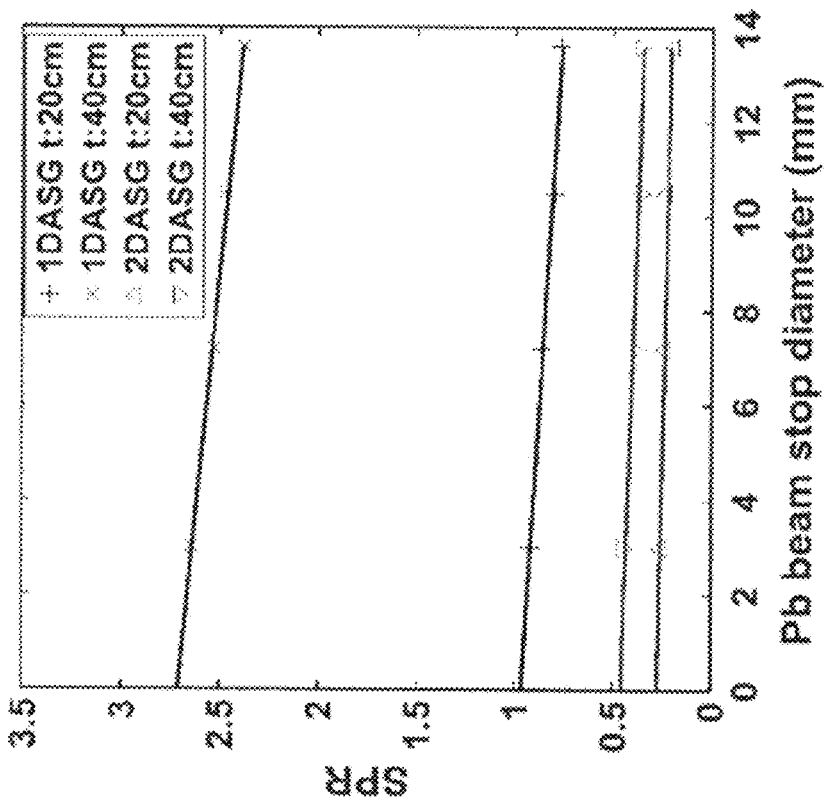
FIG. 4B shows $T_S$ values for 20 and 40 cm thick phantoms were plotted as a function of beam stop diameter. Linear fits were used to extrapolate SPR and $T_S$ values to "0" beam stop diameter. Measurements were performed at 10 cm from CAX, and using Experiment Setup 2 in Table 1.

In FIG. 4A SPR values for 20 and 40 cm thick phantoms were plotted as a function of beam stop diameter. FIG. 4B $T_S$ values for 20 and 40 cm thick phantoms were plotted as a function of beam stop diameter. Linear fits were used to extrapolate SPR and $T_S$ values to "0" beam stop diameter. Measurements were performed at 10 cm from CAX, and using Experiment Setup 2 in Table 1.

2.5 Improvement in Signal to Noise Ratio

Improvement of low contrast object visualization in CBCT images is an important subject as high scatter fraction degrades signal to noise ratio (SNR) in CBCT projections, and subsequently affects tissue visualization in CBCT images [4]. The methodology to evaluate the effect of ASGs on SNR has been developed by several authors in the past [2, 44, 91, 92], and it has been utilized in the context of CBCT [27, 42, 72]. SNR for a contrast object is defined as $$SNR = (cP)/(P+S)^{0.5} \quad \text{Equation 4}$$

where P is primary intensity, S is scatter intensity, and c is a multiplicative factor that defines the primary intensity difference, cP, between the contrast object and the uniform background [2]. In evaluation of ASG's impact on SNR, SNR improvement rather than the SNR value by itself, has been assessed [44, 72]. Thus, SNR improvement factor, $K_{SNR}$, was employed in this evaluation, which is the ratio of SNR with ASG to SNR without ASG. $K_{SNR}$ was calculated as [2], $$K_{SNR} = (T_P(1+SPR)^{0.5})/(T_P + T_S SPR)^{0.5} \quad \text{Equation 5}$$

where SPR was measured without ASG. $K_{SNR}$ more than 1 indicates that the use of ASG increases SNR with respect to SNR without an ASG at a given SPR value, whereas $K_{SNR}$ less than 1 indicates that the ASG reduces the SNR. $K_{SNR}$ for both ASGs were calculated from measured SPR, $T_S$, and $T_P$ values described in Sections 2.3 and 2.4.

3. Results 3.1 Primary Transmission

Figure 5A:
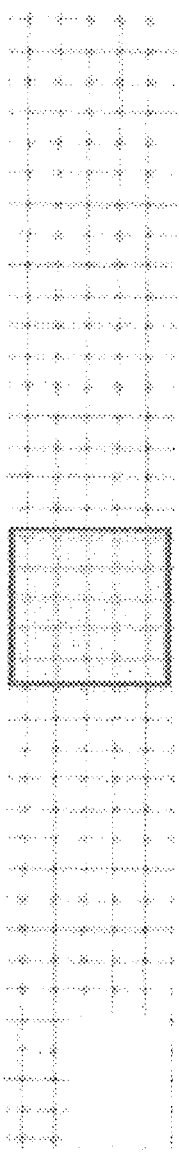
FIG. 5A shows a section of the primary transmission map of 2D ASG, where bright and dark regions indicate higher and lower primary transmission values, respectively. The orange colored square indicates a 1.6×1.6 cm² ROI used for average primary transmission, $T_P$, calculation.

FIG. 5A shows a section of the primary transmission map of the 2D ASG, where brighter and darker regions correspond to through-holes and septa of the 2D ASG, indicating higher and lower primary transmission values, respectively. The orange square shows an ROI that was used for calculation of $T_P$. $T_P$ as a function of ROI location along the measurement area is shown in FIG. 5B. The mean (and standard deviation) of $T_P$ across all ROI locations were 70.6±0.2% and 84.7±0.4% for 1D and 2D ASG, respectively. A slight reduction in 2D ASG's $T_P$ is visible at 20 cm. This location corresponds to the abutment surface of the two 2D ASG modules, where the septal thickness was doubled (i.e. 0.2 mm). Thus, ROIs that included the location of the abutment surface had relatively lower $T_P$ values.

Figure 5C:
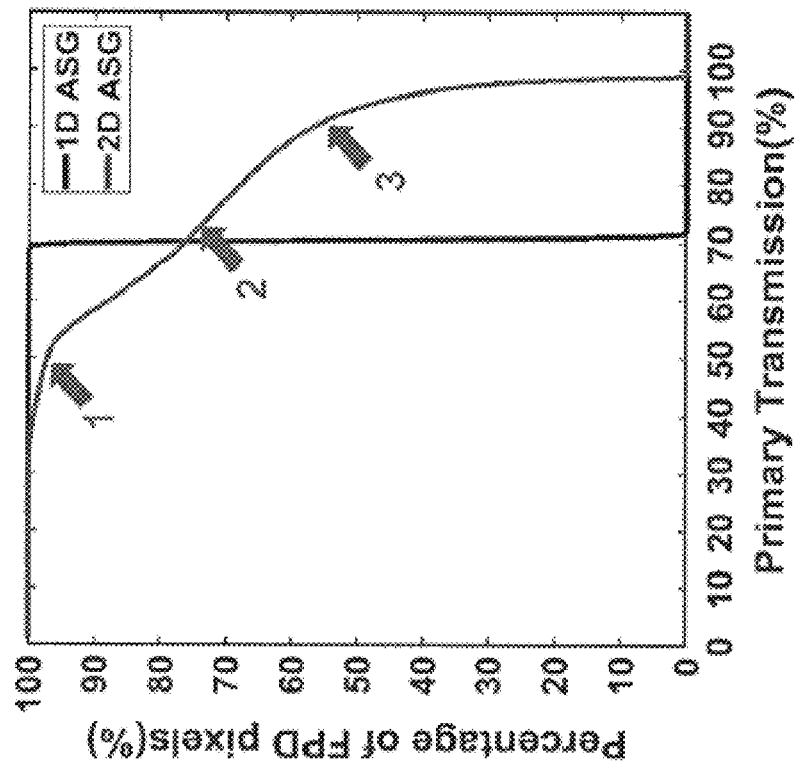
FIG. 5C shows cumulative primary transmission histograms of 1D and 2D ASGs.
Figure 5B:
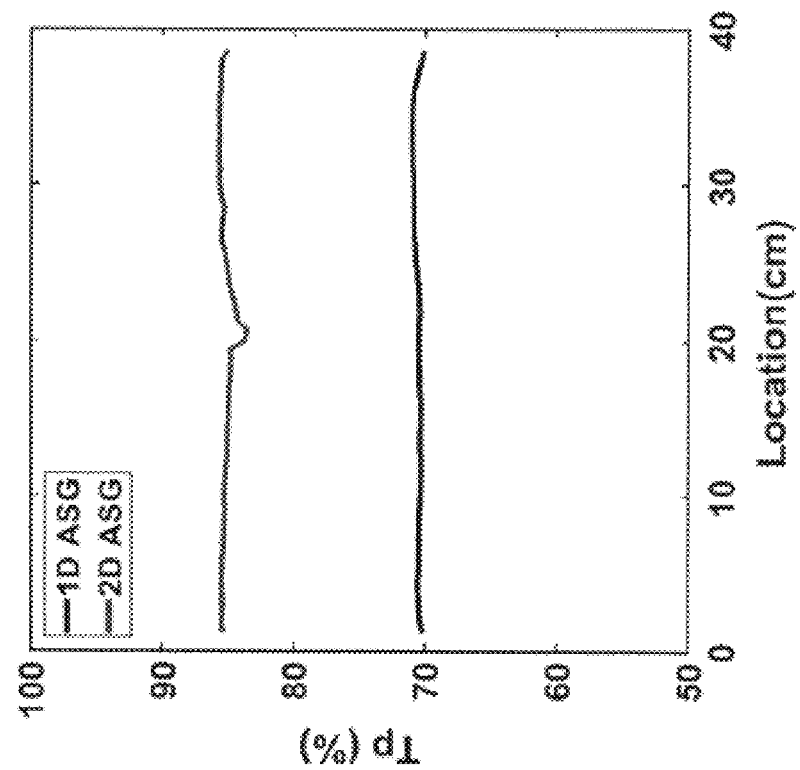
FIG. 5B shows $T_P$ as a function of ROI location along the long edge of the primary transmission map.

To better quantify the variation in primary transmission, cumulative primary transmission histograms (PTH) were calculated FIG. 5C). For 1D and 2D ASGs, minimum-maximum pixel specific primary transmission values were 68.3%-72% and 32.5%-99.1%, respectively. Although, FPD pixels underneath the 2D ASG's septa received low primary transmission, the percentage of such pixels was relatively small; 97.2% of the pixels received 50% or higher primary transmission (Arrow 1), and 75% of pixels received 72% or higher primary transmission, which was maximum pixel specific primary transmission value measured with 1D ASG. Finally, 57% of the pixels received 90% or more primary transmission with 2D ASG (red arrow 3). FIG. 5A shows a section of the primary transmission map of 2D ASG, where bright and dark regions indicate higher and lower primary transmission values, respectively. The orange colored square indicates a 1.6×1.6 cm² ROI used for average primary transmission, $T_P$, calculation. FIG. 5B shows $T_P$ as a function of ROI location along the long edge of the primary transmission map. FIG. 5C shows a cumulative primary transmission histograms of 1D and 2D ASGs.

3.2 Scatter to Primary Ratio (SPR)

SPR values as a function of phantom thickness and ASG configuration were measured using Experiment Setup 2

Figures 6A, 6B, 6C:
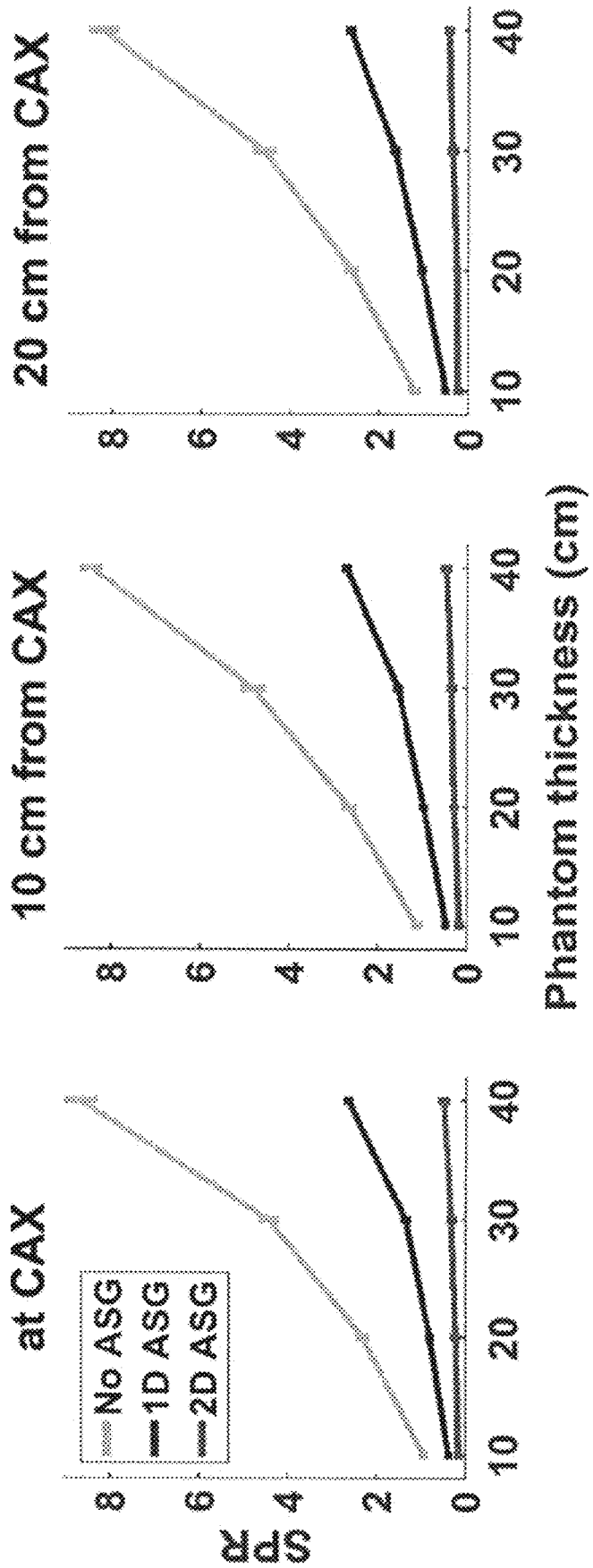
FIGS. 6A, 6B and 6C show SPR variation as a function of phantom thickness at 3 measurement points (CAX, 10 cm from CAX, and 20 cm from CAX, respectively).

(Table 1), and results are shown in FIGS. 6A, 6C and 60C. As SPR values did not vary considerably across measurement points, only the results at 10 cm from CAX were summarized below, and in Table 2. SPR without ASG increased from 1.11 to 8.44 as a function of increasing phantom thickness, and 1D ASG reduced the SPR range to 0.45-2.71. 2D ASG further reduced SPR range to 0.16-0.46. When compared to 1D ASG, 2D ASG provided a factor of 2.81 to 5.89 reduction in SPR, and SPR reduction by 2D ASG was more pronounced at larger phantom thicknesses.

Figure 7B:
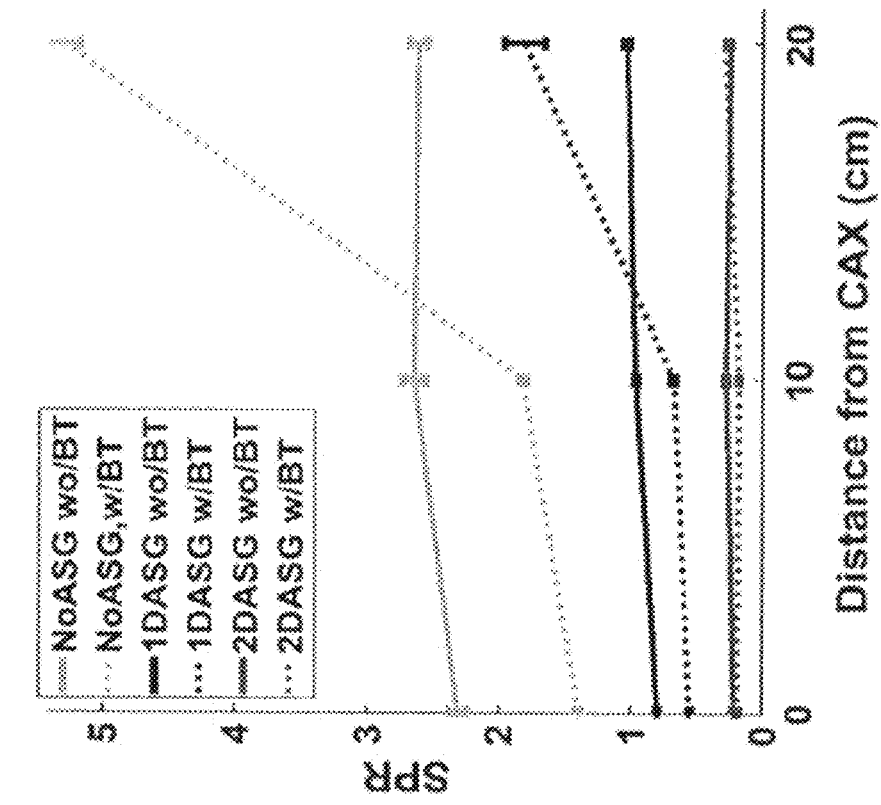
FIG. 7B shows the effect of BT filter on SPR as a function of measurement locations.
Figure 7A:
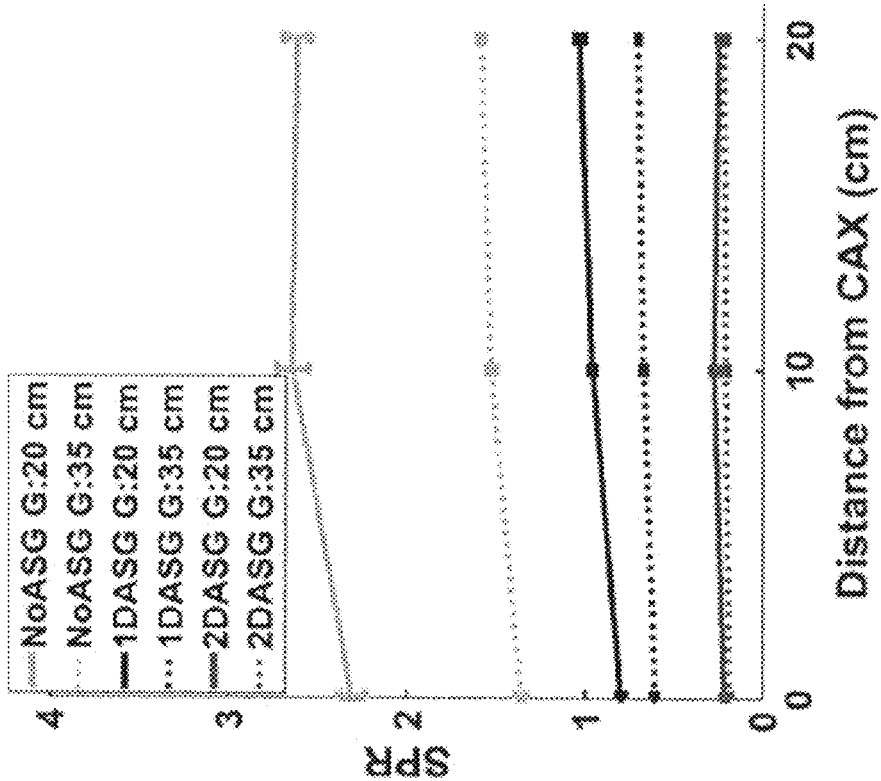
FIG. 7A shows the effect of air gap on SPR as a function of measurement locations.

The effect of air gap on SPR was evaluated using Experiment Setup 3 (Table 1). SPR was reduced for all ASG configurations when the air gap was increased from 20 cm to 35 cm (FIG. 7A). At 10 cm from CAX, SPRs with 1D and 2D ASG were reduced from 0.96 to 0.67, and from 0.27 to 0.21, respectively (Table 3). At 35 cm air gap, 2D ASG provided a factor of 3.19 lower SPR than 1D ASG.

The effect of BT filter on SPR varied spatially in all ASG configurations (FIG. 7B): While BT filter reduced SPR within 10 cm of CAX, SPR increased at 20 cm away from CAX for all ASG configurations. 2D ASG continued to provide lower SPR values with respect to 1D ASG with BT filter in place (Table 4). For example, at 10 cm from CAX, SPRs with 1D and 2D ASGs were 0.68 and 0.18, respectively. SPR reduction factors provided by 2D ASG were 3.78 and 6.24 at 10 and 20 cm from CAX, respectively.

TABLE 2

SPR values as a function of phantom thickness at 10 cm from CAX point.

| Phantom thickness (cm) | SPR | | | SPR reduction factor |
|---|---|---|---|---|
| | NOASG | 1D ASG | 2D ASG | |
| 10 | 1.11 ± 0.04 | 0.45 ± 0.01 | 0.16 ± 0.01 | 2.81 |
| 20 | 2.64 ± 0.09 | 0.96 ± 0.02 | 0.27 ± 0.02 | 3.56 |
| 30 | 4.80 ± 0.20 | 1.54 ± 0.01 | 0.34 ± 0.03 | 4.53 |
| 40 | 8.44 ± 0.18 | 2.71 ± 0.03 | 0.46 ± 0.06 | 5.89 |

TABLE 3

SPR values as a function of air gap at 10 cm from CAX

| Air gap (cm) | SPR | | | SPR reduction factor |
|---|---|---|---|---|
| | NOASG | 1D ASG | 2D ASG | |
| 20 | 2.64 ± 0.09 | 0.96 ± 0.02 | 0.27 ± 0.02 | 3.56 |
| 35 | 1.53 ± 0.02 | 0.67 ± 0.01 | 0.21 ± 0.01 | 3.19 |

TABLE 4

SPR values as a function of BT filter status at 10 and 20 cm from CAX.

| Measurement location | BT filter status | SPR | | | SPR Reduction factor |
|---|---|---|---|---|---|
| | | NOASG | 1D ASG | 2D ASG | |
| 10 cm from CAX | No | 2.64 ± 0.09 | 0.96 ± 0.02 | 0.27 ± 0.02 | 3.56 |
| 10 cm from CAX | Yes | 1.82 ± 0.02 | 0.68 ± 0.02 | 0.18 ± 0.01 | 3.78 |
| 20 cm from CAX | No | 2.62 ± 0.07 | 1.04 ± 0.02 | 0.23 ± 0.01 | 4.52 |
| 20 cm from CAX | Yes | 5.3 ± 0.12 | 1.81 ± 0.15 | 0.29 ± 0.01 | 6.24 |

3.3 Scatter Transmission Fraction ($T_S$)

Figures 8A, 8B, 8C:
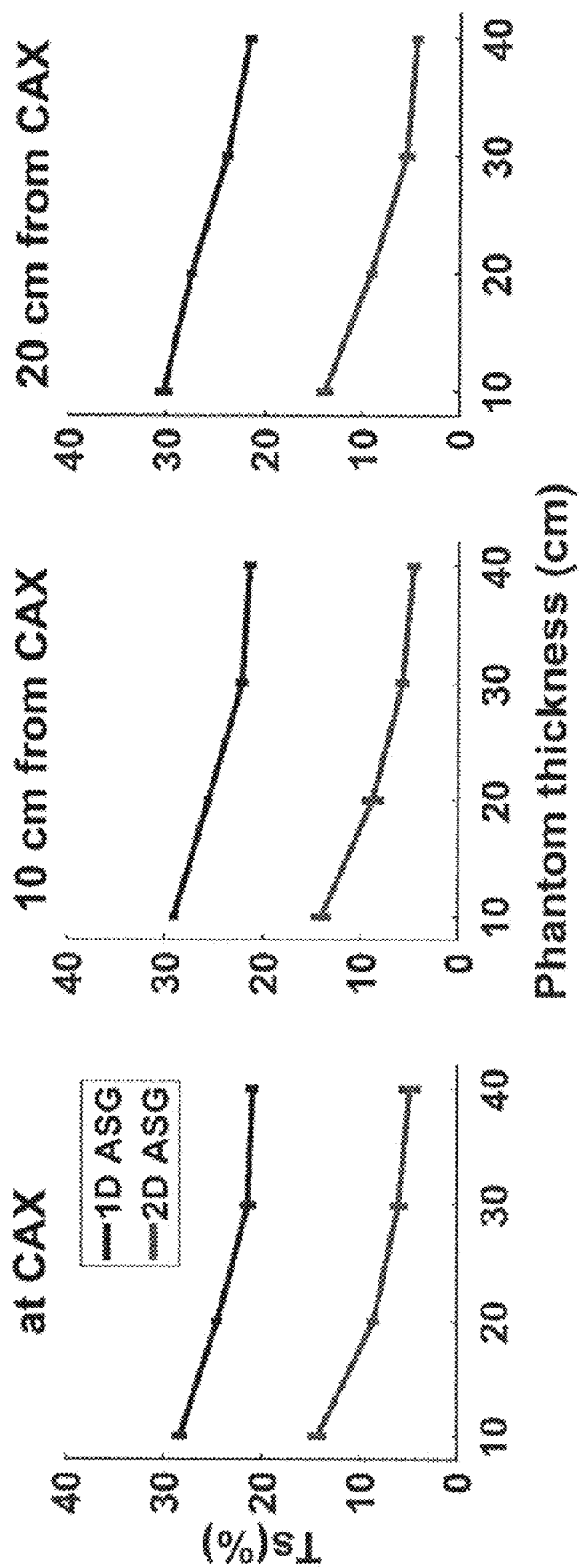
FIGS. 8A, 8B and 8C show $T_S$ as a function of phantom thickness at 3 measurement points (CAX, 10 cm from CAX, and 20 cm from CAX, respectively).

$T_S$ as a function of phantom thickness was measured using Experiment Setup 2, and results are shown in FIGS. 8A, 8B and 8C. At any given phantom thickness and ASG configuration, $T_S$ values varied less than 2% across all measurement points. $T_S$ for both ASGs were reduced as phantom thickness increased, that indicated better scatter suppression performance at large phantom thicknesses. At 10 cm from CAX, $T_S$ of 1D and 2D ASGs were in the range of 21.3-29.1% and 4.6-14%, respectively (Table 5). When compared to 1D ASG, reduction in $T_S$ with 2D ASG was more pronounced at larger phantom thicknesses; when the phantom thickness increased from 10 to 40 cm.

Figure 9B:
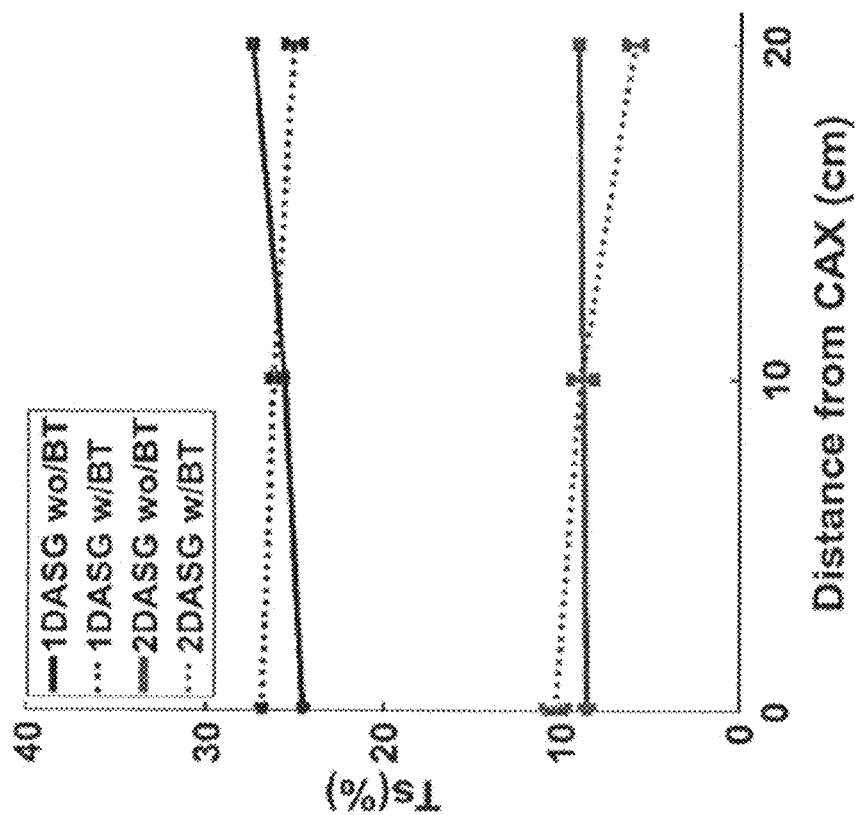
FIG. 9B shows $T_S$ measured with and without BT filter.
Figure 9A:
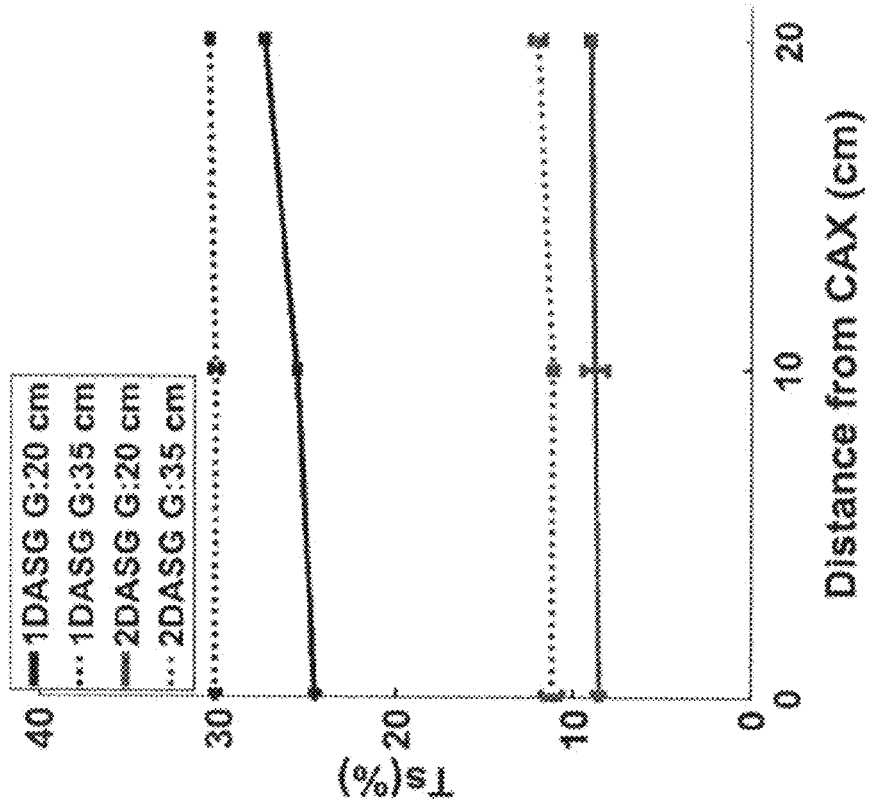
FIG. 9A shows $T_S$ as different air gaps were plotted at all 3 measurement points.

As shown in FIG. 9A, $T_S$ increased as air gap increased from 20 to 35 cm for both ASGs, indicating that scatter suppression efficiency was reduced at larger air gaps. At 10 cm from CAX, relative increase in $T_S$ was 18% and 25% for 1D and 2D ASGs, respectively. 2D ASG still provided lower $T_S$ with respect to 1D ASG (Table 6).

In contrast to SPR, $T_S$ measured with BT filter did not exhibit large variations across the three measurement points (FIG. 9B), and BT filter did not make a large impact on $T_S$; $T_S$ increased slightly at CAX, and reduced monotonically further away from CAX with BT filter in place. $T_S$ values measured with BT filter were within 1-3% of the values measured without BT filter. 2D ASG continued to provide lower $T_S$ values with respect to 1D ASG (Table 7).

TABLE 5

$T_s$ as a function of phantom thickness at 10 cm from CAX.

| Phantom thickness (cm) | $T_s$ | |
|---|---|---|
| | 1D ASG | 2D ASG |
| 10 | 29.1 ± 0.1% | 14.0 ± 0.7% |
| 20 | 25.6 ± 0.1% | 8.8 ± 0.7% |
| 30 | 22.2 ± 0.2% | 5.7 ± 0.3% |
| 40 | 21.3 ± 0.2% | 4.6 ± 0.3% |

TABLE 6

$T_s$ as a function of air gap at 10 cm from CAX.

| Air gap (cm) | $T_s$ | |
|---|---|---|
| | 1D ASG | 2D ASG |
| 20 | 25.6 ± 0.1% | 8.8 ± 0.7% |
| 35 | 30.2 ± 0.3% | 11.1 ± 0.2% |

TABLE 7

T$_s$ as a function of BT filter status at 10 and 20 cm from CAX.

| Measurement location | BT filter status | T$_s$ | |
| --- | --- | --- | --- |
| | | 1D ASG | 2D ASG |
| 10 cm from CAX | No | 25.6 ± 0.1% | 8.8 ± 0.7% |
| 10 cm from CAX | Yes | 26.2 ± 0.3% | 8.9 ± 0.6% |
| 20 cm from CAX | No | 27.4 ± 0.1% | 9.1 ± 0.1% |
| 20 cm from CAX | Yes | 25.1 ± 0.5% | 5.9 ± 0.5% |

3.4 SNR Improvement Factor

Figure 10:
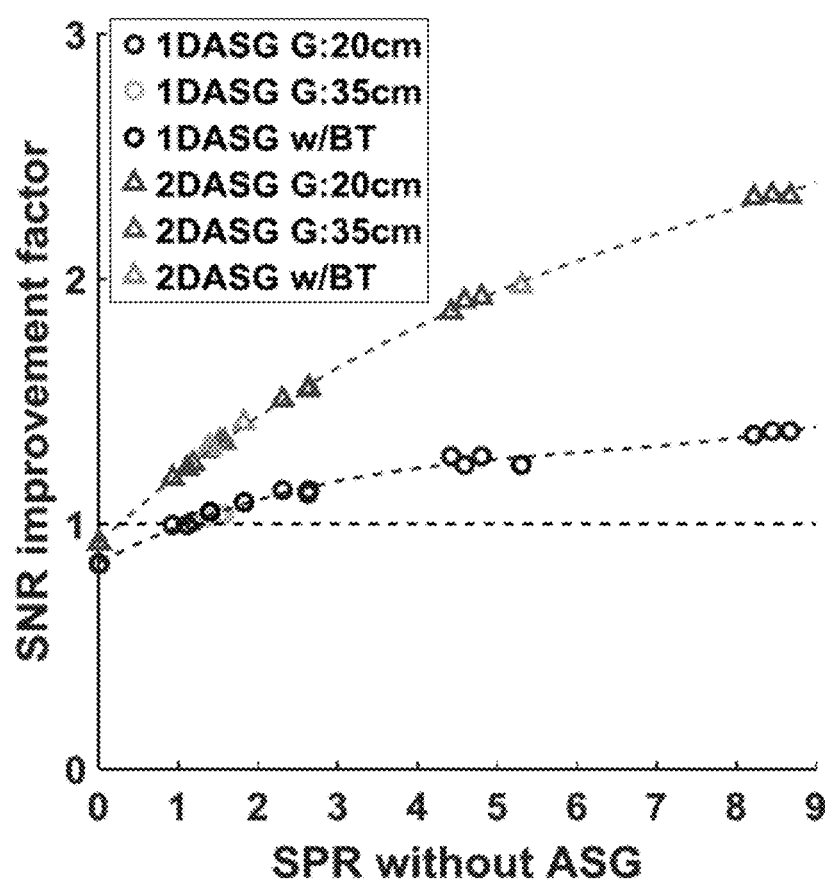
FIG. 10 shows SNR improvement factors, $K_{SNR}$, were plotted as a function of SPR without ASG. $K_{SNR}$ values were calculated for all measurement points and experiment setups (See Table 1). Cubic polynomials (red and blue lines) were fitted to better visualize trends in $K_{SNR}$.

K$_{SNR}$ was calculated for all measurement points, and all experiment setups (See Table 1), and it was plotted as a function of SPR without ASG (FIG. 10). FIG. 10 shows SNR improvement factors, K$_{SNR}$, were plotted as a function of SPR without ASG. K$_{SNR}$ values were calculated for all measurement points and experiment setups (See Table 1). Cubic polynomials (red and blue lines) were fitted to better visualize trends in K$_{SNR}$. Cubic polynomials were fitted to data points to visualize the trends (blue and red lines). When compared to 1D ASG, 2D ASG provided higher K$_{SNR}$ values across the range of SPRs investigated in this study, and SNR improvement provided by 2D ASG was more emphasized particularly at high SPR conditions. For example, at SPR of 8.7, K$_{SNR}$ achieved by 1D ASG was 1.38, whereas 2D ASG provided K$_{SNR}$ of 2.34, indicating a K$_{SNR}$ increase by a factor of 1.7 with respect to 1D ASG. Change in air gap and presence of BT filter did not make any large difference in K$_{SNR}$ trends. When SPR was 1.1 or below, K$_{SNR}$ of 1D ASG was less than 1, indicating that SNR was degraded with respect to SNR without ASG. For 2D ASG, transition from SNR improvement to SNR degradation occurred (i.e. K$_{SNR}$ below 1) at SPR of 0.27. At SPR of 0, K$_{SNR}$ of 1D and 2D ASGs were 0.84 and 0.92, respectively, which implies that degradation of SNR was less with 2D ASG in the absence of scatter.

4. Summary and Discussions

A 2D ASG prototype aimed for CBCT systems in radiation therapy was developed and evaluated its x-ray transmission characteristics. As shown in Section 3.1, 2D ASG prototype provided about 20% higher primary transmission on the average than the 1D ASG installed in the clinical CBCT system. There are multiple factors that explain the higher average primary transmission provided by the 2D ASG. First, due to the self-supporting structure of the 2D grid, interseptal spacers are not needed, whereas fiber spacers used between septa of 1D ASG that attenuate the primary beam. The second factor is the effect of grid geometry on primary transmission. The 2D ASG has a large grid pitch (2.91 mm) with respect to its septal thickness (0.1 mm) that leads to a relatively small footprint on the FPD38; the area covered by the 2D ASG's tungsten septa constitutes less than 7% of the FPD's imaging area. On the other hand, 1D ASG has a relatively small pitch (0.167 mm) with respect to its septal thickness (0.036 mm), and hence, its footprint covers about 21% of the FPD's imaging area. Another factor that affects primary transmission is the suboptimal geometry and focusing of ASG's septa. Nonuniformities in septal thickness and deviations of septa from ideal focusing geometry would increase the shadow of septa in projections, and subsequently, would reduce primary transmission. Geometric accuracy of 1D and 2D ASGs' septa cannot be measured directly in projection images (due to the small septal thickness with respect to FPD pixel size), and therefore, its impact on primary transmission was not assessed in this study. However, spatial variations in ASG's geometric accuracy can be evaluated via observing spatial variations in T$_P$. Standard deviation of T$_P$ was 0.2% and 0.4% for 1D and 2D ASGs, respectively, while their mean T$_P$ values were 70.6% (1D ASG) and 84.7% (2D ASG). Such a small variation in T$_P$ indicates that the geometric accuracy of both ASGs was uniform across the measurement area. While 2D ASG provided higher "average" primary transmission, pixel specific primary transmission varied between 32.5% and 99.1% due to the 2D ASG's shadow in projections; FPD pixels that were underneath the 2D ASG's septa received less primary beam with respect to pixels at the center of grid holes, as visualized in FIG. 5A. With 1D ASG, variation of pixel specific primary transmission was less than 4%, mainly due to its smaller septal pitch with respect to the FPD's pixel pitch. Although, 2D ASG provided lower primary transmission to a fraction of pixels, the percentage of such pixels was relatively small, and 75% of pixels still received more primary transmission than the maximum pixel specific primary transmission provided by 1D ASG.

From scatter suppression point of view, 2D ASG provided significantly better performance in all imaging conditions that have been evaluated. When compared to the 1D ASG, SPRs measured were lower by a factor of 3-6 with 2D ASG. Both ASGs provided better scatter suppression for larger object thicknesses, as indicated by their lower T$_S$ values at larger phantom thicknesses. When the air gap was increased from 20 to 35 cm, SPR was reduced in all ASG configurations. However, reduction in SPR was due to the relative reduction in scatter intensity at larger air gaps [27, 44, 93]. On the other hand, scatter rejection performance of both ASGs deteriorated at increased air gap, which was indicated by the increase in T$_S$ values at 35 cm air gap. This observation was in agreement with other reports in the literature [41, 42]; as the air gap increases, the angular distribution of scatter is less broad, and scattered radiation is less likely to be stopped by ASG's septa.

BT filter spatially modulates both primary and scatter beam intensity, and caused spatially nonuniform SPR distribution [28, 74, 94]. When compared to measurements without BT filter, SPR was lower in regions close to CAX where primary intensity was higher due to the thinner BT filter section, and SPR increased further away from CAX, where primary intensity was lower due to increased BT filter thickness. These observations apply to both ASGs and NO ASG configuration, which are qualitatively in agreement with the literature [28, 75]. While BT filter caused larger variations in SPR, its impact on the scatter suppression performance of 1D and 2D ASGs was less pronounced, as indicated by the relatively small difference (3.2% or less) in T$_S$ values measured with and without BT filter.

Numerous studies have established that reduced scatter fraction in CBCT projections translates into improved CT number accuracy and reduced image artifacts [4, 27, 28, 41, 72, 95]. Thus, it is expected that improved scatter suppression performance of 2D ASG may be likely to increase the CT number accuracy and reduce scatter-induced artifacts with respect to CBCT images acquired with 1D ASG. Besides improvement of CT number accuracy, another area of interest is the improvement of low contrast resolution. While ASGs reduce scatter intensity, and have a positive effect on improving SNR, they also reduce primary intensity, that deteriorates SNR and contrast resolution. In addition to the transmission characteristics of the ASG, relative intensity of scatter, or SPR, incident on the FPD determines the level of SNR improvement or degradation with the use of ASG. Several studies have reported that conventional 1D ASGs reduced SNR and contrast resolution in low to medium scatter intensity environments, where SPR was below 1-2. In this evaluation, SNR degradation with 1D ASG (i.e. $K_{SNR}<1$) occurred at SPR values below 1.1, and this result was in agreement with the literature [27, 28, 42]. Since SPR for various anatomical sites is generally less than two, the role of 1D ASGs in SNR improvement is typically limited to high SPR imaging conditions, such as CBCT imaging of Pelvis or abdomen [27, 28, 41, 42].

Across the SPR range investigated in this study, SNR improvement with 2D ASG was up to a factor of 1.7 higher than 1D ASG. At higher SPR values, lower scatter transmission by 2D ASG plays an important role in SNR improvement. At lower SPR values (e.g. SPR<1), higher primary transmission by 2D ASG becomes a more dominant factor in SNR improvement, as the scatter intensity constitutes a smaller faction of the total x-ray intensity incident on the FPD. The role of higher primary transmission is particularly evident at "0" SPR condition, where SNR improvement is solely determined by the primary transmission characteristics of an ASG. At "0" SPR (FIG. 10), $K_{SNR}$ of 1D and 2D ASGs were 0.84 and 0.92, respectively. As a combined effect of both lower scatter and higher primary transmission, 2D ASG provided SNR improvement at SPR values down to 0.27. Therefore, the 2D ASG may potentially improve contrast resolution in a larger range of SPR conditions with respect to conventional 1D ASGs.

One evaluation employed a 1D ASG with a grid ratio of 10, as it was the ASG installed in the clinical TrueBeam CBCT system. While this is a typical grid ratio for commonly utilized 1D ASGs, 1D ASGs with grid ratios above 15 have been developed in recent years. Such ASGs may provide improved scatter suppression and SNR performance in CBCT imaging. For example, Wiegert et al. [42] investigated a 1D ASG with a grid ratio of 27, and showed that $T_S$ was a factor 2-3 lower with respect to a 1D ASG with a grid ratio of 10. However, SNR improvement with high grid ratio was worse, except in high scatter imaging conditions (e.g. SPR>5), which was attributed to poor primary transmission characteristics of the ASG. Stankovic et al. [62] employed a 1D ASG with grid ratio of 21 in a linac mounted CBCT system. They have shown that both CT number accuracy and contrast to noise ratio (CNR) was improved in a wide range of scatter conditions with respect to CBCT images acquired without ASG. Fetterly and Schueler investigated a similar 1D ASG for digital radiography [3]. They reported a factor 2-3 lower $T_S$ and comparable $T_P$ with respect to 1D ASGs with moderate grid ratios, and better SNR improvement in a wide range of scatter conditions. Comparison of 2D ASGs with such high grid ratio 1D ASGs is an area remains to be investigated.

One of the challenges in implementation of 2D ASGs in CBCT is the correction of its septal shadow, or footprint, in projections. If not addressed properly, spatial variations in image intensity may likely to lead to ring artifacts in reconstructed images. Moreover, variations in image intensity may also lead to spatially nonuniform image noise in reconstructions. Similar challenges have been faced in utilization of 2D ASGs in breast tomosynthesis [87], and nonlinear grid reciprocation schemes have been implemented to blur the ASG's footprint by moving the ASG at high frequency during x-ray exposure [96]. A similar approach was also utilized for crosshatched ASGs in mammography [47]. Moreover, image post processing based correction algorithms were developed for 1D ASGs that exploit the periodicity of septa footprint to suppress ASG's footprint in projections [97-99]. Such post processing approaches may as well be implemented in the context of 2D ASGs.

1. Conclusions

A prototype 2D ASG was developed and its x-ray transmission properties were evaluated in half-fan geometry of a linac mounted CBCT system. When compared to a conventional 1D ASG, 2D ASG reduced SPRs by a factor of 3-6, while providing 19% higher primary transmission on the average. It was observed that scatter suppression advantage of 2D ASG was maintained at increased air gap and with bow tie filter in place. It is expected that lower SPR values achieved with 2D ASG may potentially translate into reduced image artifacts and improved CT number accuracy in CBCT. In addition, when compared to 1D ASG, 2D ASG improved SNR in projections in a wide range of SPRs due to its higher primary transmission and scatter suppression capability. It is believed that improved SNR in projections may lead to improved contrast resolution in CBCT images. While 2D ASG exhibited better scatter and primary transmission characteristics, its septal footprint leads to spatially varying primary transmission in projections that may cause artifacts in reconstructed images. If the correction of its septal footprint is addressed, 2D ASG can be a promising scatter suppression device in improvement of CBCT image quality in the future.

Example 3

Configuration of Current X-Ray Flat Panel Detectors and 1D ASGS

Conventional, Potter-Bucky antiscatter grid: An array of 1D lead strips and inter-spacers (so called Potter-Bucky grids). Such Potter-Bucky grids absorb scattered x-rays while transmitting primary x-rays. Such grids are an "add-on" component to the flat panel detector assembly.

Phosphor (scintillator layer): Phosphor layer absorbs incident x-rays and converts them to visible light photons. It is a continuous layer placed (or directly deposited) on the detector's pixel array. Since phosphor is a continuous layer, visible light photons from an x-ray interaction, diffuse within the phosphor, and spread over to multiple pixels. Thus it reduces the spatial resolution of the detector.

Detector pixel array: It converts the visible light photons to electrical charge, which is converted to digitized signal.

Figure 15:
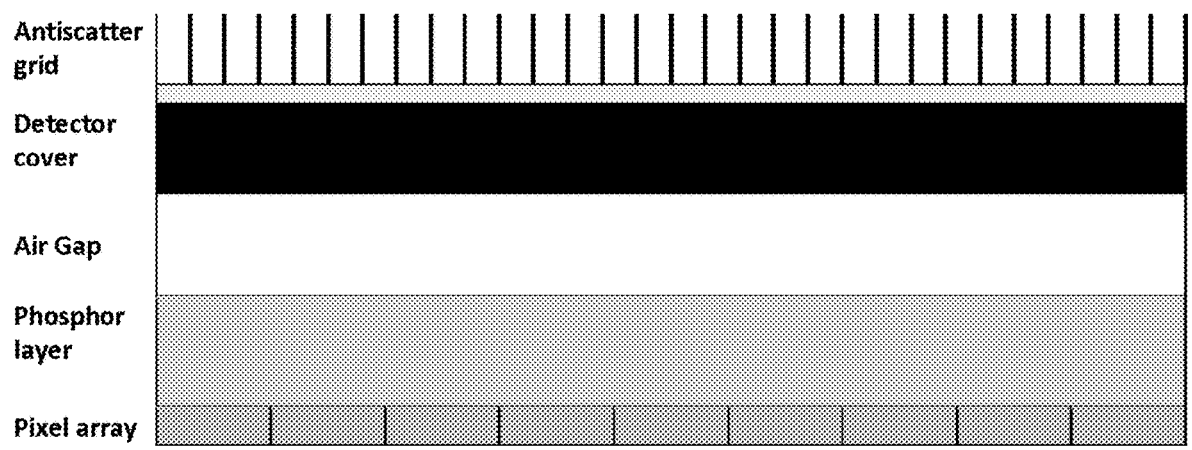
FIG. 15 shows an example of the configuration of a current x-ray flat panel detector and 1D anti-scatter grid.

One of the disadvantages of this approach the increased distance between the pixel array and the ASG, see FIG. 15.

Example 4

Hybrid Flat Panel Detector of the Current Invention

Figure 16:
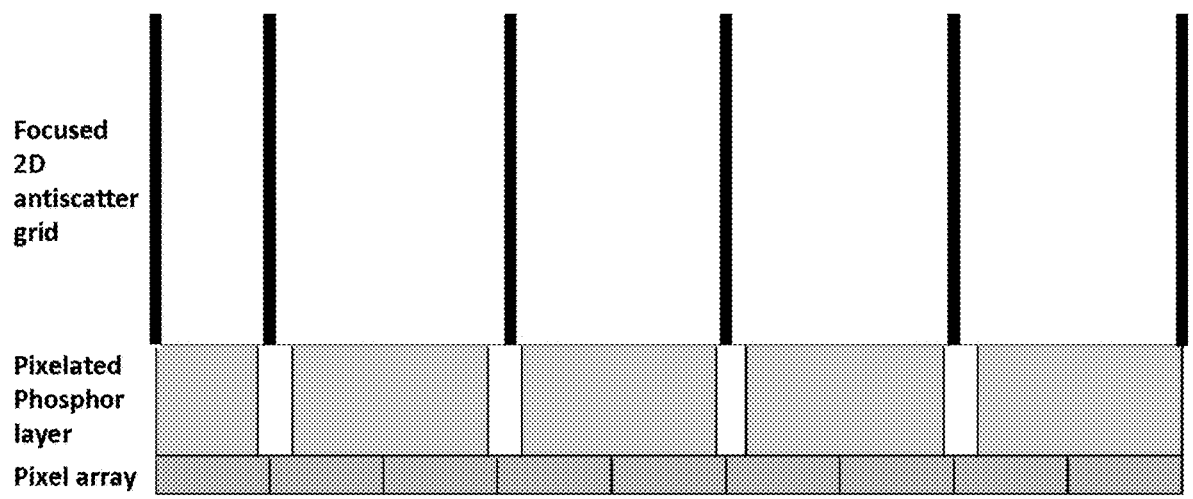
FIG. 16 shows one embodiment of the current invention 2D grid placed on the phosphor layer.

The 1D Potter-Bucky grid described in Example 3 is replaced with one embodiment of the current invention, a 2D antiscatter grid, and the 2D grid is directly placed on the phosphor layer such as in FIG. 16. A continuous phosphor layer is replaced with a pixelated phosphor layer. Pixels in the phosphor are separated with reflective septa, preventing diffusion of visible light photons neighboring detector pixels. The 2D grid's walls are aligned with the septa in the phosphor layer, minimizing the "inactive" area of the flat panel detector. This benefit cannot be achieved with the conventional approach previously described (i.e. the grid is mounted on the top of the protective detector cover; walls cannot be perfectly aligned with the septa of phosphor layer).

Some advantages of this hybrid design over existing flat panel detectors include the following:
- Air gap and detector cover between the 2D ASG and pixel array is eliminated. As a result, the shadow of 2D ASG is minimized in FPD images.
- Pixelated phosphor structure reduces cross-talk between detector pixels, improves spatial and contrast resolution (see FIG. 22).
- 2D grid provides better scatter absorption and improved primary x-ray transmission with respect to conventional antiscatter grids. In return, it reduces noise in CBCT images and improves the accuracy of CT numbers (reduced noise leads to better soft tissue visualization, improved CT number accuracy leads to improved tissue density estimation in CBCT images).
- Integration of pixelated phosphor with the 2D antiscatter grid reduces the percentage of "inactive" detector area, thus more primary x-rays will be detected by the detector. This approach will reduce noise in CBCT images.

Although this approach may appear similar to the conventional CT scanner detectors, it uses a flat detector and a different pixel array technology. Flat detector employs either amorphous silicon or CMOS pixel arrays to reduce the pixel size and the footprint of the flat detector.

Example 5

Innovations in the Current Invention

Using a 2D grid and a pixelated scintillator in a flat panel detector for CBCT has not been previously described. The differences in grid and scintillator designs are important to achieve high image quality/cost effectiveness/fabrication feasibility. A viable design is both feasible to fabricate and feasible to integrate with a flat detector. More importantly, the design of the current invention should provide better image quality than competing grids and other technologies. As outlined below, there are unique properties of the disclosed design that makes the grid fabrication feasible and provide better image quality than existing technologies:

Adjustment of Focusing Geometry and Fabrication Method:
- Focusing geometry should be adjusted such that grid's channels are directed to the focal point of the x-ray source.
- The method of grid fabrication can be critical to the adjustability of the current invention to various system configurations and geometries. In one embodiment, a laser sintering process may be used for fabrication of the grids. In one embodiment, the laser sintering process enables the fabrication of the 2D grid with the desired physical characteristics.

Using a Pixelated Scintillator in a Flat Panel Detector:

Pixelated scintillators are typically used to reduce the spread of optical photons within the scintillator, and to improve spatial resolution. Currently, pixelated scintillators are not used in flat detectors, and there are good reasons for it: To improve the spatial resolution with a pixelated scintillator, the pixel size of the scintillator should match pixel size of the flat detector array. Flat detector pixel size is about 200 microns (varies between 100 and 400 microns, depending on the make and model). Thus, the pixel size of the scintillator should be in the order of 200 microns, which is challenging and expensive fabricate.

The pixelated scintillators of the current invention are primarily used to improve the performance of 2D grids with a flat panel detector. The pixel size of the scintillator is matched to the size of the 2D grid's channels rather than the detector array pixels. As a result, the pixel size of the scintillator will be 2-3 mm (feasible to fabricate). In the next section, it is examined why this is a preferred approach. In a CT detector, the detector pixel size is ~1 mm (factor of 25 larger than flat detector's pixel), and scintillators with 1 mm wide pixels can be fabricated.

Selection of the Optimal Size of 2D Grid's Channels

In CT detectors, 2D grid's channels have the same size as the detector array pixels (channel size and the detector's pixel size are both ~1 mm). However, this approach is very challenging to implement in flat panel detectors (~200 micron detector pixel size): To match the flat detector's pixel size, a 2D grid should have a 200 microns channel width. If the grid channel is 200 microns wide and channel walls are 50-100 microns thick, a large percentage of the grid will be made of channel walls. Hence, most of the detector will be obstructed by the grid's footprint, which would lead to very poor transparency for primary x-rays. Since primary x-rays generate the useful signal in the detector, lower signal levels would lead to lower signal to noise ratio in images.

In the current invention, the approach is different than previous approaches. The grid channel size is much larger than the detector pixel size: the channel widths (or pitch) are in the order of 2-5 mms. The selection of channel width depends on the channel wall thickness to achieve the desired primary x-ray transmission characteristics. The grid channel width does not depend on the detector pixel size. For example, for a grid channel width of 3 mm, and a channel wall thickness of 100 microns, the footprint of the grid shadow will be much less, and the primary x-ray transparency will be higher. About 85% of the primary x-rays will be transmitted through the grid, see FIG. 17.

The 2D Grid's Channels does not Need to be Aligned with the Detector Pixel Array.

In a CT detector, 2D grid's channel walls are aligned with the dead space between the CT detector's pixels. In fact, this proposed approach in flat detectors is described in US Patent application publication 2004-0251420 A1 [100], herein incorporated by reference. However, a typical large area flat detector has up to 43 cm width. Alignment of 200 micron wide grid channels with 200 micron wide detector pixels is quite challenging over such a large length/area. This is a lesser issue in CT systems as CT detectors are modular and smaller (each detector tile is less than 10×10 cm²).

In contrast to CT detectors and the patent application cited above, channel walls are not aligned with the detector pixels in the current invention. With this approach, the integration of the detector with the 2D grid is more practical. Since the proposed 2D grid is not aligned with detector pixels, any grid channel shape can be used in the 2D grid (rectangular, hexagonal etc.). As a consequence of my approach, pixels in the shadow of the channel walls will have reduced signal. But, based on my selection of the channel size (2-4 mm) and channel wall thickness (~100 microns), such a signal reduction will not have a major impact in image quality. (See FIG. 18 below). Only a small percentage of pixels will be impacted by the shadow of the channel walls.

Selection of optimal wall thickness is important to minimize the effect of channel wall shadows on the image, and it is also crucial for fabrication feasibility.

Figure 18:
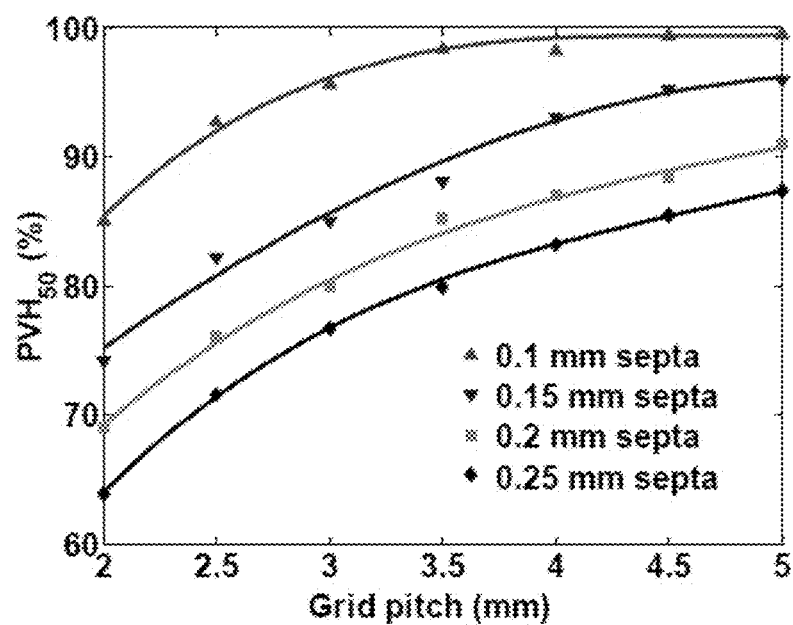
FIG. 18 shows the percentage of detector pixels that receive at least 50% of the nominal signal (PVH50) with the 2D grid. Without the 2D grid, all pixels will receive 100% of the nominal signal. When the 2D grid is in place, detector pixels in the shadow of the 2D grid will receive reduced signal. For example, for a grid channel width (pitch) of 3 mm and wall thickness of 100 microns (red curve), 95% of the pixels will still receive at 50% of the nominal signal. Only 5% of the pixels will receive less than 50% of the nominal signal. This 5% of the pixels are considered "dead" pixels. As the signal they receive is significantly reduced due to the 2D grid's shadow. Markers indicate the calculated values by the model, and lines are polynomial fits.

To minimize the channel wall shadows in the image, the channel wall thickness should be as thin as possible. However, fabrication process becomes more challenging for thinner wall thicknesses. One embodiment of the present invention, the laser sintering process is utilized, as wall thickness of 100 microns can be achieved and 2D grids up to 20×20 cm$^2$ can be fabricated. Thus, a 2D grid for a large area flat detector (e.g. 40×40 cm$^2$) can be built only from four 2D grid tiles. For wall thicknesses less than 100 microns, only two technologies exist (Vogtmeier et al. [88] and Tang et al. [101]. In one embodiment, the current invention contemplates increasing the wall thickness to, say 200-250 microns. Then other technologies can be used fabricate the proposed grid. However, if the wall thickness is increased to 200 microns, the shadow of the channel walls may be too large, and detector pixels in the wall shadows will receive little or no signal. These pixels will essentially be dead pixels, as shown in FIG. 18. In summary, in the current invention design (with 100 micron channel wall thickness and ~3 mm wide channels), the signal reduction in the channel wall shadows will be at acceptable levels, and the fabrication feasibility is preserved.

The 2D grid's shadow in the image must be corrected for high image quality. This is a very important subject for the integration of 2D grids with flat detectors. If the shadow of the 2D grid is not fully corrected, it will lead to image artifacts. If not addressed correctly, correction of grid shadows will be a major roadblock in implementation of 2D grids in flat panel detector systems.

Correction option 1: The magnitude of signal reduction due to grid's shadow can be measured on a pixel by pixel basis under reference conditions. This "calibration data" can be later used to process images and correct the reduction in signal due to grid. Such calibration data based correction methods are already known.

Correction option 2: The option 1 above may not be a robust correction method due to long distance cross-talk in non-pixelated scintillators (see FIG. 21): Due to continuous (non-pixelated) scintillator layer in the flat detectors, some of the light photons travel large distances laterally, and get detected by detector pixels far from the original location of x-ray absorption. This long distance cross-talk is also known as glare. The magnitude of glare depends on the properties of the imaged object, therefore "the calibration data" based approach in Option 1 cannot correctly handle the excess signal. The magnitude of veiling glare compromises the robustness of the correction option 1 above.

That's where the pixelated scintillators come into play (see the pixelated scintillator in FIG. 22). If the scintillator is pixelated, this long-distance cross talk will be prevented, and the reduced signal in the 2D grid's shadow can be better predicted. The prevention of long distance cross-talk will also provide some improvement in spatial resolution.

To reduce long distance cross talk, scintillator's pixel size does not need to be as small as detector's pixels (as in CT detectors). Thus, in the disclosure, the pixel size of the scintillator will be matched to the width of the grid's channels, and pixels of the scintillator will be aligned with channel walls of the 2D grid. With the alignment of scintillator pixels and the grid's channels.

There are significant advantages to placing the 2D grid directly on the top of the scintillator (rather than on the top of the protective cover of the flat detector). The first advantage is the ability to align 2D grid's channels with the pixelated scintillator, as described in previously. The other advantage is the reduced effective height of the 2D grid (If the grid is installed on the protective cover, there will be about a 1 cm gap between the grid and the scintillator layer). Reduced grid height becomes important, when flat detector/ grid assembly is used in a CBCT gantry (Please see the "gantry flex and grid shadow" illustration in FIG. 20). A CBCT gantry typically "wobbles or flexes" slightly when it rotates around the patient due to flexing of the gantry arms under gravity. As a result, the position of the x-ray source changes in relation to the grid/detector assembly, and the shadow of the grid on the detector shifts. This "wobble or gantry flex" problem makes the correction of the grid shadow challenging. Higher the grid the worse the problem gets. Thus, by directly mounting the grid on the scintillator, the effective height of the grid can be reduced from ~3 cm to ~2 cm (physical height of the grid is assumed to be 2 cm).

Is the "gantry flex and grid height" an issue in CT systems? CT gantries are built using a completely different architecture. They have minimal gantry flex/or wobble. Thus, the grid height is much less of an issue.

Example 6

Calculations of the 2D Grid's Physical Characteristics)

1) The slant or angle of the 2D grid's channels: Angle of the grid's channels follow the divergence of the x-ray beam, thus the calculation of channel angles is not unique to the disclosed 2D grid design. In other words, any grid design should incorporate similar channel angles such that channels are pointing towards the x-ray source.

Figure 17:
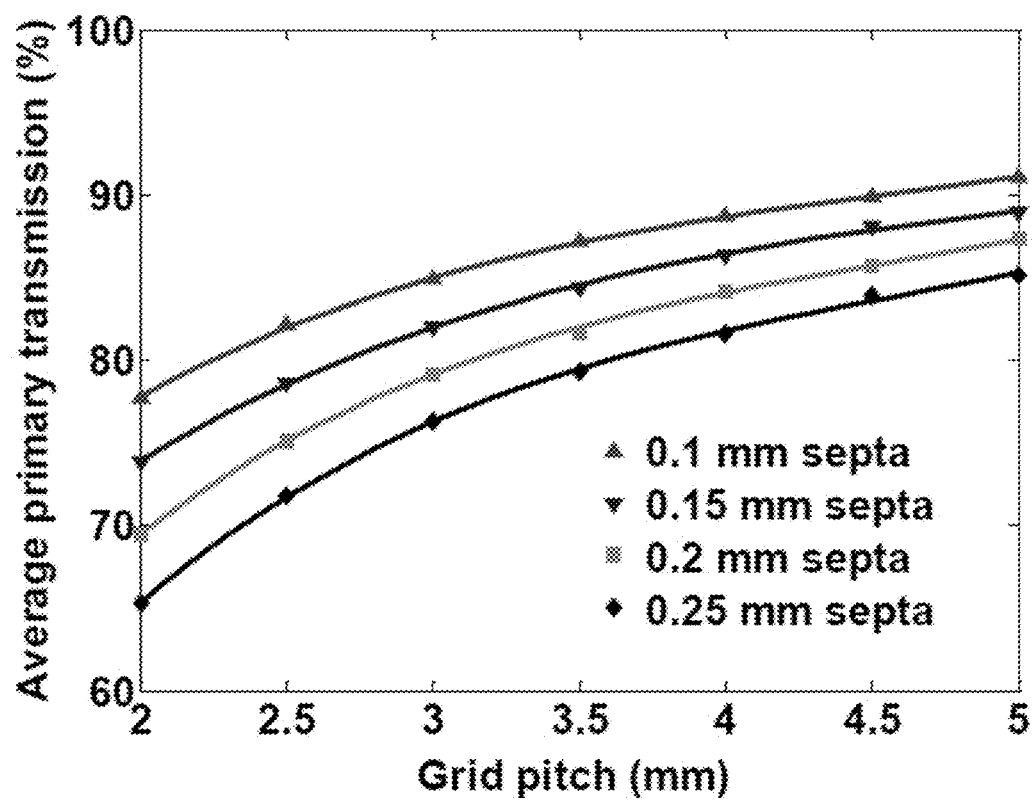
FIG. 17 shows the percent primary x-ray transmission fraction was calculated as a function of grid's septal thickness (i.e. wall thickness) and grid pitch (i.e. grid's channel width) in the 2D ASG model. For a 100 micron thick wall and 3 mm wide channels, 85% of the primary x-ray is transmitted through the grid.

2) Primary x-ray transmission characteristics: Primary transmission is primarily a function of grid channel width and channel wall thickness. This is one of the fundamental properties of the 2D grid. Example 2 describes the calculation of the primary transmission. FIG. 17 and FIG. 18 are from Example 2. Essentially, the proposed grid provides significantly better primary transmission that conventional antiscatter grids used with flat detectors (FIG. 17). Conventional grids transmit only 60-70% of primary x-rays, whereas the 2D grid with 3 mm channel width and 100 micron wall thickness transmits 85% of primary x-rays (higher the primary transmission the better).

3) Scattered x-ray transmission characteristics: Grid channel's height to width ratio (also known as grid ratio) is the primary factor that determines the scatter transmission characteristics. Based on preliminary experiments, a 2D grid with a grid ratio of 12 transmits approximately 6% of the scattered x-rays, whereas conventional grid with a similar grid ratio transmits 10-15% the scatter (lower the scatter transmission the better). Although theoretically 2D grid's grid ratio (and height) can be increased to provide even lower scatter transmission, it is not practically possible due multiple reasons (manufacturing challenges, thicker grid will be closer to the patient (patient hazard), makes it harder to correct grid's shadow due to gantry flex (as explained in item 5 above). In one embodiment, the grid ratio of a 2D grid will be around 6-15, and the height of the grid will be a maximum of 5 cm or so). In one embodiment, a 2D grid with a grid ratio of 10, and a grid channel width of 3 mm, the grid height will be 3 cm.

4) Benefits of integrating pixelated scintillator and 2D grid with a flat panel detector array. Numerical calculations to predict its benefits are not straightforward, but can be done in the longer term (i.e. reduced long-range cross talk, improved corrections of 2D grid's shadows). The integration of the 2D grid with the pixelated scintillator provides more benefits than the benefits of the individual components as it is a synergistic combination. A pixelated scintillator with 3 mm pixels can be incorporated into a flat detector without the 2D grid, and long distance crosstalk can be reduced.

However, the pixelated scintillator and the reduced crosstalk also improves the correction of 2D grid's shadow in the image.

Example 7

A Method to Correct Scatter Intensity Using a 2D Antiscatter Grid

Background: The purpose of the 2D antiscatter grid is to stop scattered x-rays reaching the flat panel detector, and improve the image quality. However, a fraction of scattered x-rays can still pass through the 2D grid, and reach the detector. As a result, the image quality would be deteriorated.

Although, 2D grid's height (or grid ratio) can be increased to reduce the transmission of scatter, such a grid design will lead to other technical and practical challenges. For example, increased grid height is more difficult to fabricate, and it can also absorb more primary x-rays (i.e. useful x-rays that form the image), which deteriorates image quality.

Purpose of the innovation: The disclosed method utilizes the 2D grid itself as a device to estimate the residual scatter transmitted through the 2D grid to the flat panel detector. Once the residual scatter intensity reaching the detector is estimated, the scatter intensity can be "corrected" to improve image quality. This invention expands the utility of the 2D grid. In addition to being a scatter rejection device (as explained in my previous disclosure), the 2D grid is utilized as a device to estimate and correct residual scatter reaching the detector.

Figure 19:
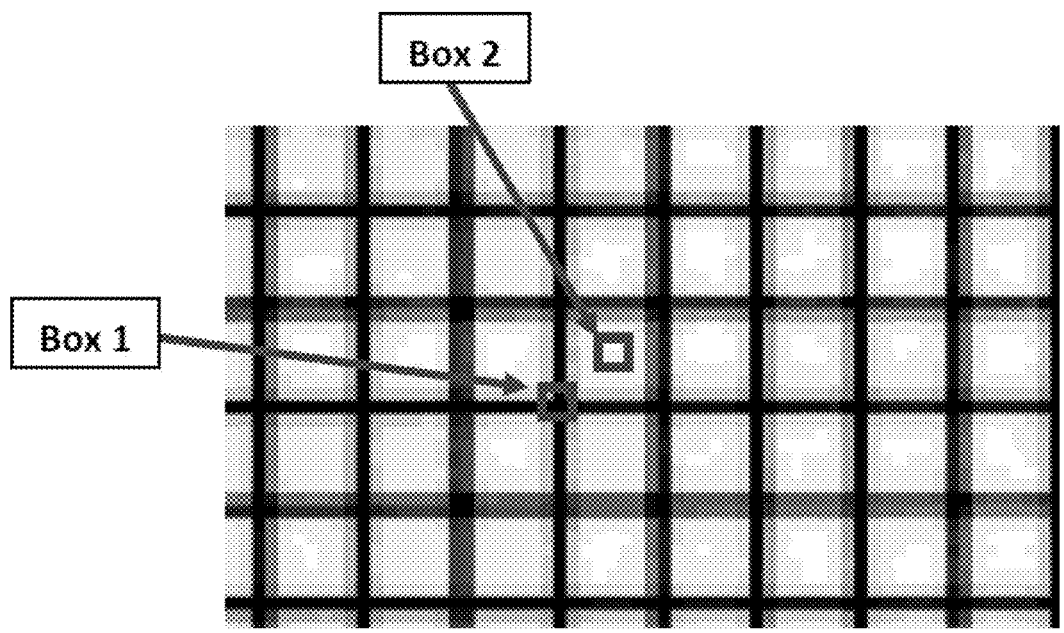
FIG. 19 shows an X-ray image with a 2D grid in place. Box 1 shows a region underneath the 2D grid's footprint, and Box 2 indicates a region at the center of a grid hole. The ratio of image intensity in Box 1 and Box 2 is a unique value. This intensity ratio changes as a function of scatter content in the image. This ratio is measured without scatter present in the image (calibration data). Calibration data can later be used to estimate the scatter intensity in patient images. Such "box pairs" can be created for other points underneath the grid's footprint and grid hole centers. As a result, scatter intensity can be estimated for any point in the image.

How it works: The 2D grid's footprint introduces a unique pattern of image signal intensity variations as shown in FIG. 19. In the absence of scattered-rays (i.e. without any imaged object in the field), the ratio of image intensity underneath the grid's footprint (red box 1) and at the center of a grid hole (red box 2) has a unique value. While imaging an object, majority of the scatter will be stopped by the 2D grid, and a small fraction of scatter will reach detector. As a result, this unique ratio of signal intensities in Boxes 1 and 2 will change.

If the ratio of signal intensities in Box 1 and 2 are measured without scattered x-rays, a calibration data can be generated. This calibration data can be used to estimate the scatter intensity when an object is imaged using the following equation.

$$S = I_2((I_1/I_2) - (P_1/P_2))/(1 - ((P_1/P_2)))$$   Equation 6

S=Scatter intensity in Box 2, when an object is imaged
$I_1$=Image intensity in Box 1 when an object is imaged
$I_2$=Image intensity in Box 2 when an object is imaged
$P_1$=Image intensity in Box 1 under calibration conditions (no scatter is present in the image)
$P_2$=Image intensity in Box 2 under calibration conditions (no scatter is present in the image)

The calculation described above can be repeated for any arbitrary "box pairs" in the image shown in FIG. 19. Thus, scatter intensity can be calculated for any point in the image to get a 2D scatter intensity map. Subsequently, scatter correction is achieved by subtracting this scatter intensity map from the image. The equation described above shows one way of calculating the scatter intensity using the 2D grid's footprint in images. Fourier domain methods may also be used to calculate the scatter intensity.

Thus, specific compositions and methods of a hybrid flat panel detector for cone beam CT systems have been disclosed. It should be apparent, however, to those skilled in the art that many more modifications besides those already described are possible without departing from the inventive concepts herein. Moreover, in interpreting the disclosure, all terms should be interpreted in the broadest possible manner consistent with the context. In particular, the terms "comprise" and "comprising" should be interpreted as referring to elements, components, or steps in a non-exclusive manner, indicating that the referenced elements, components, or steps may be present, or utilized, or combined with other elements, components, or steps that are not expressly referenced.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application are hereby incorporated by reference.

Example 8

A Computational Model of a 2D ASG Photon-Counting Detector

This example is directed to understand the physics of x-ray transmission and detection in 2D ASG/photon counting detector assembly, and investigate the effect of various 2D ASG and detector configurations on CBCT image quality. The second goal of this example is to investigate aft fluence modulation approach, and identify optimal 2D ASG grid geometries.

To study the x-ray transmission, we will employ an x-ray spectrum model [28], and GEANT4 for Tomographic Emission (GATE) Monte Carlo package to simulate x-ray transmission through the phantom and 2D ASG [29]. The imaging system geometry will mimic the imaging conditions of a linac mounted CBCT system, and we will employ various phantom setups depicting various anatomical sites. We will also simulate the CdTe detector to study the effects detector backscatter. GATE simulations will provide the incident x-ray spectrum on the detector, and we will investigate how 2D ASG geometry (such as grid height, pitch, septal thickness, and septa footing) affects the transmitted spectrum of primary and scattered x-rays. We will also study the characteristic x-rays emitted from tungsten septa. While the overall contribution of tungsten characteristic x-rays to spectrum contamination is expected to be small, it may have a larger contribution in pixels located in septal shadows. As, our proposed Aft Fluence Method employs pixel counts in septal shadows, we will evaluate whether spectral contamination in septal shadows affect the efficacy of our fluence modulation approach.

To investigate the detected energy spectrum in the CdTe detector, we will model the detector response, or signal formation, by adopting the methodology used by Schmidt [30]. Modeling the detector's energy response with GATE simulated incident x-ray spectrum will enable us to study the effects of charge sharing and the "detected" energy spectrum for a variety 2D ASG geometries and pixel sizes.

Example 9

Experimental Evaluation of 2D ASG Scattered Radiation Reduction

We will measure scatter and primary transmission characteristics of the 2D ASG, using well-established approaches [17], and determine whether sufficient spectral decontamination is achieved by performing dual energy CBCT imaging experiments; we will assess the noise characteristics of CBCT images, contrast-to-noise ratio (CNR) improvement, and accuracy of iodinated contrast quantification in a variety of phantoms mimicking clinically relevant anatomical shapes. We will also be able to quantify the spatial variations in spectral contamination (i.e. spectral contamination in septal shadows versus center of grid holes). These studies will be performed at low x-ray fluences to minimize the effect of pulse-pile up on our evaluations.

We will setup a benchtop CBCT system using a fixed anode x-ray tube, a linear photon counting detector, and a rotation stage for the phantom. As such linear detectors are about 40-50 mms in length, we will perform multiple acquisitions for each projection by translating the detector in the transverse plane.

While a linear detector will allow us to reconstruct only the central CBCT slice, we will emulate the scatter conditions of full CBCT exposure geometry (the size of the exposed area will be about 30×40 cm2 at detector plane). To suppress potential grid artifacts caused by septal shadows, we will explore various detector calibration approaches, and implement a total variation minimization (TVM) based grid artifact suppression algorithm.

Example 10

AFT Fluence Modulation Validation

This example characterizes improvement in count rate and energy resolution performance under clinically relevant fluence environments.

We will test two 2D ASG septal configurations one with standard (constant thickness) septa and the other one with septal footing. First, we will characterize the pixel response as a function of incident fluence, and assess the effects of pulse pile-up both in septal shadows and in the center of the through-holes; we will observe the differential changes in count rate changes in these two regions and determine the conditions that will employ the Aft Fluence Method. As the detector can be translated with respect to a fixed 2D ASG in our benchtop system, we will be able to change the grid position with respect to detector pixels in a precise manner, and investigate the effects of grid/pixel alignment on Fluence modulation patterns and pixel-specific energy resolution.

Specifically, we will evaluate the energy response of pixels neighboring the septal shadows; as we hypothesize that energy resolution in such pixels can be improved due to reduced charge sharing (described in Section 2.2). We will assess the magnitude of improvement in energy resolution in such pixels. If we can successfully demonstrate that energy resolution is improved in such pixels, novel photon counting detectors can be developed in the feature, where grid septal pitch is matched to detector pixel pitch, reducing charge sharing among all neighboring pixels, and hence, improving energy resolution of photon counting detectors.

We will also perform an image quality comparison of photon-counting CBCT to single energy FPD based CBCT. This step is aimed to demonstrate the utility of proposed solutions as well as the benefits of photon counting approach in CBCT under realistic imaging conditions.

Example 11

The present technology is pertinent to x-ray imaging systems that employ antiscatter grids (2D or 1D). As described in this Example 11, a method may be provided to realign a 2D or 1D grid when the detector is offset with respect to the x-ray source, or vice versa. Detector (or x-ray source) offsetting may be particularly important in the context of CBCT systems that employ flat panel detectors. With this method, the same antiscatter grid can be used in both centered and offset detector geometry.

Figure 32:
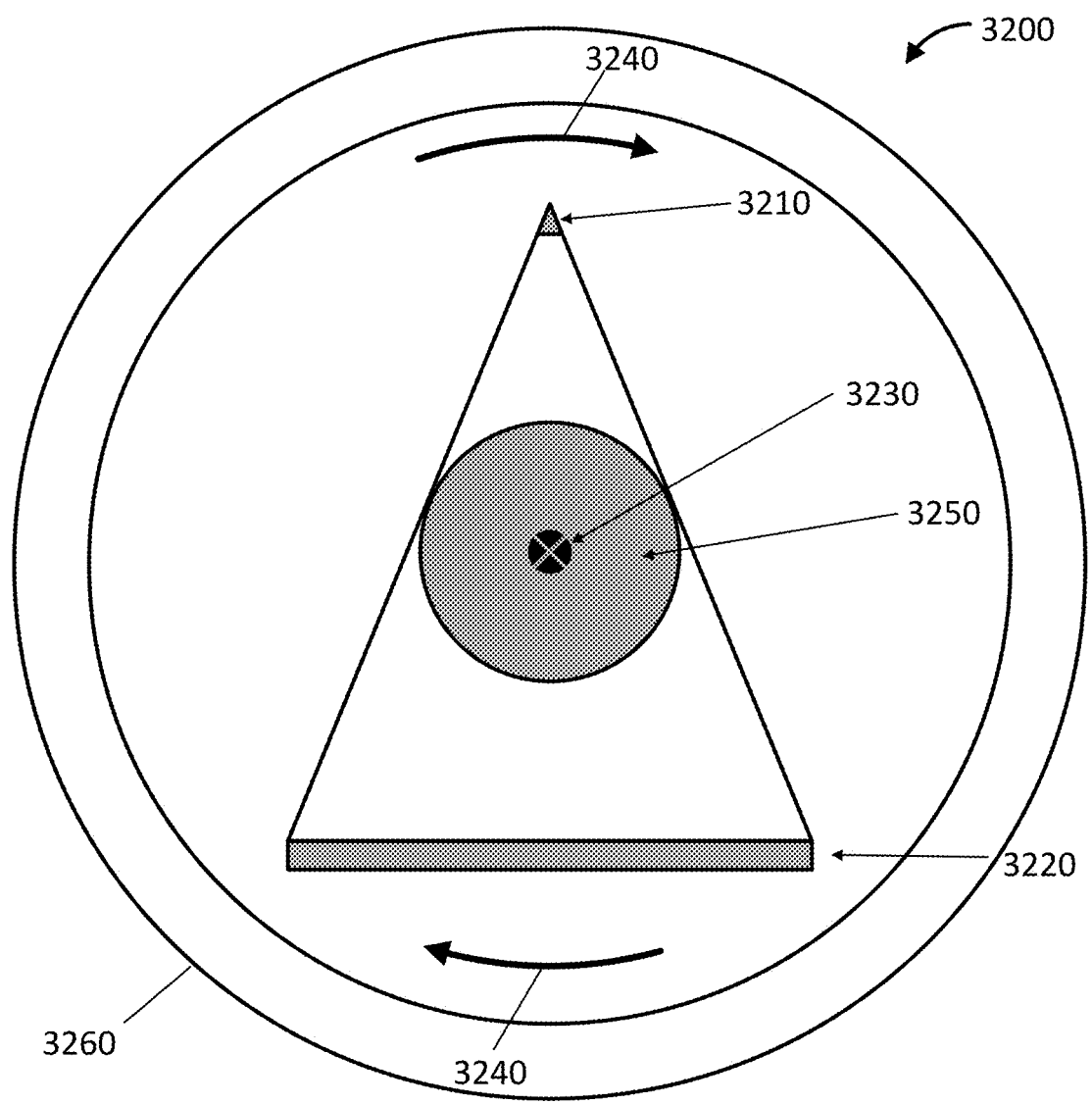
FIG. 32 presents a diagram of a centered detector CBCT geometry for a CBCT system according to a known embodiment.

FIG. 32 presents a diagram of a centered detector CBCT geometry for a CBCT system 3200 according to a known embodiment. In a typical CBCT system 3200, an x-ray source 3210 and an x-ray detector 3220 rotates around the center 3230 of rotation 3240 to generate a 3D image. A field of view (FOV) 3250 is indicated by the circular shaded region in FIG. 32. In the known system 3200, to make the FOV 3250 larger, a larger detector 3220 is needed. However, this may not be feasible in most instances, as such large detectors may not be available, or they can be expensive. In some cases, as where the x-ray source 3210 and detector 3220 are situated in an O-shaped gantry 3260, sizing considerations may come into play such that it is not possible to use a larger detector 3220 given limitations on dimensions of the O-shaped gantry 3260.

Figure 33:
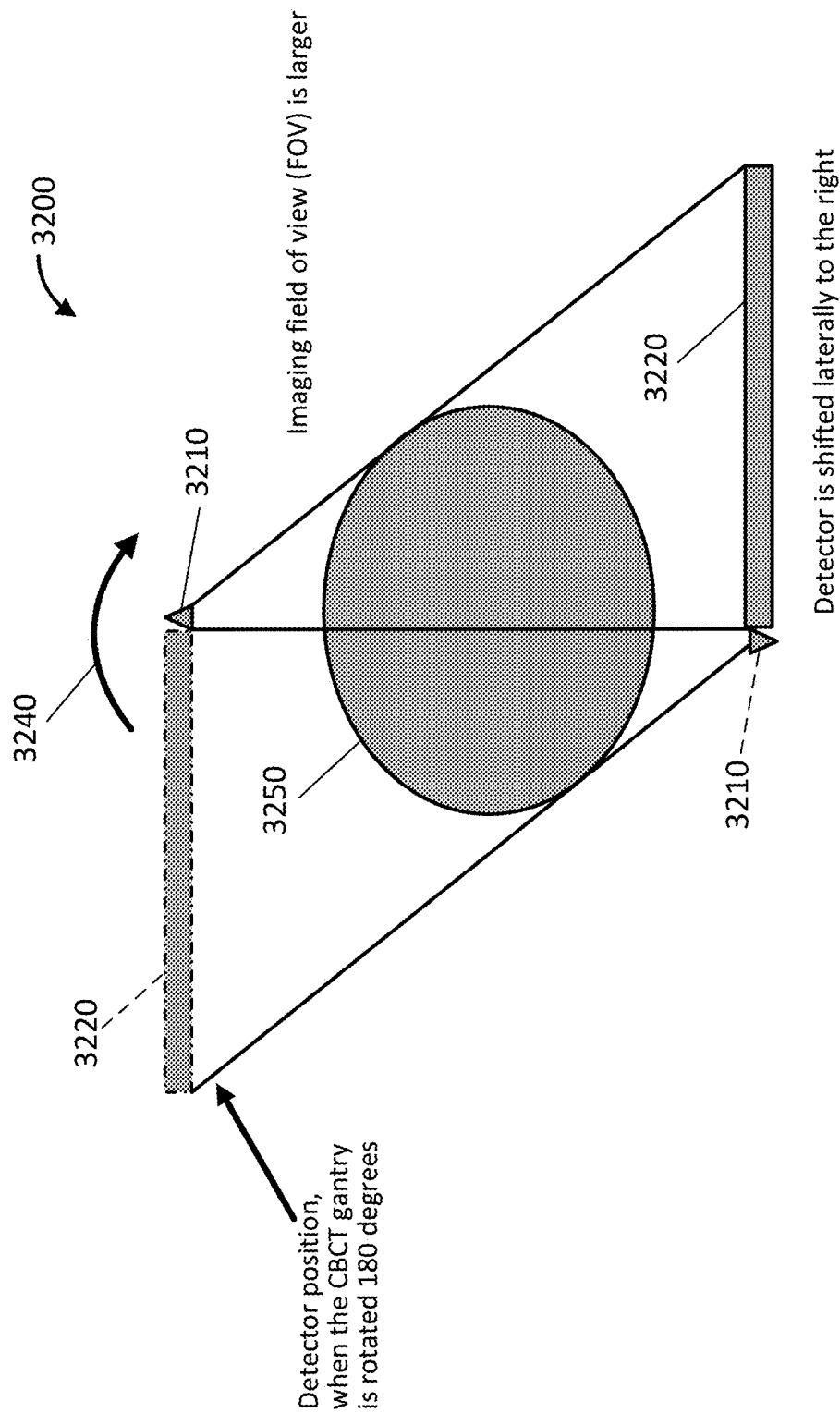
FIG. 33 presents a diagram of an offset detector CBCT geometry for a CBCT system according to a known embodiment.

FIG. 33 presents a diagram of an offset detector CBCT geometry for the known CBCT system 3200 shown in FIG. 32. With further reference to FIG. 32, the known technique shown in FIG. 33 may make the FOV 3250 larger using the illustrated offset detector geometry. In this known technique, the detector 3220 is shifted laterally, and only half of the FOV 3250 is imaged during each detector 3220 position. Information about the full FOV 3250 is collected when the detector 3220-source 3210 system rotates 360 degrees. Although this technique using offset detector geometry is well known for a CBCT system such as system 3200, the ability to use both centered and offset detector geometry in the same CBCT system only works when there is no 2D antiscatter grid present on the detector 3220 side.

FIG. 34A again presents the 2D ASG of FIG. 1. In the illustrated embodiment, the 2D antiscatter grid (ASG) 3410 according to the present technology is on a side of the x-ray detector 3220 that faces the x-ray source 3210 during use. In some embodiments, the 2D ASG 3410 according to the present technology may be a 2D array of through-holes separated by metal, preferably tungsten, septa. The 2D ASG 3410 may be placed on the detector 3210 to reduce scattered x-ray radiation and thereby improve image quality.

Figure 34B:
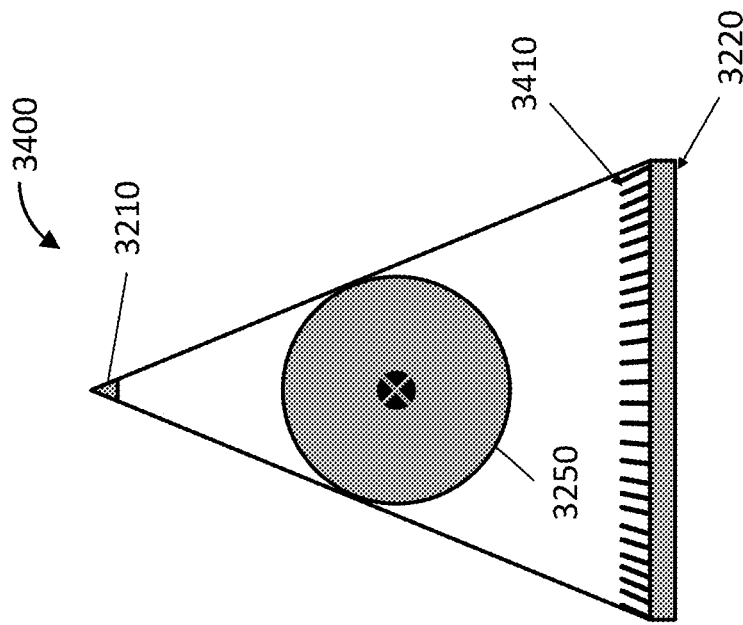
FIG. 34B presents a schematic diagram of an x-ray imaging system according to some embodiments of the present technology.

FIG. 34B presents a schematic diagram of an x-ray imaging system 3400 according to some embodiments of the present technology. As used in CBCT for example, each through-hole of the 2D ASG 3410 may need to be aligned to angularly face the x-ray source 3210 so that x-rays emitted by the source 3210 can go through the holes of the 2D ASG 3410. Thus, in practice, particular manufactures of the 2D ASG 3410 according to the present technology may need to be customized based on a particular detector 3220-x-ray source 3210 geometry. In the example shown in FIG. 34B, the 2D ASG 3410 is tailored for the above described centered detector CBCT geometry. Accordingly, the through-holes of the 2D ASG 3410 are designed to point towards the x-ray source 3210 to match the divergence of the x-rays emitted from the source 4320 during use. However, if the detector 3220 is shifted laterally to increase the FOV 3250, as in the offset detector CBCT geometry and associated techniques described above with reference to FIG. 33, the 2D ASG 3410 will no longer be aligned towards the x-ray source 3210.

Figure 35:
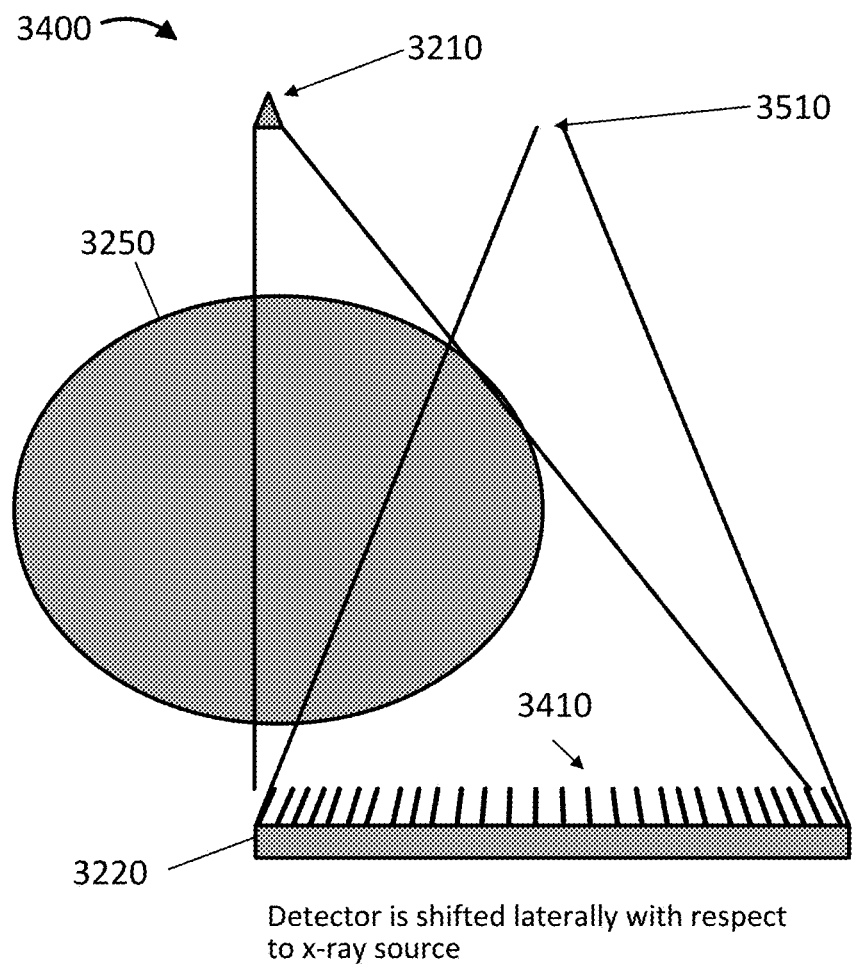
FIG. 35 presents the system shown in FIG. 34B where the 2D ASG according to the present technology is shifted laterally.

FIG. 35 presents the system 3400 shown in FIG. 34B where the 2D ASG 3410 according to the present technology is shifted laterally. When the detector is shifted laterally, the 2D ASG 3410 would be focused towards a point 3510 in space where the x-ray source 3210 is not present. Given the lack of full alignment, x-rays emitted by the source 3210 will not go through the holes of the 2D ASG 3410 as desired and since not all x-ray radiation will reach the detector 3210 the image quality will suffer. Thus, if a CBCT system like system 3400 uses both centered and offset detector geometries, it will need two different 2D grids—one designed for centered detector, and another one for offset detector geometry. Having separate 2D grids for each geometry can present challenges in practice. The method described in this Example 11 provides a technique to address this challenge.

Figure 36:
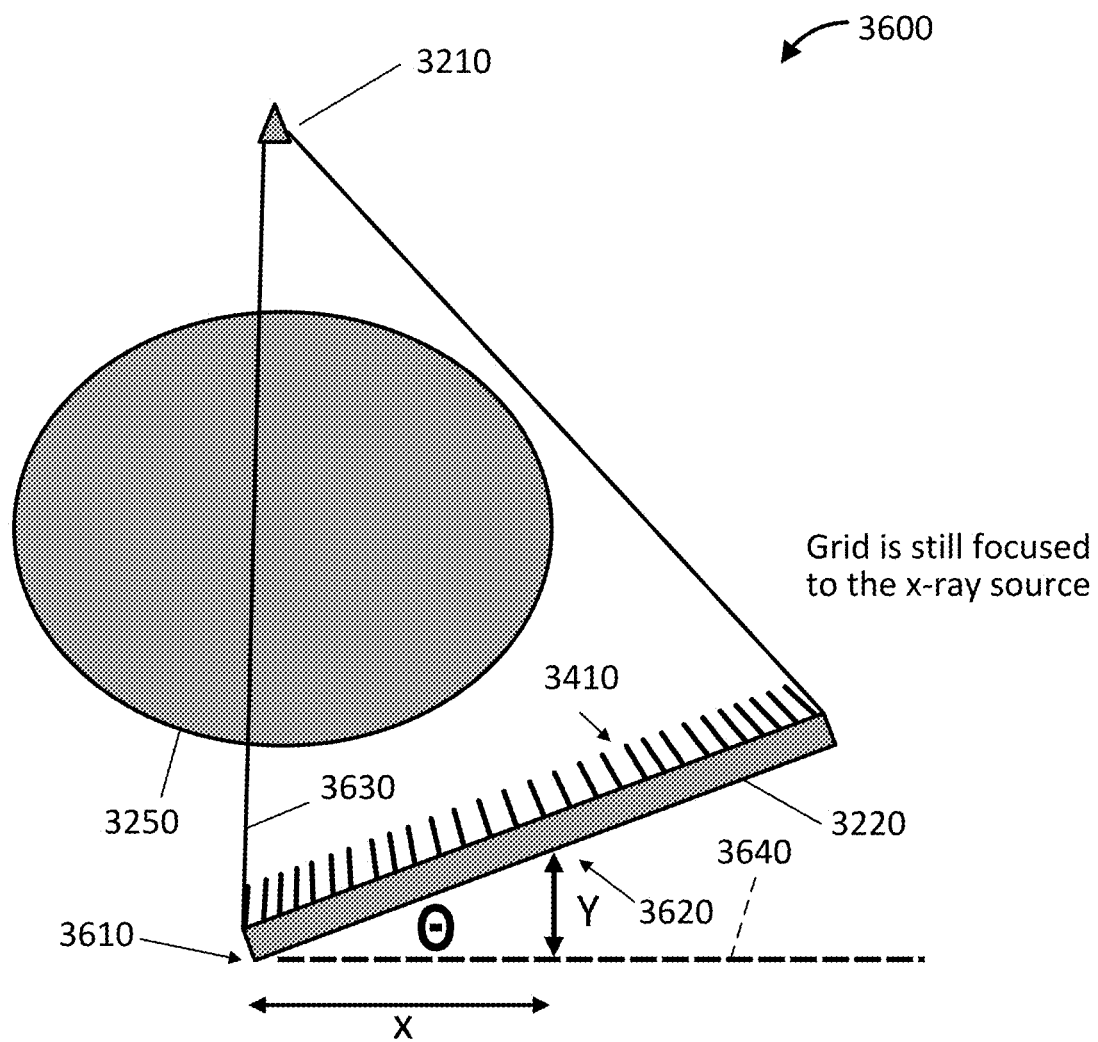
FIG. 36 presents an x-ray imaging system 3600 according to some embodiments of the present technology.

FIG. 36 presents an x-ray imaging system 3600 according to some embodiments of the present technology. In some embodiments, system 3600 may be a CBCT imaging system. The technique depicted in FIG. 36 starts with the 2D ASG 3410 designed for centered detector geometry, as shown and described above. Therefore, centered detector CBCT imaging can be performed without encountering the aforementioned technical challenges. When the same single 2D ASG 3410 is to be used with offset detector CBCT, the method according to the present technology may utilize the lateral shifting along with a tilting of the detector 3220. This tilting moves the detector 3220 closer to the x-ray source 3220, such that the septa (and/or through-holes thereof) of the 2D ASG 3410 are all still focused towards the x-ray source 3210.

If the detector 3220 is shifted laterally by a first distance (denoted as "x" in FIG. 36) for offset geometry, the detector 3220 needs to be tilted by an angle (denoted as theta "θ" in FIG. 36) so that a shifting by a second distance (denoted as "y" in FIG. 36) provides the alignment of the through-holes of the 2D ASG 3410 toward the x-ray source 3210. In the embodiment of system 3600 shown in FIG. 36, one end of the detector 3220 defines the tilting origin 3610 for angle θ, the first distance (x) is defined between a center 3620 of the detector 3220 and a normal line 3630 from the center 3620 to the x-ray source of the initial centered detector CBCT configuration, and the second distance (y) is defined between a reference plane 3640 and the center 3620, with plane 3640 being orthogonal to line 3630.

Figure 37A:
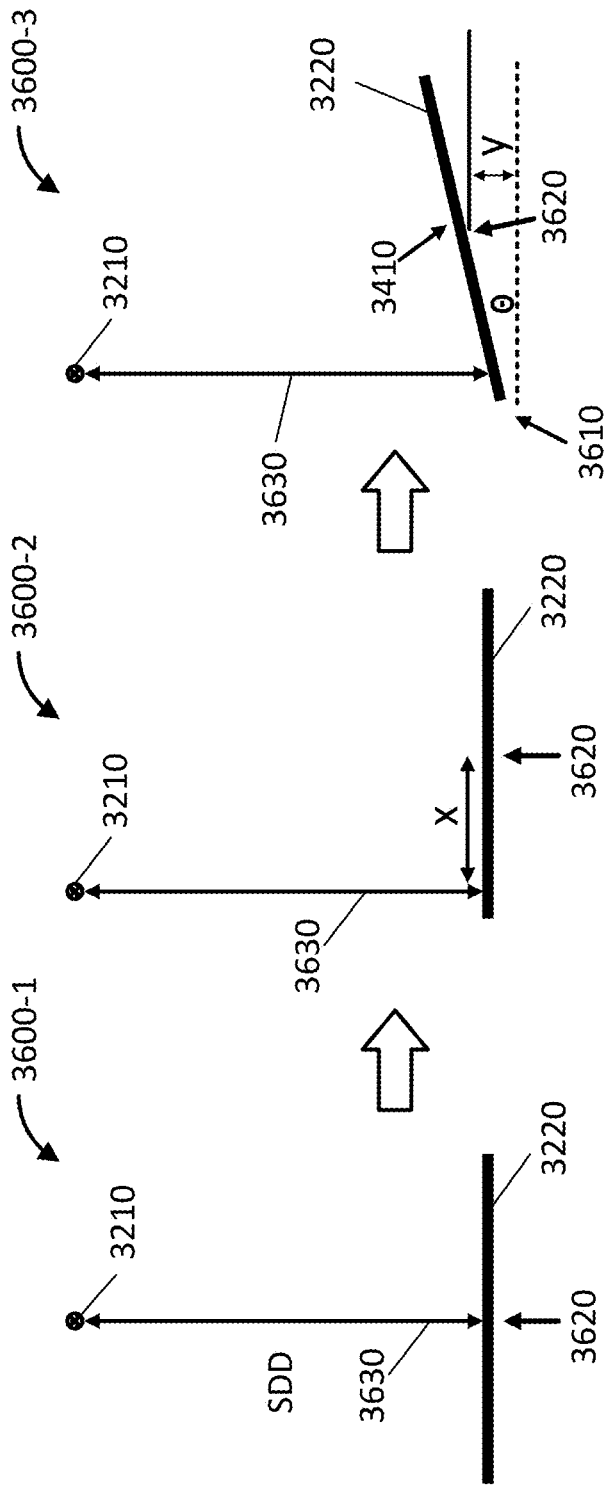
FIG. 37A presents a schematic diagram providing additional details for the shifting and tilting technique described above for the system of FIG. 36.

FIG. 37A presents a schematic diagram providing additional details for the shifting and tilting technique described above for the system 3600 of FIG. 36. With the system 3600 in the initial centered detector CBCT configuration (e.g., 3600-1), a length of the normal line 3630 between the x-ray source 3210 and the center 3620 of the detector 3220 is denoted as "SDD" (source to detector distance) in FIG. 37A. SDD is the shortest distance on the virtual line 3620 that is connecting the x-ray source 3210 to the detector 3220. This normal line 3630 is also orthogonal to the detector entrance surface. From the initial state 3600-1, the detector 3220 may be laterally shifted by the amount x to take on the state labeled 3600-2 in FIG. 37A. As discussed above with reference to FIG. 36, the septa (and/or through-holes thereof) of the 2D ASG 3410 are not fully aligned with the x-rays emitted by the source 3210 in the state 3600-2. In the technique according to the present technology, a third state 3600-3 of the system 3600 may include the detector 3220 being tilted by the angle θ, which results in the center 3620 of the detector 3220 being shifted upward by the distance y.

The values of angle θ and the distance y are functions of the SDD and the value of x, as shown in equations (1) and (2), below:

$$\theta(\text{tilt angle of detector 3220}) = \arcsin\frac{x}{SDD} \quad (1)$$

$$y(\text{upward movement of the center of the detector}) = SDD - \sqrt{SDD^2 - x^2} \quad (2)$$

As a result of the tiling by angle θ after the lateral shifting, the system in its state 3600-3 has the septa (and/or through-holes thereof) of the 2ASG 3410 of the detector 3220 fully aligned with the x-rays emitted by the source 3210 during operation of system 3600.

Figure 37B:
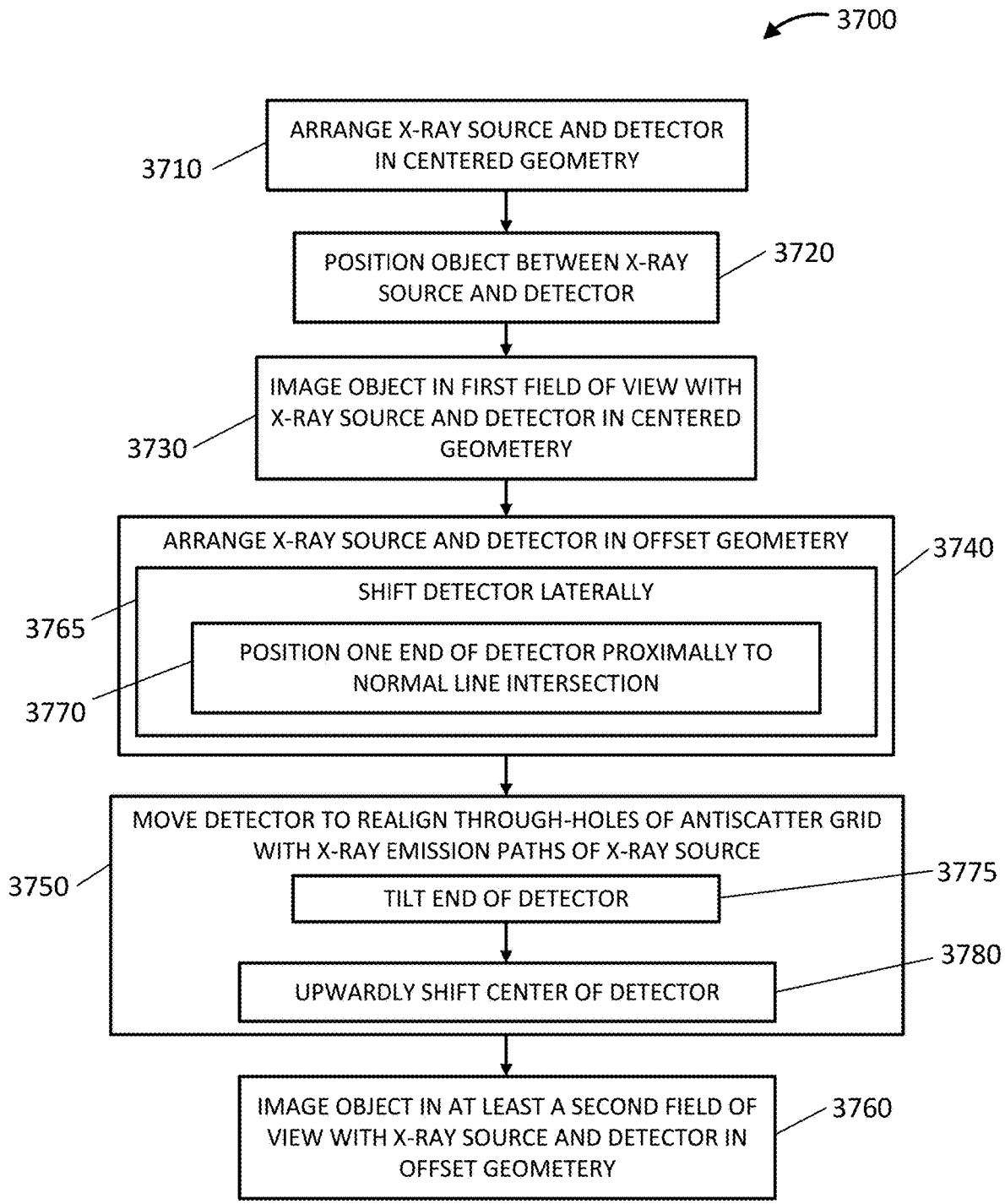
FIG. 37B presents a flowchart of a method to improve (or assure) alignment of an antiscatter grid when the detector is shifted with respect to the x-ray source, according to some embodiments of the present technology.
Figure 38A:
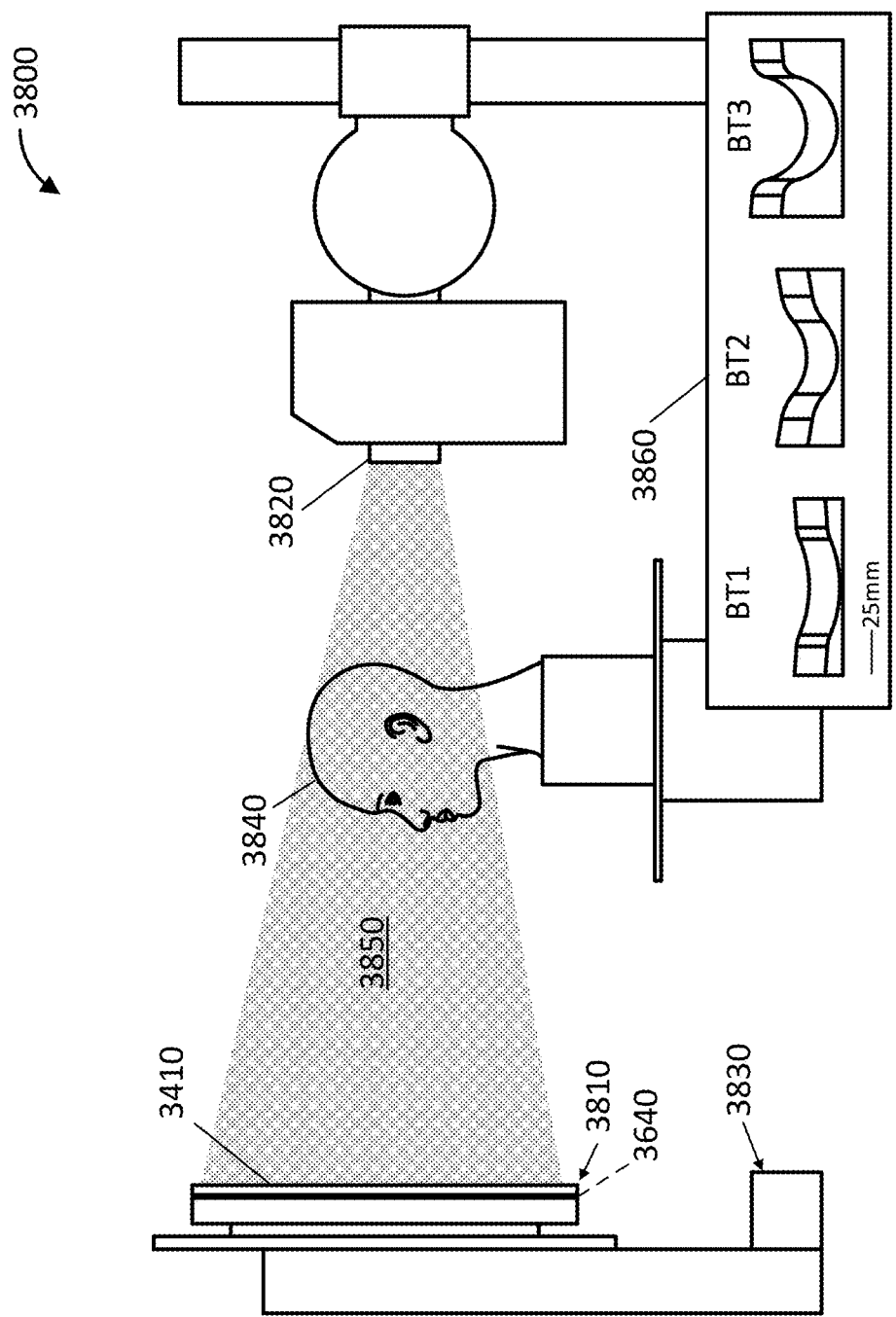

FIG. 37B presents a flowchart of a method 3700 to improve (or assure) alignment of an antiscatter grid when the detector is shifted with respect to the x-ray source, according to some embodiments of the present technology. With further reference being made to FIGS. 35, 36 and 37A, method 3700 may include the step of arranging 3710 x-ray source 3210 and detector 3220 having an ASG in the above described centered geometry. In some embodiments, detector 3220 as used in method 3700 may be a flat panel detector. In some embodiments, the ASG of the detector 3220 may be a 2D ASG (e.g., 3410) as described herein according to the present technology. In other embodiments, the ASG of detector 3220 may be a 1D ASG. Notably, method 3700 may be performed for the advantageous technical benefits as described herein in either the case of a 1D ASG or a 2D ASG.

In the centered geometry, through-holes of the ASG may be aligned with x-ray emission paths of the x-ray source 3210. Method 3700 may include the step of positioning 3720 an object between detector 3220 and x-ray source 3210. In one embodiment, the positioning 3720 step of method 3700 may be performed after the arranging 3710 step. In other embodiments, the positioning 3720 step of method 3700 may be performed before the arranging 3710 step.

Method 3700 may include the step of imaging 3730 the object in a first FOV with the detector 3220 and x-ray source 3210 arranged 3710 in the centered geometry. With the object imaged 3730 in the first FOV, method 3700 may include the step of arranging 3740 the x-ray source 3210 and the detector 3220 in the above described offset geometry. In the offset geometry, through-holes of the ASG may be at least partially unaligned with the x-ray emission paths of the x-ray source 3210. With the source 3210 and detector 3220 arranged 3740 in the offset geometry, method 3700 may include the step of moving 3750 the detector 3220 to realign the through-holes of the ASG with the x-ray emission paths of the x-ray source 3210. With the detector 3220 so moved 3750, method 3700 may include the step of imaging 3760 the object in at least a second FOV.

In some embodiments, the arranging 3740 step of method 3700 may include shifting 3765 the detector 3220 laterally by the first distance x, as described above with reference to FIGS. 35, 36 and 37A. The laterally shifting 3765 step of method 3700 may include positioning 3770 one end (e.g., at the point labeled 3610) of the detector 3220 proximal to an intersection of the normal line 3630 defined from the x-ray source 3210 and the reference plane 3640 of the detector 3220 and having a length SDD, as shown in FIGS. 36 and 37A.

In one embodiment of method 3700, the moving 3750 of method 3700 includes tilting 3775 the detector 3220 upwardly toward the x-ray source 3210 by the angle θ, where θ has its origin 3610 at the aforementioned one end of the detector 3220. In the embodiment, the moving 3750 of method 3700 also includes upwardly shifting 3780, e.g., as a result of the tilting 3775, the center 3620 of the detector 3220 by the second distance y, as described above with reference to FIGS. 36 and 37A.

Example 12

Figure 34A:
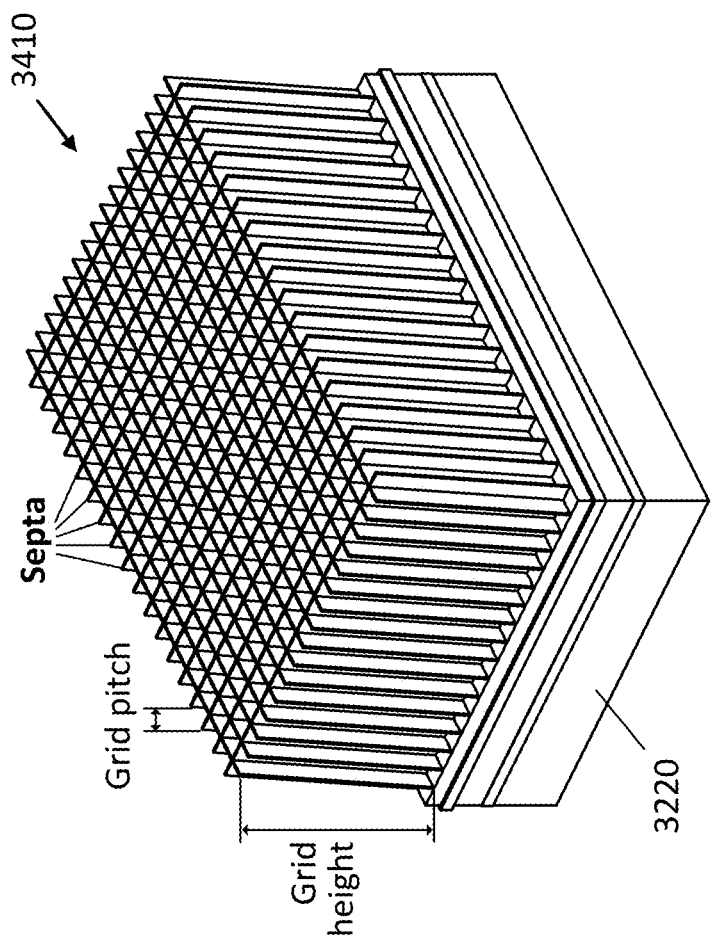
FIG. 34A again presents the 2D ASG of FIG. 1.

FIGS. 38A-38D present an x-ray imaging system 3800 utilizing a flat panel detector (FPD) 3810 with a 2D ASG (e.g., 3410 as shown in FIG. 34A), according to some embodiments of the present technology. In the illustrated embodiments of FIG. 38A-38D, the FPD 3810 may be embodied in, for example and without limitation, a 40×30 cm FPD. In some embodiments, system 3800 may be a CBCT imaging system. With further reference being made to FIGS. 34A-37B, system 3800 may include FPD 3810 and an x-ray source 3820. X-ray source 3820 may include one or more bow tie filters 3860 (e.g., BT1, BT2 and/or BT3). When energized, x-ray source 3820 may emit x-ray radiation according to an x-ray emission path 3850. System 3800 may thus be employed for generating x-ray images of an object 3840 positioned in the x-ray emission path 3850.

System 3800 may include a rotation and translation stage 3830. In some embodiments, the rotation and translation stage may include the FPD 3810 with its associated 2D ASG 3410. The FPD 3810 may define the above-described reference plane 3640. FIG. 38B depicts system 3800 with the FPD 3810 and x-ray source 3820 positioned with respect to one another in the above-described centered geometry. FIG. 38C depicts system 3800 with the FPD 3810 and x-ray source 3820 positioned with respect to one another in the above-described offset geometry.

Referring now to FIGS. 38B-38D, the rotation and translation stage 3830 may include rotation means 3870 operably coupled to the FPD 3810. For example and without limitation, the rotation means 3870 may include, or be embodied in, a motor and associated mechanism (e.g., gears) operably coupled to a portion of FPD 3810 (e.g., proximal to the center 3620 of the FPD 3810), and configured to, or otherwise capable of, rotating the FPD 3810 in a clockwise 3875 and/or counter-clockwise 3880 direction relative to an axis z, as shown in FIG. 38B. In examples of the present technology where rotation means 3870 includes, or is embodied in, a motor, means 3870 may be further operably coupled (e.g., by a wired electrical connection) to a motor controller and/or driver 3885 that can regulate a magnitude and/or polarity of an electric current to means 3870 to thereby control a speed and/or direction of rotation of a motor shaft thereof.

In some embodiments, the rotation and translation stage 3830 may include lateral shifting means 3890 operably coupled to the FPD 3810. For example and without limitation, the lateral shifting means 3890 may include, or be embodied in, a motor and associated mechanism (e.g., gears) operably coupled to a portion of FPD 3810, and configured to, or otherwise capable of, laterally shifting the FPD 3810 in alternate directions along an axis x, as shown in FIG. 38C. The embodiment shown in FIG. 38C illustrates a resulting lateral shifting using means 3890 by the first distance x as between the FPD 3810 center 3620 and the normal line 3630. In examples of the present technology where lateral shifting means 3890 includes, or is embodied in, a motor, means 3890 may be further operably coupled (e.g., by a wired electrical connection) to the motor controller and/or driver 3885 that can regulate a magnitude and/or polarity of an electric current to means 3890 to thereby control a speed and/or direction of rotation of a motor shaft thereof.

In some embodiments, the rotation and translation stage 3830 may include upwardly shifting means 3895 operably coupled to the FPD 3810. For example and without limitation, the upwardly shifting means 3895 may include, or be embodied in, a motor and associated mechanism (e.g., linear actuator 3897) operably coupled to a portion of FPD 3810 (e.g., proximal to the center 3620 of the FPD 3810), and configured to, or otherwise capable of, upwardly shifting the center 3620 of FPD 3810 in alternate directions (e.g., upward and downward) along an axis y, as shown in FIG. 38D. In examples of the present technology where upwardly shifting means 3895 includes, or is embodied in, a motor, means 3895 may be further operably coupled (e.g., by a wired electrical connection) to the motor controller and/or driver 3885 that can regulate a magnitude and/or polarity of an electric current to means 3895 to thereby control a speed and/or direction of rotation of a motor shaft thereof. In some embodiments, upward shifting of FPD 3810 by the second distance y using means 3895 results in tilting FPD 3810 upwardly by the aforementioned angle $\theta$ with respect to reference plane 3640.

In some embodiments of the present technology, the system 3800 as discussed above in this Example 12 may be utilized to, at least in part, implement or otherwise perform one or steps of the method 3700 as described above in Example 11.

Example 13

The present technology is also pertinent to portable or compact x-ray imaging systems that employ the disclosed 2D ASG (e.g., 3410). As described in this Example 13, a portable or compact CT scanner and associated methods may be provided that provides superior imaging quality as compared to known portable or compact CT scanners.

FIGS. 39A-39F present a compact or portable CT scanner system 3900 presents utilizing an FPD 3920 with a 2D ASG as shown in FIG. 34A (e.g., 2D ASG 3410), according to some embodiments of the present technology. CT scanner system 3900 includes an x-ray source 3910 positioned on and operably coupled to an O-shaped gantry 3930. System 3900 also includes the FPD 3920 positioned on and operably coupled to the O-shaped gantry 3930. The O-shaped gantry 3930 defines an opening 3945 having a center axis 3980 into which an object 3940 to be imaged may be positioned. FPD 3920 includes the 2D ASG 3410 which faces the opening 3945. In some embodiments, a diameter of the opening 3945 may be 35-45 cm, suitable for imaging of head and neck region, and extremities, or human patients. To scan the human torso, bore diameter can be increased.

In some embodiments, the x-ray source 3910 is positioned radially opposite the FPD 3920 on the O-shaped gantry 3930. System 3900 may include a controller or computer 3990 operably coupled to x-ray source 3910 and/or FPD 3920. System 3900 may also include means (not shown in FIGS. 39A-39F) for rotating the O-shaped gantry 3930 in a clockwise 3960 and/or counterclockwise 3970, annular (e.g., circumferential) direction. For example and without limitation, the means for rotating the O-shaped gantry 3930 may include, or be embodied in, a motor and associated mechanism (e.g., gear(s) or belt(s)) operably coupled to a portion of O-shaped gantry 3930 (e.g., proximal to the outer circumference of O-shaped gantry 3930), and configured to, or otherwise capable of, causing the entire O-shaped gantry to rotate about the center axis 3980 in alternate directions (e.g., clockwise and counterclockwise). In examples of the present technology where the means for rotating the O-shaped gantry 3930 includes, or is embodied in, a motor, such means may be further operably coupled (e.g., by a wired electrical connection) to the controller or computer 3990 that can regulate a magnitude and/or polarity of an electric current to the means to thereby control a speed and/or direction of rotation of a motor shaft thereof. In some embodiments, rotation of the O-shaped gantry 3930 causes the radial alignment of the x-ray source 3910 and the FPD 3920 to be maintained at all times during the rotation such that an x-ray emission path 3950 from source 3910 to FPD 3920 beneficially passes through all the septa (and/or through holes thereof) of 2D ASG 3410, as described above in Example 12, for instance.

The O-shaped gantry 3930 may be positioned in a correspondingly shaped housing 3955. The O-shaped gantry 3930 may include a pair of spindles 3975 positioned radially opposite one another. In some embodiments, system 3900 may be an assembly of a base 3925, two stanchions 3915 and a set of wheels 3935 coupled to the base 3925. In one example, spindles 3975 may extend through the housing 3955 and be rotatably coupled to the stanchions 3915. In another example, the housing 3955, but not also the O-shaped gantry 3930, includes the spindles 3975.

System 3900 may also include means (not shown in FIGS. 39A-39F) for rotating the O-shaped gantry 3930 and/or housing 3955 in a clockwise 3965 and/or counterclockwise 3985, radial direction. For example and without limitation, the means for rotating the O-shaped gantry 3930 and/or housing 3955 may include, or be embodied in, a motor and associated mechanism (e.g., gear(s) or belt(s)) operably coupled to a portion of O-shaped gantry 3930 and/or housing 3955 (e.g., proximal to the outer circumference of O-shaped gantry 3930 and/or housing 3955), and configured to, or otherwise capable of, causing the entire O-shaped gantry and/or housing 3955 to rotate about a radial axis 3905 in alternate directions (e.g., clockwise and counterclockwise).

In examples of the present technology where the means for rotating the O-shaped gantry 3930 and/or housing 3955 includes, or is embodied in, a motor, such means may be further operably coupled (e.g., by a wired electrical connection) to the controller or computer 3990 that can regulate a magnitude and/or polarity of an electric current to the means to thereby control a speed and/or direction of rotation of a motor shaft thereof. In some embodiments, rotation of the O-shaped gantry 3930 causes the radial alignment of the x-ray source 3910 and the FPD 3920 to be maintained at all times during the rotation such that an x-ray emission path 3950 from source 3910 to FPD 3920 beneficially passes through all the septa (and/or through-holes thereof) of 2D ASG 3410, as described above in Example 12, for instance.

The CT scanner system 3900 according to the present technology is portable and may also be fabricated in an ultracompact design given that FPD 3920 with the 2D ASG 3410 is included. Embodiments of the present technology that provide for rotation of the O-shaped gantry and thus also the x-ray source 3910 and the FPD 3920 about radial axis 3905 represents a substantial advance in the state of the art as known portable CT scanners do not have this gantry tilting capability.

Scattered radiation is a major cause of image quality degradation in known flat panel detector-based CT scanner. The use of the 2D ASG 3410 according to the present technology addresses this problem, and allows the use of FPD 3920 in CT for soft tissue imaging. The wheels of system 3900 enable it to be transported from one room to another. Suitable power supply electronics may be positioned in the base 3925, for instance. In some embodiments, system 3900 according to the present technology may be fitted into land, sea, or air vehicles for use by first responders. The controller 3990 may further include, or be operably coupled to, communications and networking components 3992, such that imaging data may be transmitted to clinician workstations or computing devices 3996 positioned remote from the system 3900 for such advantageous technical effects as enabling telemedicine support via a communications network 3998 (e.g., Internet, satellite, cellular, etc.).

The portable and, in some embodiment, ultracompact CT scanner system 3900 according to the present technology may be employed for x-ray imaging of extremities, the head, and/or back of patients. The dimensions of system 3900 and its various component parts may be scaled up to provide CT scanning capability for the human torso. The FPD 3920 of system 3900 may include, or be embodied in, an energy integrating or photon counting detector. In some embodiments, and area of the FPD 3920 may be 20 cm×30 cm. In other embodiments, the area of FPD 3920 may be from 20 cm×20 cm to 43 cm×43 cm.

In some embodiments, dimensions of FPD 3920 may be beneficially minimized to, for example and without limitation, thereby enable a more compact CT scanner system 3900 by utilizing the offset detector geometry, such as is described above in Example 12. The offset detector geometry may allow for coverage of a larger FOV with a smaller FPD 3920.

In some embodiments, the CT scanner system 3900 according to the present technology may be used to implement, at least in part, any or all of the steps of the method 3700 as described above with reference to FIG. 37B in Example 12, for instance. In such example implementations, a positioning technique such as the method 3700 may enable switching the FPD 3920 and thus also the 2D ASG 3410 of system 3900 from the centered detector geometry to the offset detector geometry to thereby enable more compact dimensions and variable imaging applications and FOVs depending upon a specific clinical need at hand.

In some embodiments of system 3900, a separation distance (e.g., pitch) between two adjacent vertical walls of the 2D ASG 3410 may be from 0.8 mm to 3 mm. A grid ratio of the 2D ASG 3920 in system 3900 may be from 4 to 16. The pitch of the 2D ASG 3410 can be different from a detector pixel pitch of the FPD 3920. For example, and without limitation, the pitch of the 2D ASG 3410 may be 2 mm and the detector pixel pitch of FPD 3920 may be 0.35 mm. In another embodiment, the pitch of the 2D ASG 3410 may be 2 mm and the detector pixel pitch of FPD 3920 may be 0.2 mm.

In some embodiments, the grid pitch of 2D ASG 3410 may be larger than the detector pixel pitch of FPD 3920. In system 3900, the vertical walls of 2D ASG 3410 may be formed at least in part of a radiation-opaque, or at least radiation-absorbing, material such as a metal. As installed in embodiments of the CT scanner system according to the present technology, the vertical walls that define septa (and/or through-holes thereof) of 2D ASG 3410 may be aligned toward a focal spot of the x-ray source providing an x-ray emission path 3950 for use in imaging the object 3940 positioned in the opening 3945. Such alignment may be provided in system 3900 by the O-shaped gantry 3930 configuration having the aforementioned centered geometry, or alternatively or additionally by the O-shaped gantry 3930 incorporating in the techniques of method 3700 according to the present technology.

In some embodiments, the vertical walls defining septa (and/or through-holes thereof) of 2D ASG 3410 may be at least partially unaligned with the detector pixels of FPD 3920. For example, and without limitation, the vertical walls of 2D ASG 3410 need not be parallel to the detector pixel array of FPD 3920. However, in other embodiments, the vertical walls of 2D ASG 3410 can be aligned with the detector pixel array of PFD 3920.

In some embodiments of system 3900, as well as of system(s) 3600 and/or 3800 described above in Example 12, the 2D ASG 3410 may be fabricated as a single module. Alternatively, the 2D ASG 3410 may be fabricated as smaller modules that can be integrated together. In some embodiments, the 2D ASG 3410 may be placed directly on the x-ray absorbing sensor layer of FPD 3920. In other embodiments, a gap may exist between 2D ASG 3410 and the x-ray absorbing sensor layer of FPD 3920. As used in one or more of system(s) 3600 and 3800 according to the present technology, the 2D ASG 3410 may include any of the various design features disclosed herein to provide a number of advantageous technical effects to clinicians performing diagnostic x-ray imaging for the benefit of human or veterinarian patients.

Figure 39A:
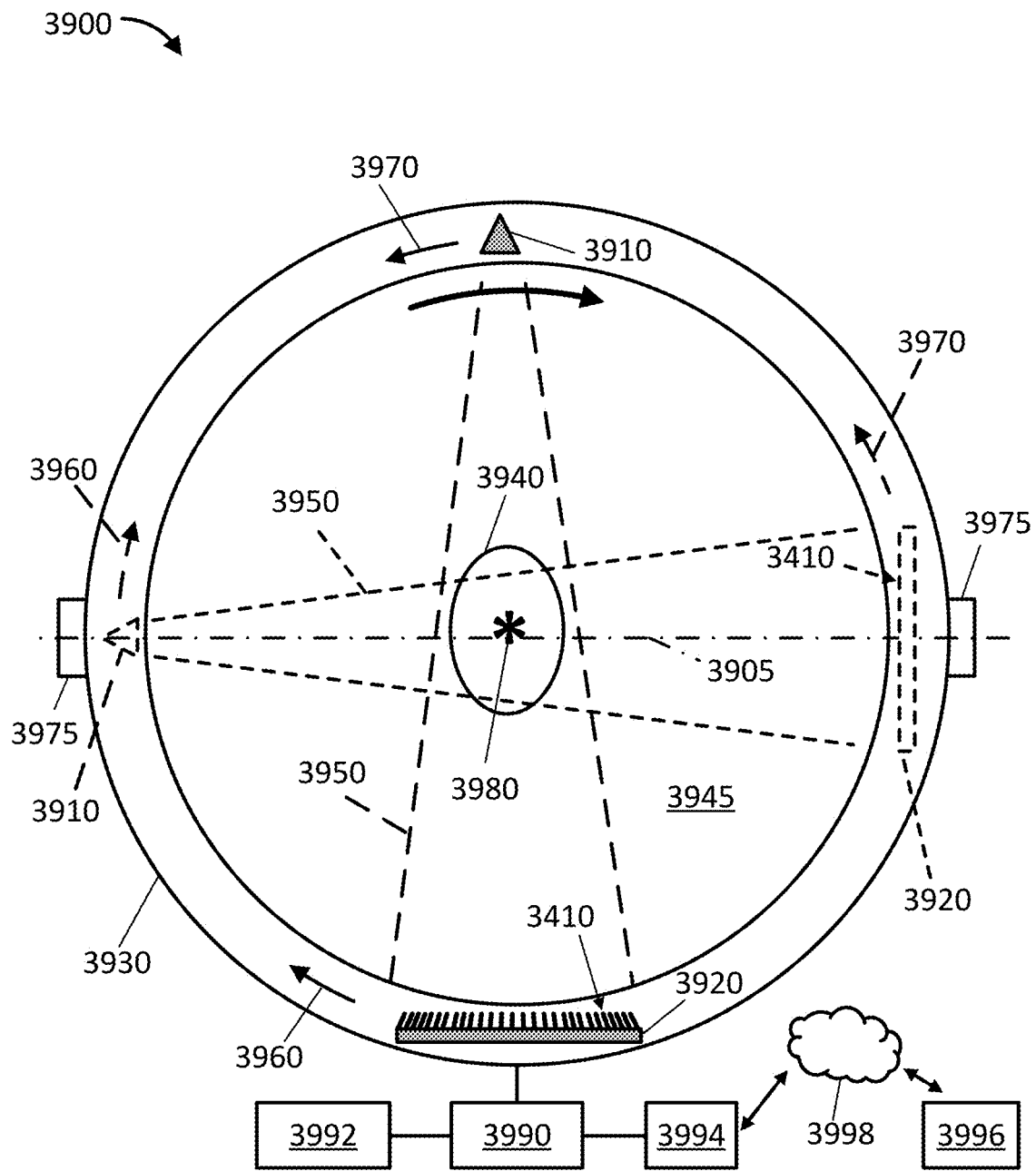
FIGS. 39A-39F present a compact or portable CT scanner system presents utilizing a flat panel detector (FPD) with a 2D ASG as shown in FIG. 34A, according to some embodiments of the present technology.
Figures 39B, 39C:
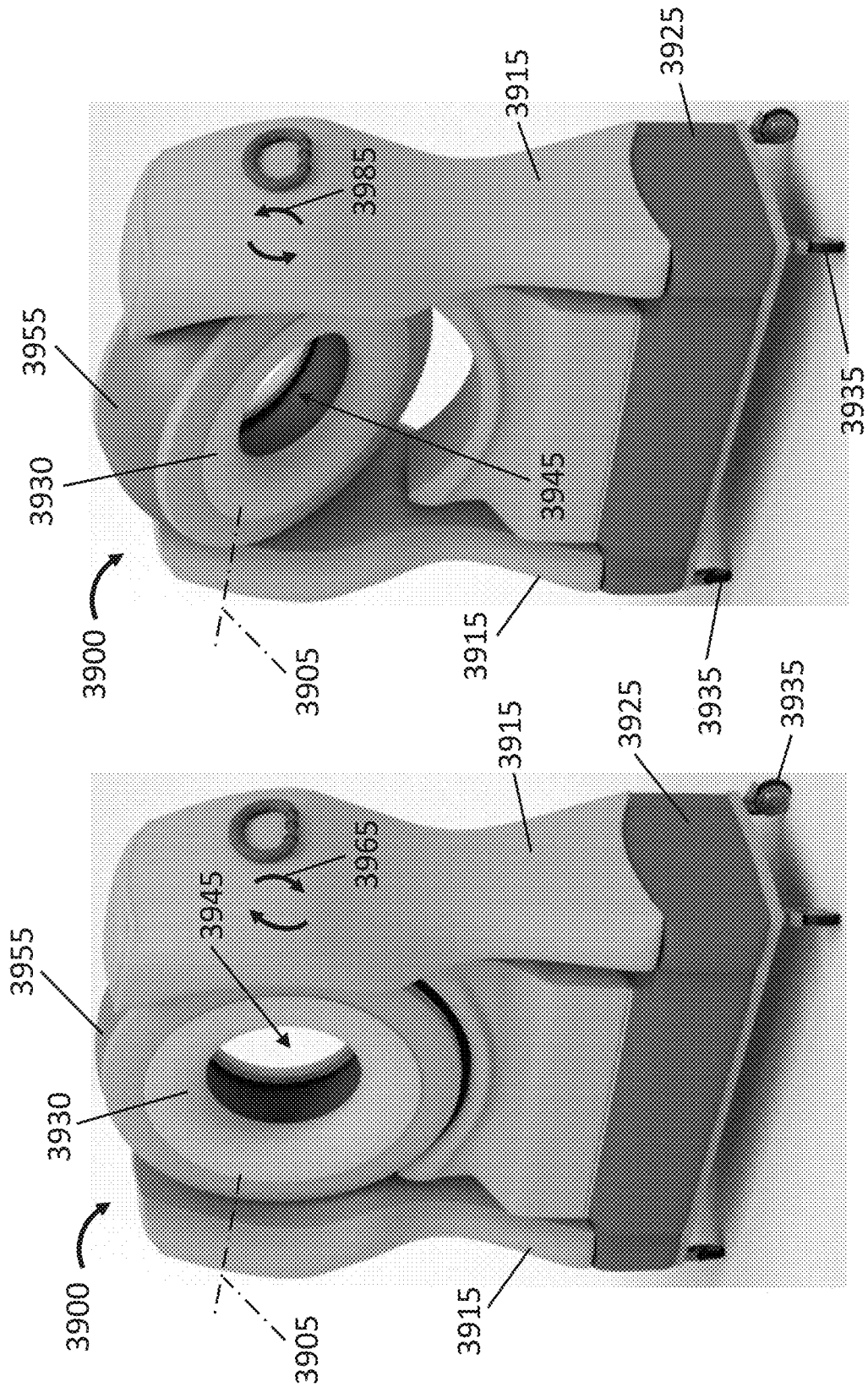
Figure 39D:
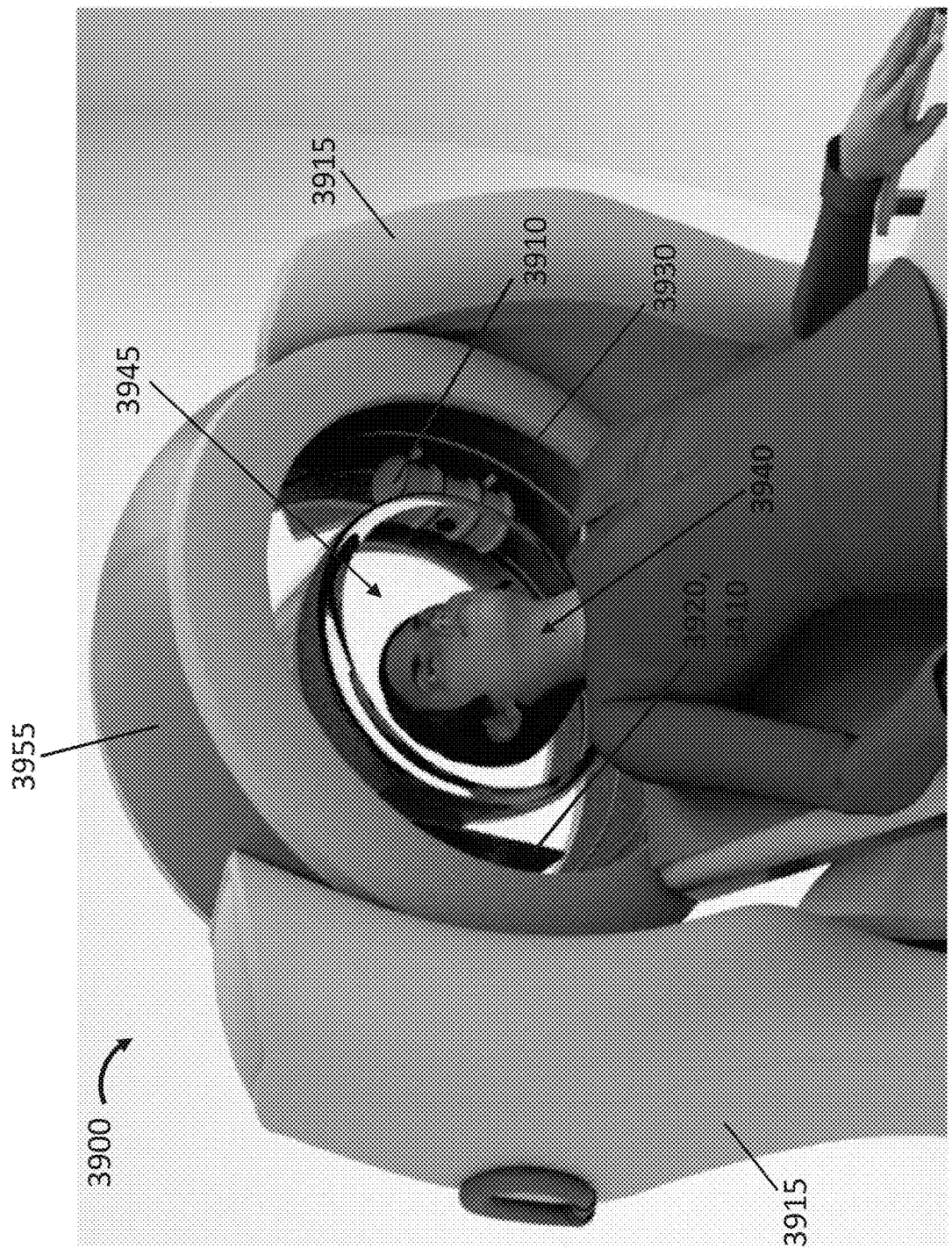
Figure 39F:
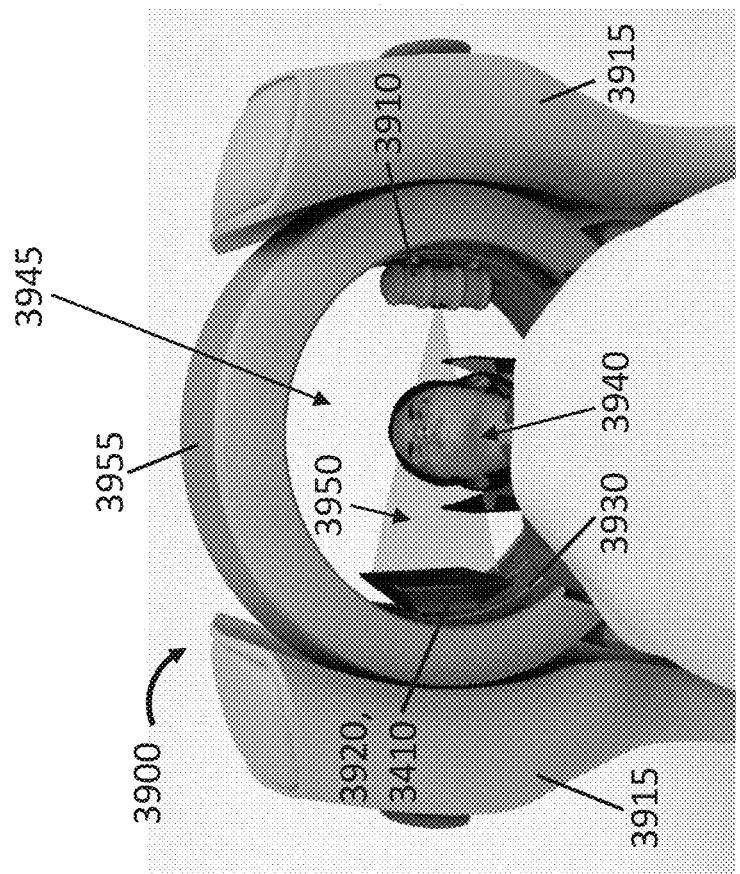
Figure 39E:
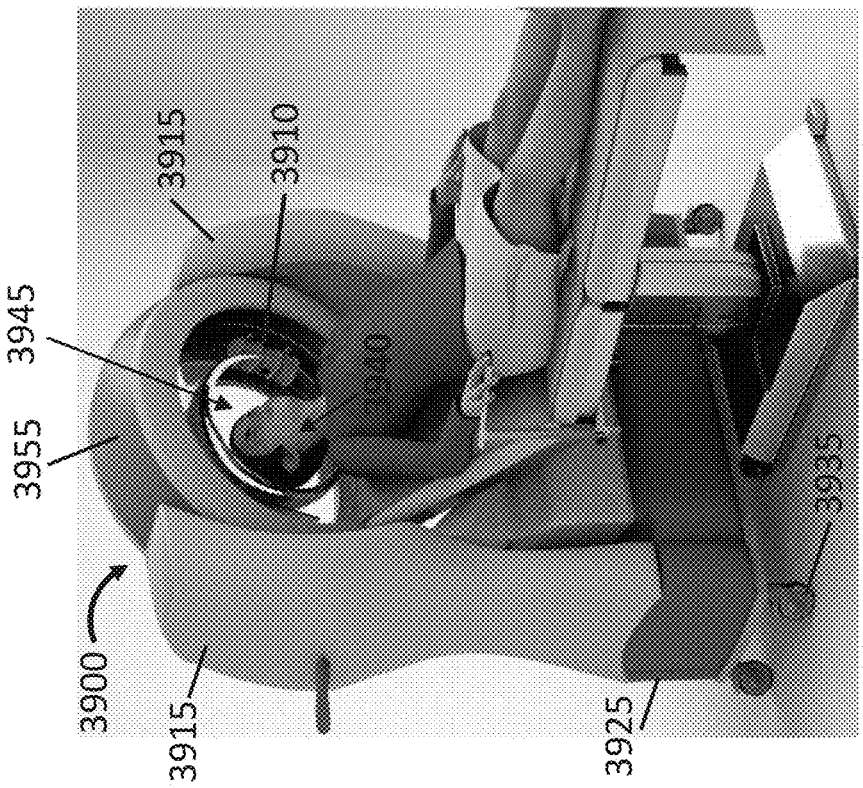
Figure 39G:
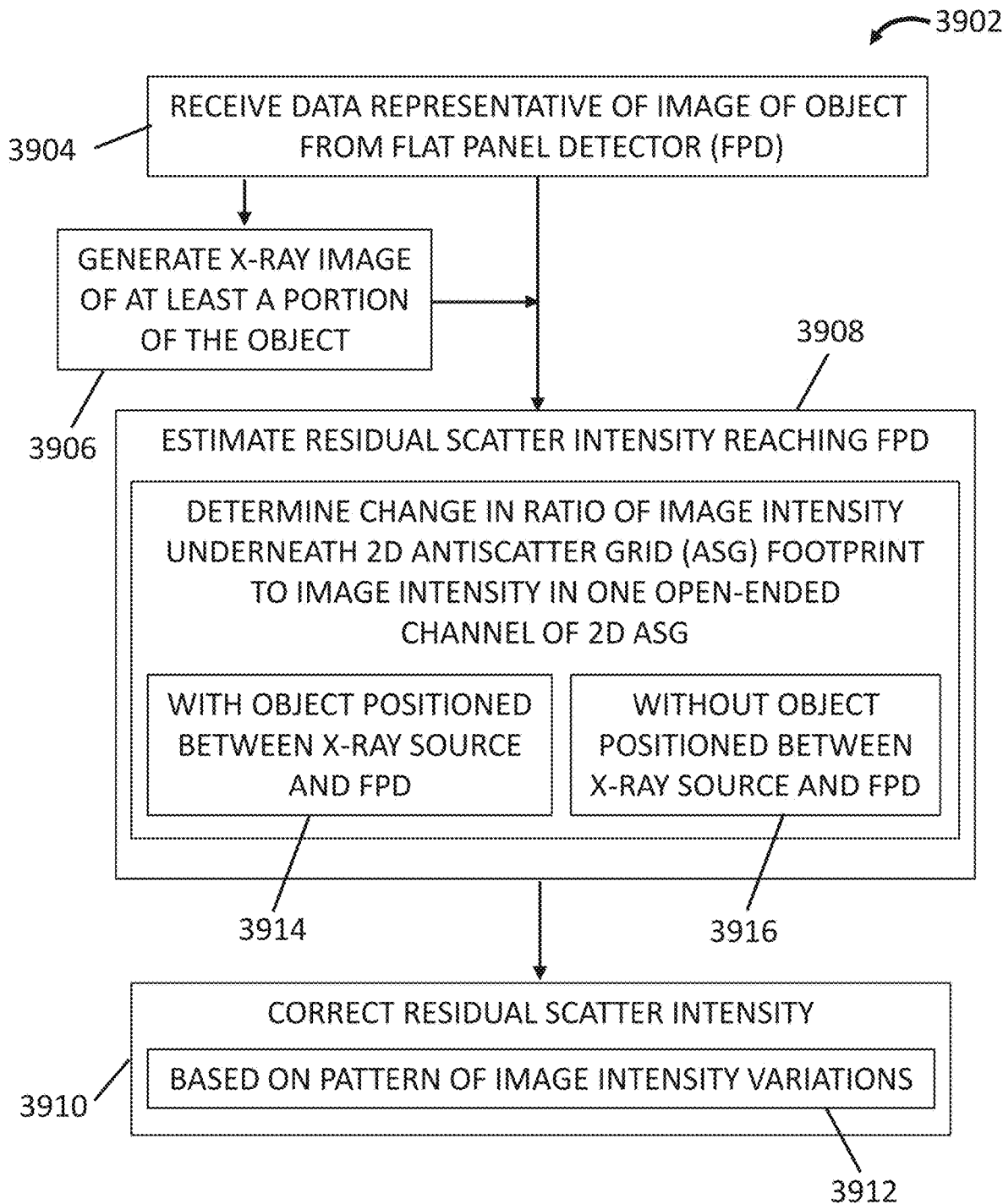
FIG. 39G presents a method for processing x-ray images that may be used with the system of FIGS. 39A-39F, according to some embodiments of the present technology.

In some embodiments, the controller or computer 3990 of system 3900 may be programmed, or otherwise configured, to perform or implement at least in part any or all of the image processing methods and techniques as described herein according to the present technology. FIG. 39G presents a method 3902 for processing x-ray images that may be used with the system 3900 of FIGS. 39A-39F, according to some embodiments of the present technology.

Method 3902 provides an image data correction process that may be utilized with, for example and without limitations, one or more of the system(s) 3600, 3800 and 3900 according to the present technology. Method 3902 may, in some embodiments, be further employed with any of the various x-ray imaging devices and systems disclosed herein. A 2D ASG (e.g., 3410) may not stop all scattered x-rays. Some of the scattered x-rays from an x-ray source (e.g., 3910) may be transmitted through the 2D ASG. This issue is address by method 3902 according to the present technology with a residual scatter correction process. Correction of the residual scatter intensity according to the present technology may be accomplished, at least in part, by measuring signal intensity variations in the FPD or detector pixel array to facilitate an improvement in the quality of the x-ray image Method 3902 may minimize or otherwise advantageously reduces image artifacts in CT scanner images that can be introduced by a 2D ASG (e.g., 3410) associated with an x-ray detector (e.g., FPD 3410).

In CT and CBCT systems, gantry flex can result a change in position of the x-ray source in relation to the x-ray detector while the gantry is rotating around the patient during a CT scan. Gantry flex can degrade the performance of x-ray imaging techniques. Use of an O-shaped gantry (e.g., 3930) can mitigate and suppress the gantry flex effect. Accordingly, method 3902 may be uniquely suited to use with x-ray imaging systems that include an O-shaped gantry (e.g., system 3900).

An O-shaped gantry is structurally more robust as compared to a C-shaped gantry, thereby minimizing the negative effects of x-ray imaging arising from gantry flex. C-shaped gantry may be utilized with known portable and/or compact x-ray imaging devices and devices for the space-saving benefits. Yet, O-shaped gantries tend to take up more space and may be heavier than systems using C-shaped gantries. The incorporation of the FPD 3920 and 2D ASG 3410 in the system 3900 according to the present technology has hitherto not been considered in the art for at least these reasons, and as described in greater detail below, the results in terms of imaging quality from a compact and/or portable x-ray imaging system according to the present technology are unexpected. As further described below, the systems and methods according to the present technology yield high quality diagnostic images that are comparable to state of the art devices and systems that may not be portable and/or compact.

In some embodiments, the O-shaped gantry 3930 of system 3900 may have a slip-ring design to transfer data and power without cables. Alternatively, O-shaped gantry 3930 may have cables (rather than slip ring) to transfer data and power. In some embodiments, data transfer may be accomplished wirelessly either instead of, or in addition to, the wired data connections. In an example of system 3900, a maximum rotation speed of the O-shaped gantry 3930 will be 2-3 seconds per rotation, to reduce G-forces and hence, reduce structural weight and complexity. By comparison, in at least some known O-shaped CT gantries, rotations speeds approach 0.2 seconds per rotation, requiring a heavy and precisely balanced gantry structure to handle high G forces. A lower O-shaped gantry 3930 rotation speed in the system 3900 according to the present technology also allows protecting structural integrity of the FPD 3920 and the 2D ASG 3410. Furthermore, the ability to tilt the O-shaped 3930 in the CT scanner system according to the present technology was hitherto challenging in at least some known portable and/or compact CT scanners to accommodate patient who are unable to lay flat or nearly horizontal.

In some embodiments configured for imaging the head and extremities, a radial distance between the x-ray source 3910 and the FPD 3920 may be from 60 cm to 100 cm. X-ray source 3910 to isocenter distance (SIsoD) in system 3900 may be from 30 to 60 cm. The human brain is about 15-16 cm in length in the craniocaudal direction. To scan the whole brain in one rotation of O-shaped gantry 3910, a width of 25 to 30 cm for FPD 3920 in the craniocaudal direction is needed. However, the use of such a large detector also requires a large 2D ASG 3410, which can increase system complexity. In some examples, use of a 20 cm wide FPD 3920 provides a sufficient width to scan the whole brain in a 9-12 cm wide FOV in the cranio-caudal direction, and with high quality imaging results without undue complexity issues for system 3900.

In some embodiments, two scans may be performed using system 3900 to increase the FOV, where the gantry is displaced about 10 cm in the cranio-caudal direction for the second scan, allowing a total coverage of 20 cm. To perform the second scan, gantry can be shifted electromechanically in the cranio-caudal direction, and multiple CT scans can be performed to increase craniocaudal coverage.

At least some known CBCT systems employ flat panel detectors with pulsed x-ray source and low frame acquisition rates, which can lead to long scan durations. To reduce scan duration, compact and/or portable embodiments of the CT scanner system 3900 according to the present technology may employ continuous x-ray exposure at high frame rates. To achieve high frame rates, pixel size may be increased to 0.4-0.6 mm, by binning pixels. With this approach, frame rates can be increased to 100 frame/second or more, allowing acquisition of 600-700 frames in 6-7 seconds to in one rotation of the O-shaped gantry 3930. For perfusion CT scans, even higher frame rates may be needed to complete a scan in 3 seconds or less. This can be achieved using the system 3900 according to the present technology by reducing the readout area of the FPD 3920 in the craniocaudal direction. The increase in frame rate will be proportional to the reduction in readout area.

In some embodiments, method 3902 may implement an image correction algorithm to correct residual scatter not stopped by the antiscatter grid for an image of the object 3940. Correction of the residual scatter intensity according to the present technology may be accomplished, at least in part, by measuring signal intensity variations in the FPD or detector pixel array to facilitate an improvement in the quality of the x-ray image. Referring now to FIG. 39G, method 3902 may include the step of receiving 3904, from the FPD 3920, data representative of an image of the object 3940 to facilitate an x-ray image of at least a portion of the object to be generated based on the data representative of the image of the object. In an example, method 3902 may also include the step of generating 3906 the x-ray image of at least a portion of the object 3940. Method 3902 may include the step of estimating 3908 a residual scatter intensity reaching the FPD 3920.

In some embodiments, method 3902 may include the step of correcting 3910 the residual scatter intensity to facilitate an improvement in a quality of the x-ray image of at least a portion of the object 3940. Correction of the residual scatter intensity according to the present technology may be accomplished, at least in part, by measuring signal intensity variations in the FPD or detector pixel array to facilitate an improvement in the quality of the x-ray image. In one example, the correcting 3910 step of method 3902 may include correcting 3912 the residual scatter intensity based on a pattern of signal intensity variations in projections of images of the object acquired by the detector pixel array.

In some embodiments, the estimating 3908 step of method 3902 may include determining 3914 a change in a ratio of an image intensity underneath a footprint of the 2D ASG 3410 to an image intensity in one or more of the open-ended channels of 2D ASG 3410 in the absence of the object 3940 positioned between the x-ray source 3910 and the FPD 3920. In some embodiments, the estimating 3908 step of method 3902 may include determining 3916 a change in the ratio of the image intensity underneath the footprint of the 2D ASG 3410 to the image intensity in one or more of the open-ended channels of 2D ASG 3410 in the presence of the object 3940 positioned between the x-ray source 3910 and the FPD 3920. Method 3902 may include either or both of the above-described determining step(s) 3914 and 3916.

In some embodiments, system 3900 may include one or more non-transitory computer readable media 3994 operably coupled to the controller or computer 3990. The medium or media may have method 3902-related program instructions stored thereon. The program instructions may be processor-readable and executable code (e.g., software or firmware). When executed by, for example and without limitation, one or more processors of the at least one controller or computer 3990, the program instructions may cause the at least one of the above-described processes, or steps, of method 3902 to be performed, at least in part, by the portable CT scanner system 3900, or similarly, system(s) 3600 and/or 3800.

Figure 39H:
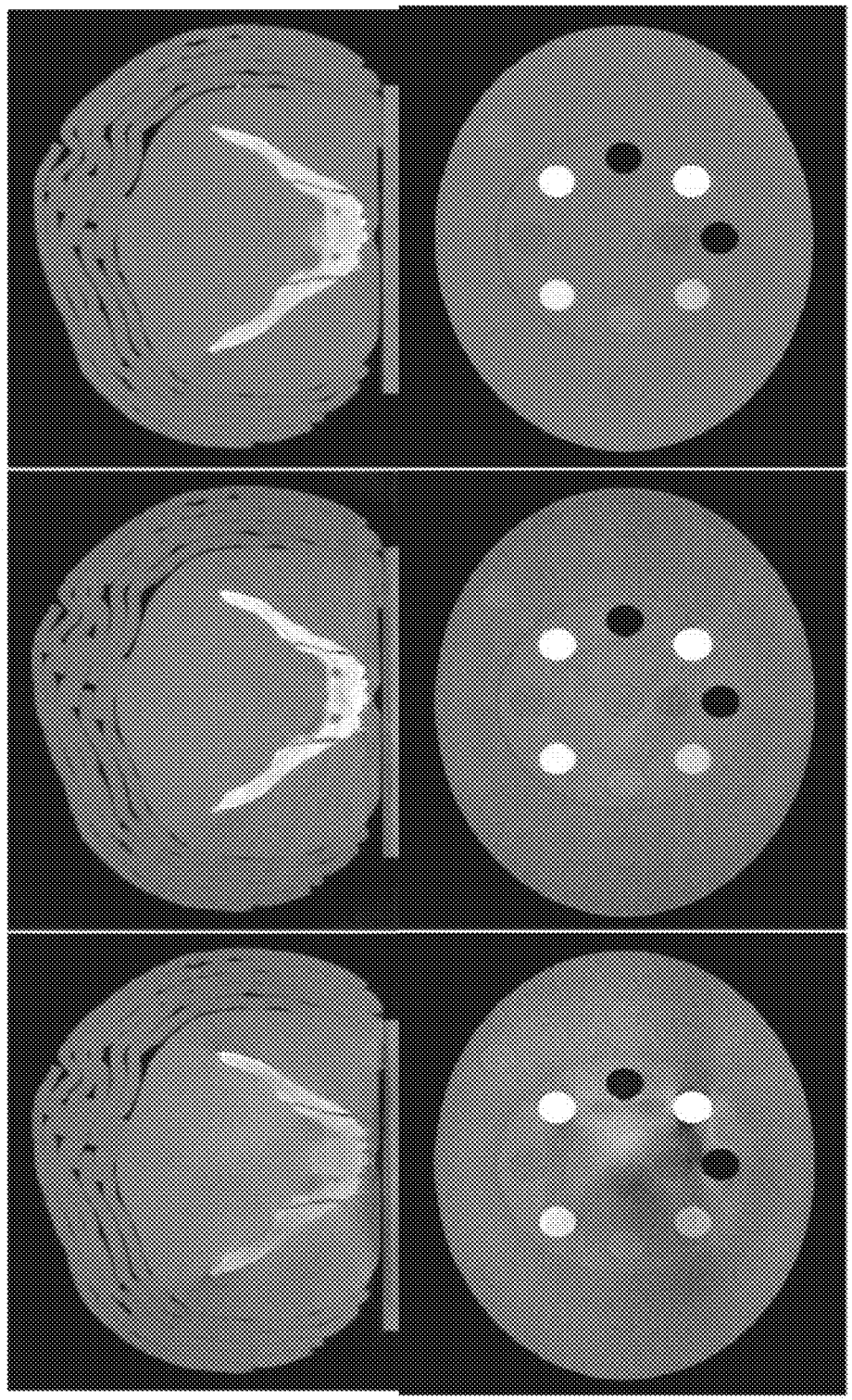
FIG. 39H presents CT scan images obtained using the system of FIGS. 39A-39F as compared to images obtained using known CT scanners.

FIG. 39H presents CT scan images obtained using the CT scanner system 3900 of FIGS. 39A-39F as compared to images obtained using known CT scanners. CT imaging experiments demonstrated an improvement in image quality of the portable and/or compact system 3900 according to the present technology as compared to known CT scanners that utilize FPD. FIG. 39H includes three pairs of images from: panel (1) a state of the art FDA approved CT with FPD on the left hand side, (2) the CT scanner system 3900 according to the present technology in the middle, and (3) a "gold standard" helical CT scanner—the Philips® Healthcare 16 slice CT scanner.

In the images of panel (1) of FIG. 39H, image artifacts are visible. Such image quality is unacceptable in the context of soft tissue imaging. In the images of panel (2) of FIG. 39H, shading artifacts are suppressed, and low contrast objects are clearly visible. No data correction methods were applied besides scatter correction to the panel (2) images. As can be seen by comparing the panel (2) images to the panel (3) images of FIG. 39H, the images generated using system 3900 according to the present technology are comparable in quality to the "gold standard" Philips® Healthcare 16 slice CT scanner.

Conventional CT detectors (and associated antiscatter grids) may require many CT gantry rotations to scan the anatomy of interest. Making many gantry rotations has many adverse effects. The gantry has to rotate very fast, and the gantry has to be built strong enough to withstand the g-forces. This approach not only increases the costs of the system, it also makes the system heavier. Requiring many gantry rotations may also requires a heavier duty x-ray tube and power generator to be able to generate x-rays during many gantry rotations. Furthermore, conventional CT detectors are custom designed for each system, which increase the costs.

In the x-ray imaging systems according to the present technology, use of a flat panel detector with a 2D antiscatter grid (and associated methods), to make the portable CT scanner lighter, more portable, and cheaper.

The use of antiscatter grids in a conventional CT scanner is a known approach. However, in the systems according to the present technology, a substantially different detector (i.e. flat panel detector) is used in the compact and/or portable CT scanner. The use of flat panel detector with 2D ASG brings substantially different challenges.

A known portable and conventional CT detector for brain imaging can image a 1 cm thick slice of brain per gantry rotation. Whereas the systems according to the present technology (e.g., CT scanner system 3900) uses an FPD and 2D ASG, along with methods for successful integration of the FPD and the 2D ASG, to image a 10+ cm thick slice of brain in one gantry rotation. Given that the brain is 15-16 cm long in the cranio-caudal direction, the known CT detector needs to complete 10+ gantry rotations to scan the whole brain. As a result, the known CT scanner requires: (a) fast rotating gantry (1-sec per rotation), which makes the gantry heavy and expensive; (b) a mechanism to move the scanner on the room floor, to scan the whole brain (without this mechanism, the known CT scanner can scan only 1 cm thick section of the brain; and (c) high power x-ray generator and x-ray tube to provide x-ray generation sufficient for 15-16 gantry rotations. Some known examples do not include the aforementioned mechanism to more the scanner on the room floor, however. The devices, systems and methods according to the present technology aim to address the aforementioned issues with the known CT scanner, as in the present technology (e.g., system 3900) does not require a fast-rotating gantry, it scan the whole brain with one or two gantry rotations, and therefore it does not need to move on the room floor, and it can operate using less x-ray power.

Another known x-ray imaging system is portable, uses a flat panel detector, and can image the whole head with one gantry rotary rotation. However, this known system does not use a 2D antiscatter grid to address the scatter problem, as described herein. This known system therefore does not provide sufficient image quality for visualizing brain, and it uses a C-shaped gantry which is not optimal for implementation of a 2D antiscatter grid due to, for example, gantry flex. When a C-shaped gantry rotates, its arms flex slightly due to gravity. Such a flexing in the arms, cause image artifacts when 2D antiscatter grid is in place. The present technology (e.g., system 3900) may use an O-shaped gantry, which reduces the gantry flex significantly and reduces image artifacts when 2D antiscatter grid is used. Moreover, the use of an O-shaped gantry (hence the reduced gantry flex) is better suited for the data correction methods according to the present technology (e.g., method 3902) needed for 2D antiscatter grid implementation. A C-shaped gantry rotates relatively slow (~8-20 secs per 360 degree rotation), whereas the O-shaped gantry 3930 of system 3900 may rotate as fast as 3 seconds per rotation. Operating a C-shaped gantry at higher rotation speeds may present safety concerns. If a C-shaped gantry hits the operator or the patient (e.g., due to unintentional movement of the patient), it can cause serious injury. These concerns are eliminated, or at least mitigated, using the O-shaped gantry 3930 in system 3900, for example.

Example 14

Figure 40A:
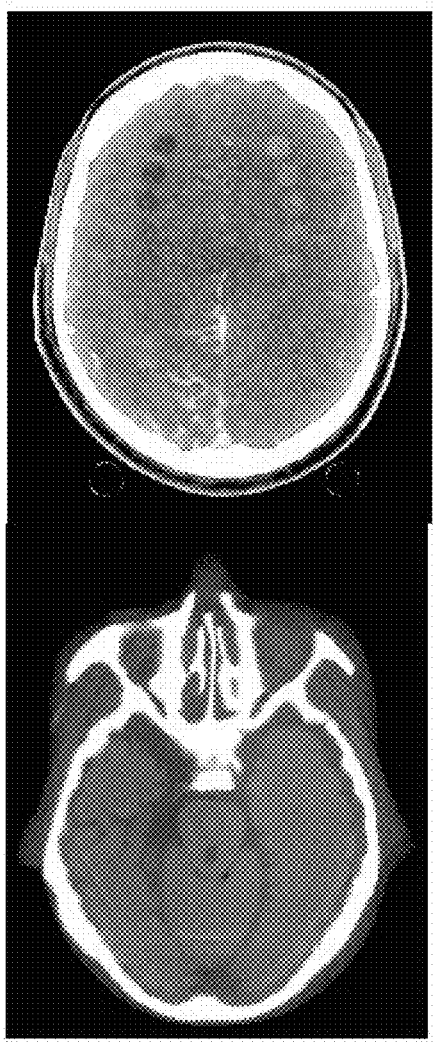
FIGS. 40A and 40B present images in comparison between an ultracompact CT (uCT) scanner with a 2D antiscatter grid according to some embodiments of the present technology (e.g., the system of FIGS. 39A-39F) and a helical CT scanner.
Figure 40B:
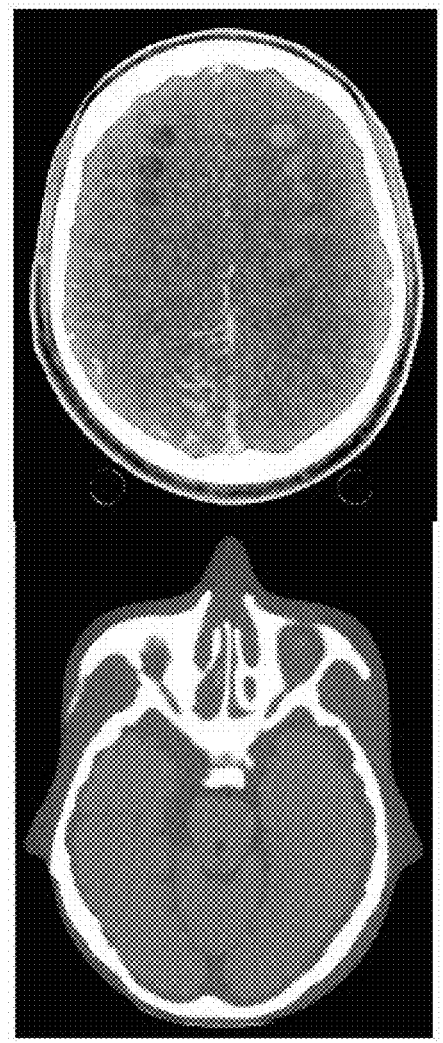

A commercially available CBCT scanner was modified to incorporate the 2D antiscatter grid hardware according to the present technology and was used to acquire images. FIGS. 40A and 40B present images in comparison between an ultracompact CT (uCT) scanner with a 2D antiscatter grid according to some embodiments of the present technology (e.g., system 3900 of FIGS. 39A-39F) and a helical CT scanner. The latter system is referred to in FIG. 40B as a "gold standard." The images in FIG. 40A were acquired using the uCT scanner with the 2D antiscatter grid according to the present technology (e.g., 2D ASG 3410), and the images in FIG. 40B were acquired by using the gold standard helical CT scanner. Comparing the pair of images of two different slices of a human head in FIG. 40A to the pair of images of the same physiological features in FIG. 40B, it can be seen that the uCT scanner using the 2D antiscatter grid demonstrates noninferiority of the present technology with respect to the gold standard approach.

Example 15

FIGS. 41A and 41B present a comparison of images obtained using a CBCT system and processed without and with, respectively, the techniques of the method 3902 shown in FIG. 39G. As can be seen in the pair of images in FIG. 41A, sever shading artifacts are apparent. Such artifacts are an indication of poor scatter suppression and poor image quality. Moving now to the pair of images in FIG. 41B, application of the correction algorithm by method 3902 according to the present technology results in substantially fewer artifacts, which indicates a higher image quality.

Example 16

FIGS. 42A and 42B present a comparison of images obtained using the gold standard CT and a CBCT scanner (e.g., system 3900), respectively, according to the present technology. The pair of images shown in FIG. 42B, acquired with the 2D antiscatter grid according to the present technology (e.g., 2D ASG 3410) are expected to be similar to the pair of images of FIG. 42A using the gold standard system.

Qualitatively, these images indicate that the approach according to the present technology (e.g., system 3900) provides comparable image quality when compared to gold standard CT scans.

Example 17

Figures 43A, 43B, 43C:
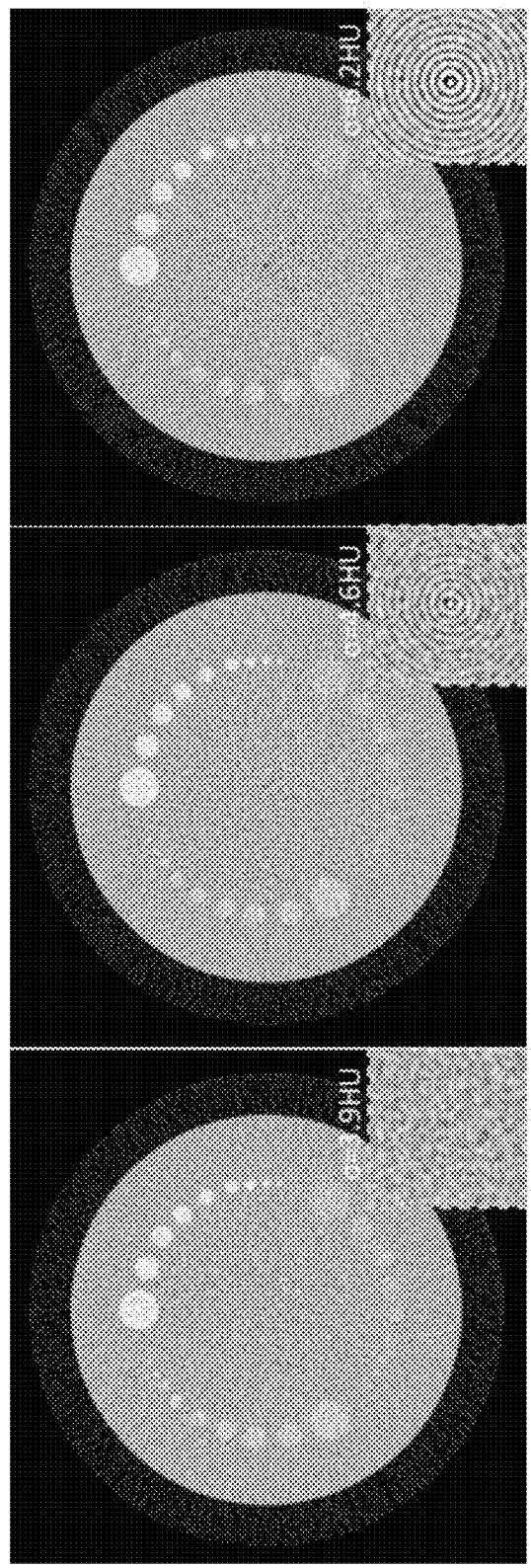
FIGS. 43A, 43B and 43C present simulated images in comparison to demonstrate the effect of CT gantry shape on gantry flex and 2D antiscatter grid performance.

FIGS. 43A, 43B and 43C present simulated images in comparison to demonstrate the effect of CT gantry shape on gantry flex and 2D antiscatter grid performance. The insets in each of FIGS. 43A-43C are the zoomed-in central portion of each CT image. The simulated CT image of FIG. 43A was produced using an O-shaped gantry (e.g., 3930) with associated 2D ASG (e.g., 3410). The simulated CT image of FIGS. 43B and 43C were produced using a C-shaped gantry (3930) with associated 2D ASG (e.g., 3410).

The image of FIG. 43A demonstrates image quality when there is no gantry flex as in an O-shaped gantry. The simulated CT images of FIGS. 43B and 43C with small, and medium, amounts of gantry flex, respectively, in the C-shaped gantry. An O-shaped gantry (e.g., 3930) minimizes the gantry flex when the gantry is rotating around the patient. As a result, a 2D antiscatter grid's (e.g., 2D ASG 3410) shadows can be corrected using a conventional flat field correction technique, and ring artifacts in CT images are avoided. Whereas in a C-shaped gantry, the grid shadows are not properly suppressed, causing ring artifacts in CT images. Depending on the magnitude of gantry flex, the intensity of ring artifacts will also vary. Notably, x-ray imaging systems that do not utilize 2D ASDs may experience less of an issue arising from gantry flex. Accordingly, the technically advantageous features of the systems and methods (e.g., system 3900 and method 3902) according to the present technology can prevent, or at least mitigate, the aforementioned negative effects of gantry flex that were hitherto extant in at least some known x-ray imaging systems.

Figure 44:
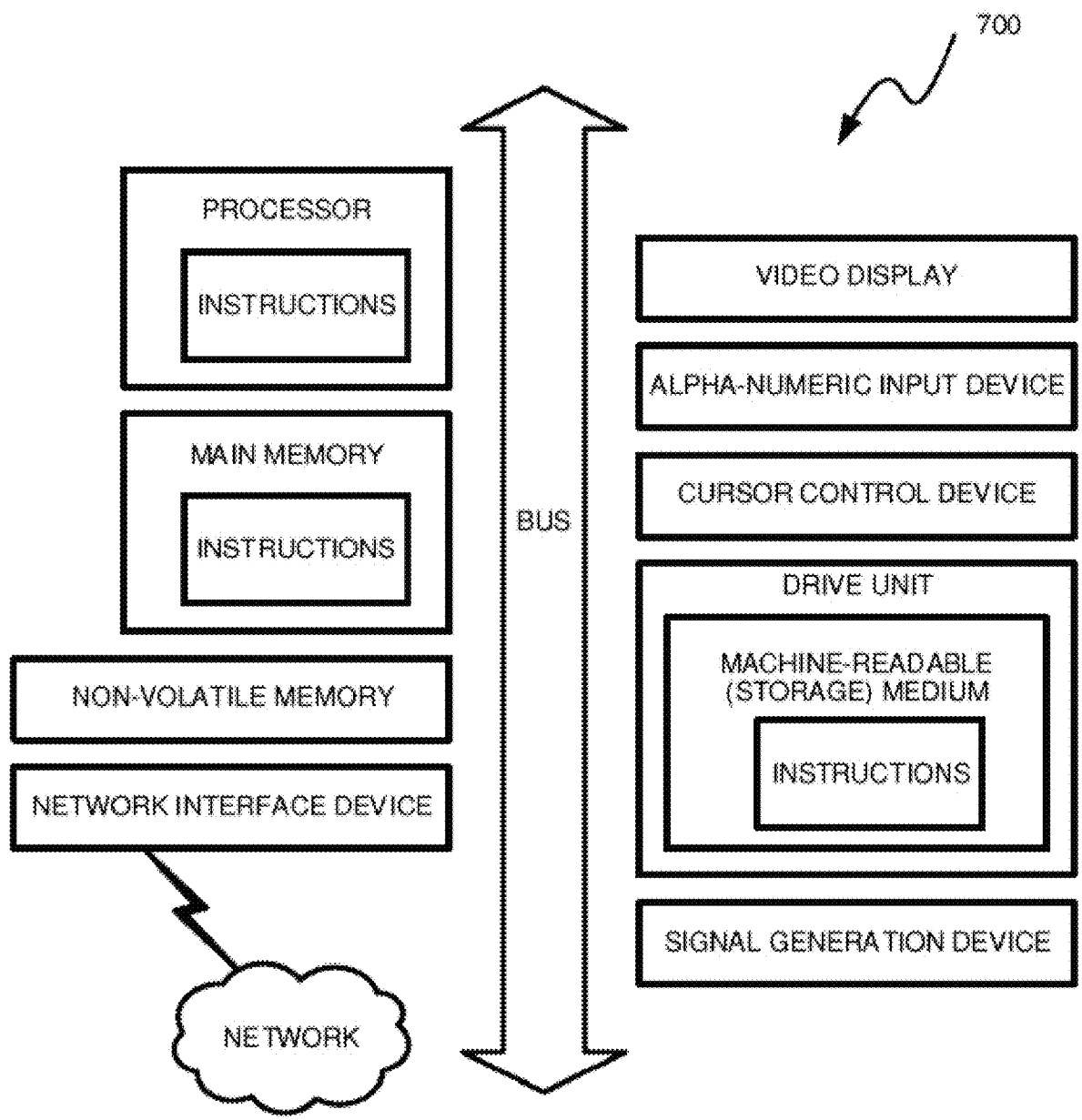
FIG. 44 presents a diagrammatic representation of a machine, in the example form, of a computer system within which a set of instructions, for causing the machine to implement or otherwise perform any one or more of the techniques and methodologies of the present technology described herein, may be executed.

FIG. 44 presents a diagrammatic representation of a machine, in the example form, of a computer system 700 within which a set of instructions, for causing the machine to implement or otherwise perform any one or more of the techniques and methodologies of the present technology described herein, may be executed. In the example of FIG. 44, the computer system 700 includes a processor, memory, non-volatile memory, and an interface device. Various common components (e.g., cache memory) are omitted for illustrative simplicity. The computer system 700 is intended to illustrate a hardware device on which any of the components depicted in the foregoing examples and embodiments of the present technology can be implemented. For example, the computer system 700 can be, or may include, an image processing system or a motor control system. The computer system 700 can be of any applicable known or convenient type. The components of the computer system 700 can be coupled together via a bus or through some other known or convenient device.

The processor of computer system 700 may be, for example, a conventional microprocessor such as an INTEL PENTIUM microprocessor or MOTOROLA POWER PC microprocessor. One of skill in the relevant art will recognize that the terms "machine-readable (storage) medium" or "computer-readable (storage) medium" include any type of device that is accessible by the processor. In some embodiment, these storage media are embodied in non-transitory computer-readable media that can store program instructions (e.g., as software or firmware) which, when executed by one or more processors of the disclosed technology, cause the processor(s) or other controller means to implement, execute, or otherwise facilitate performance of the various algorithms and methods disclosed herein.

In computer system 700, the memory is coupled to the processor by, for example, a bus. The memory can include, by way of example but not limitation, random access memory (RAM), such as dynamic RAM (DRAM) and static RAM (SRAM). The memory can be local, remote, or distributed.

The bus of computer system 700 also couples the processor to the non-volatile memory and drive unit. The non-volatile memory is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. Some of this data is often written, by a direct memory access process, into memory during execution of software in the computer system 700. The non-volatile storage can be local, remote, or distributed. The non-volatile memory is optional because systems can be created with all applicable data available in memory. An embodiment of computer system 700 will usually include at least a processor, memory, and a device (e.g., a bus) coupling the memory to the processor.

Software or firmware utilized by computer system 700 may be stored in the non-volatile memory and/or the drive unit. Indeed, for large programs, it may not even be possible to store the entire program in the memory. Nevertheless, it should be understood that for software and/or firmware to run, if necessary, it is moved to a computer readable location appropriate for processing, and for illustrative purposes, that location is referred to as the memory in this paper. Even when software is moved to the memory for execution, the processor will typically make use of hardware registers to store values associated with the software, and local cache that, ideally, serves to speed up execution. As used herein, firmware or a software program is assumed to be stored at any known or convenient location (from non-volatile storage to hardware registers) when the software program is referred to as "implemented in a computer-readable medium". A processor is considered to be "configured to execute a program" when at least one value associated with the program is stored in a register readable by the processor.

The bus also couples the processor to the network interface device of computer system 700. The interface can include one or more of a modem or network interface. It will be appreciated that a modem or network interface can be considered to be part of the computer system. The interface can include an analog modem, ISDN modem, cable modem, token ring interface, satellite transmission interface (e.g., "direct PC"), or other interfaces for coupling a computer system (e.g., 700) to other computer systems. The interface can include one or more input and/or output (I/O) devices. The I/O devices can include, by way of example but not limitation, a keyboard, a mouse or other pointing device, disk drives, printers, a scanner, and other input and/or output devices, including a display device. The display device can include, by way of example but not limitation, a cathode ray tube (CRT), liquid crystal display (LCD), or some other applicable known or convenient display device. For simplicity, it is assumed that controllers of any devices not depicted in the example of FIG. 44 reside in the interface.

In operation, the computer system 700 can be controlled by operating system software that includes a file management system, such as a disk operating system. One example of operating system software with associated file management system software is the family of operating systems known as WINDOWS from MICROSOFT Corporation of Redmond, Washington, and their associated file management systems. Another example of operating system software with its associated file management system software is the LINUX operating system and its associated file management system. The file management system is typically stored in the non-volatile memory and/or drive unit and causes the processor to execute the various acts required by the operating system to input and output data and to store data in the memory, including storing files on the non-volatile memory and/or drive unit.

Some portions of the detailed description may be presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The algorithms and displays presented herein are not inherently related to any particular computer or other apparatus. Various general-purpose systems may be used with programs in accordance with the teachings herein, or it may prove convenient to construct more specialized apparatus to perform the methods of some embodiments. The required structure for a variety of these systems will appear from the description below. In addition, the techniques are not described with reference to any particular programming language, and various embodiments may thus be implemented using a variety of programming languages.

In alternative embodiments, the machine operates as a standalone device or may be connected (e.g., networked) to other machines. In a networked deployment, the machine may operate in the capacity of a server or a client machine in a client-server network environment or as a peer machine in a peer-to-peer (or distributed) network environment.

The machine may be a server computer, a client computer, a personal computer (PC), a tablet PC, a laptop computer, a set-top box (STB), a personal digital assistant (PDA), a cellular telephone, an IPHONE, a BLACKBERRY, a processor, a telephone, a web appliance, a network router, switch or bridge, or any machine capable of executing a set of instructions (sequential or otherwise) that specify actions to be taken by that machine.

While the machine-readable medium or machine-readable storage medium is shown in an exemplary embodiment to be a single medium, the term "machine-readable medium" and "machine-readable storage medium" should be taken to include a single medium or multiple media (e.g., a centralized or distributed database, and/or associated caches and servers) that store the one or more sets of instructions. The term "machine-readable medium" and "machine-readable storage medium" shall also be taken to include any medium that is capable of storing, encoding or carrying a set of instructions for execution by the machine and that cause the machine to perform any one or more of the methodologies of the presently disclosed technique and innovation.

In general, the routines executed to implement the embodiments of the disclosure, may be implemented as part of an operating system or a specific application, component, program, object, module or sequence of instructions referred to as "computer programs." The computer programs typically comprise one or more instructions set at various times in various memory and storage devices in a computer, and that, when read and executed by one or more processing units or processors in a computer, cause the computer to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include but are not limited to recordable type media such as volatile and non-volatile memory devices, floppy and other removable disks, hard disk drives, optical disks (e.g., Compact Disk Read-Only Memory (CD ROMS), Digital Versatile Disks, (DVDs), etc.), among others, and transmission type media such as digital and analog communication links.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above detailed description using the singular or plural number may also include the plural or singular number, respectively. The word "or," in reference to a list of two or more items, covers all of the following interpretations of the word: any of the items in the list, all of the items in the list, and any combination of the items in the list.

The above detailed description of embodiments of the disclosure is not intended to be exhaustive or to limit the teachings to the precise form disclosed above. While specific embodiments of, and examples for, the disclosure are described above for illustrative purposes, various equivalent modifications are possible within the scope of the disclosure, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are, at times, shown as being performed in a series, these processes or blocks may instead be performed in parallel, or may be performed at different times. Further, any specific numbers noted herein are only examples: alternative implementations may employ differing values or ranges.

The teachings of the disclosure provided herein can be applied to other systems, not necessarily the system described above. Likewise, the elements and acts of the various embodiments described above can be combined to provide further embodiments.

These and other changes can be made to the disclosure in light of the above detailed description. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific embodiments disclosed in the specification, unless the above detailed description section explicitly defines such terms. Accordingly, the actual scope of the disclosure encompasses not only the disclosed embodiments, but also all equivalent ways of practicing or implementing the disclosure under the claims.

Any patents or patent applications and other references noted above, including any that may be listed in accompanying filing papers, are incorporated herein by reference in their entireties. Aspects of the disclosure can be modified, if necessary, to employ the systems, functions, and concepts of the various references described above to provide yet further embodiments of the disclosure.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112(f), other aspects may likewise be embodied as a means-plus-function claim, or in other forms, such as being embodied in a computer-readable medium. (Any claims intended to be treated under 35 U.S.C. § 112(f) will begin with the words "means for".) Accordingly, the applicant reserves the right to add additional claims after filing the application to pursue such additional claim forms for other aspects of the disclosure.

The detailed description provided herein may be applied to other devices, systems and methods, not necessarily only the devices, systems and methods described above. The elements and acts of the various examples and embodiments described above can be combined to provide further implementations of the invention. Some alternative implementations of the invention may include not only additional elements to those implementations noted above, but also may include fewer elements. These and other changes can be made to the invention in light of the above detailed description. While the above description defines certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above detailed description section explicitly defines such terms. Accordingly, the actual scope of the invention encompasses not only the disclosed examples, but also all equivalent ways of practicing or implementing the invention.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Moreover, although specific embodiments have been illustrated and described herein, it should be appreciated that any subsequent arrangement designed to achieve the same or similar purpose may be substituted for the specific embodiments shown.

This disclosure is intended to cover any and all subsequent adaptations or variations of various embodiments. Combinations of the above embodiments can be made, and other embodiments not specifically described herein will be apparent to those of skill in the art upon reviewing the description. Additionally, the illustrations are merely representational and may not be drawn to scale. Certain proportions within the illustrations may be exaggerated, while other proportions may be reduced. Accordingly, the disclosure and the figures are to be regarded as illustrative and not restrictive.

REFERENCES

1. Altunbas, C. et al. (2014) "Su-D-12a-04: Investigation of a 2D Antiscatter Grid for Flat Panel Detectors," *Med. Phys.* 41(6), 124-124.
2. Fetterly, K. A. and Schueler, B. A. (2007) "Experimental Evaluation of Fiber-Interspaced Antiscatter Grids for Large Patient Imaging with Digital X-Ray Systems," *Phys. Med. Biol.* 52(16), 4863-4880.
3. Fetterly, K. A. and Schueler, B. A. (2009) "Physical Evaluation of Prototype High-Performance Anti-Scatter Grids: Potential for Improved Digital Radiographic Image Quality," *Phys. Med. Biol.* 54(2), N37-42.
4. Siewerdsen, J. H. and Jaffray, D. A. (2001) "Cone-Beam Computed Tomography with a Flat-Panel Imager: Magnitude and Effects of X-Ray Scatter," *Med. Phys.* 28(2), 220-231.
5. Ruhrnschopf, E.-P. and Klingenbeck, K. (2011) "A General Framework and Review of Scatter Correction Methods in X-Ray Cone-Beam Computerized Tomography. Part 1: Scatter Compensation Approaches," *Med. Phys.* 38(7), 4296-4311.
6. Angle, J. F. (2013) "Cone-Beam Ct: Vascular Applications," *Tech. Vasc. Interv. Radiol.* 16(3), 144-149.
7. De Vos, W. et al. (2009) "Cone-Beam Computerized Tomography (Cbct) Imaging of the Oral and Maxillofacial Region: A Systematic Review of the Literature," *Int. J. Oral Maxillofac. Surg.* 38(6), 609-625.
8. Van de Kelft, E. et al. (2012) "A Prospective Multicenter Registry on the Accuracy of Pedicle Screw Placement in the Thoracic, Lumbar, and Sacral Levels with the Use of the O-Arm Imaging System and Stealthstation Navigation," *Spine* 37(25), E1580-E1587.
9. Simpson, D. R. et al. (2010) "A Survey of Image-Guided Radiation Therapy Use in the United States," *Cancer* 116(16), 3953-3960.
10. Jaffray, D. A. (2012) "Image-Guided Radiotherapy: From Current Concept to Future Perspectives," *Nature Reviews Clinical Oncology* 9(12), 688-699.
11. Yang, H. et al. (2013) "Replanning During Intensity Modulated Radiation Therapy Improved Quality of Life in Patients with Nasopharyngeal Carcinoma," *International Journal of Radiation Oncology\* Biology\* Physics* 85(1), e47-e54.
12. Castadot, P. et al. (2010) "Adaptive Radiotherapy of Head and Neck Cancer," *Semin. Radiat. Oncol.* 20(2), 84-93.
13. Schwartz, D. L. et al. (2013) "Adaptive Radiotherapy for Head and Neck Cancer—Dosimetric Results from a Prospective Clinical Trial," *Radiother. Oncol.* 106(1), 80-84.
14. Castadot, P. et al. (2011) "Adaptive Functional Image-Guided Imrt in Pharyngo-Laryngeal Squamous Cell Carcinoma: Is the Gain in Dose Distribution Worth the Effort?," *Radiother. Oncol.* 101(3), 343-350.
15. Hansen, E. K. et al. (2006) "Repeat Ct Imaging and Replanning During the Course of Imrt for Head-and-Neck Cancer," *International Journal of Radiation Oncology\* Biology\* Physics* 64(2), 355-362.
16. Barker, J. L. et al. (2004) "Quantification of Volumetric and Geometric Changes Occurring During Fractionated Radiotherapy for Head-and-Neck Cancer Using an Integrated Ct/Linear Accelerator System," *International Journal of Radiation Oncology\* Biology\* Physics* 59(4), 960-970.
17. Foroudi, F. et al. (2011) "Online Adaptive Radiotherapy for Muscle-Invasive Bladder Cancer: Results of a Pilot Study," *International Journal of Radiation Oncology\* Biology\* Physics* 81(3), 765-771.
18. Tyagi, N. et al. (2011) "Daily Online Cone Beam Computed Tomography to Assess Interfractional Motion in Patients with Intact Cervical Cancer," *International Journal of Radiation Oncology\* Biology\* Physics* 80(1), 273-280.
19. Bertelsen, A. et al. (2011) "Radiation Dose Response of Normal Lung Assessed by Cone Beam Ct—a Potential Tool for Biologically Adaptive Radiation Therapy," *Radiother. Oncol.* 100(3), 351-355.
20. Kwint, M. et al. (2014) "Intra Thoracic Anatomical Changes in Lung Cancer Patients During the Course of Radiotherapy," *Radiother. Oncol.* 113(3), 392-397.
21. Weiss, E. et al. (2010) "Clinical Evaluation of Soft Tissue Organ Boundary Visualization on Cone-Beam Computed Tomographic Imaging," *IJROBP* 78(3), 929-936.

22. Lütgendorf-Caucig, C. et al. (2011) "Feasibility of Cbct-Based Target and Normal Structure Delineation in Prostate Cancer Radiotherapy: Multi-Observer and Image Multi-Modality Study," *Radiother. Oncol.* 98(2), 154-161.
23. Hou, J. et al. (2011) "Deformable Planning Ct to Cone-Beam Ct Image Registration in Head-and-Neck Cancer," *Med. Phys.* 38(4), 2088-2094.
24. Veiga, C. et al. (2014) "Toward Adaptive Radiotherapy for Head and Neck Patients:
Feasibility Study on Using Ct-to-Cbct Deformable Registration for "Dose of the Day" Calculations," *Med. Phys.* 41(3), 031703.
25. Møller, D. S. et al. (2014) "Adaptive Radiotherapy of Lung Cancer Patients with Pleural Effusion or Atelectasis," *Radiother. Oncol.* 110(3), 517-522.
26. Chen, A. M. et al. (2014) "Clinical Outcomes among Patients with Head and Neck Cancer Treated by Intensity—Modulated Radiotherapy with and without Adaptive Replanning," *Head Neck* 36(11), 1541-1546.
27. Kyriakou, Y. and Kalender, W. (2007) "Efficiency of Antiscatter Grids for Flat-Detector Ct," *Phys. Med. Biol.* 52(20), 6275-6293.
28. Lazos, D. and Williamson, J. F. (2010) "Monte Carlo Evaluation of Scatter Mitigation Strategies in Cone-Beam Ct," *Med. Phys.* 37(10), 5456-5470.
29. Altunbas, C. (2014) "Image Corrections for Scattered Radiation," in *Cone Beam Computed Tomography* (Shaw, C. C., Ed.), pp 129-147, CRC Press, Boca Raton, FL.
30. Ding, G. X. et al. (2007) "A Study on Adaptive Imrt Treatment Planning Using Kv Cone-Beam Ct," *Radiother. Oncol.* 85(1), 116-125.
31. Guan, H. and Dong, H. (2009) "Dose Calculation Accuracy Using Cone-Beam Ct (Cbct) for Pelvic Adaptive Radiotherapy," *Phys. Med. Biol.* 54(20), 6239.
32. Fotina, I. et al. (2012) "Feasibility of Cbct-Based Dose Calculation: Comparative Analysis of Hu Adjustment Techniques," *Radiother. Oncol.* 104(2), 249-256.
33. Niu, T. et al. (2012) "Quantitative Cone-Beam Ct Imaging in Radiation Therapy Using Planning Ct as a Prior: First Patient Studies," *Med. Phys.* 39(4), 1991-2000.
34. Yang, Y. et al. (2007) "Evaluation of on-Board Kv Cone Beam Ct (Cbct)-Based Dose Calculation," *Phys. Med. Biol.* 52(3), 685.
35. Ruhrnschopf, E. P. and Klingenbeck, K. (2011) "A General Framework and Review of Scatter Correction Methods in X-Ray Cone-Beam Computerized Tomography. Part 1: Scatter Compensation Approaches," *Med. Phys.* 38(7), 4296-4311.
36. Ruhrnschopf, E.-P. and Klingenbeck, a. K. (2011) "A General Framework and Review of Scatter Correction Methods in Cone Beam Ct. Part 2: Scatter Estimation Approaches," *Med. Phys.* 38(9), 5186-5199.
37. Altunbas, M. C. et al. (2007) "A Post-Reconstruction Method to Correct Cupping Artifacts in Cone Beam Breast Computed Tomography," *Med. Phys.* 34(7), 3109-3118.
38. Liu, X. et al. (2006) "An Accurate Scatter Measurement and Correction Technique for Cone Beam Breast Ct Imaging Using Scanning Sampled Measurement (Ssm) Technique," *Proc. SPIE-Int. Soc. Opt. Eng.* 6142, 614234.
39. Siewerdsen, J. H. et al. (2004) "The Influence of Antiscatter Grids on Soft-Tissue Detectability in Cone-Beam Computed Tomography with Flat-Panel Detectors," *Med. Phys.* 31(12), 3506-3520.
40. Schafer, S. et al. (2012) "Antiscatter Grids in Mobile C-Arm Cone-Beam Ct: Effect on Image Quality and Dose," *Med. Phys.* 39(1), 153-159.
41. Sisniega, A. et al. (2013) "Monte Carlo Study of the Effects of System Geometry and Antiscatter Grids on Cone-Beam Ct Scatter Distributions," *Med. Phys.* 40(5), -.
42. Wiegert, J. et al. (2004) "Performance of Standard Fluoroscopy Antiscatter Grids in Flat-Detector-Based Cone-Beam Ct," *Proc. SPIE-Int. Soc. Opt. Eng.* 5368, 67-78.
43. Lazos, D. et al. (2007) "Evaluation of Scatter Mitigation Strategies for X-Ray Cone-Beam Ct: Impact of Scatter Subtraction and Anti-Scatter Grids on Contrast-to-Noise Ratio," (Jiang, H. and Michael, J. F., Eds.), p 65101V, SPIE.
44. Neitzel, U. (1992) "Grids or Air Gaps for Scatter Reduction in Digital Radiography: A Model Calculation," *Med. Phys.* 19(2), 475-481.
45. Bonenkamp, J. G. and Boldingh, W. H. (1959) "Quality and Choice of Potter Bucky Grids," *Acta Radiologica* [*Old Series*] 52(3), 241-253.
46. Santos, E. C. et al. (2006) "Rapid Manufacturing of Metal Components by Laser Forming," *International Journal of Machine Tools and Manufacture* 46(12-13), 1459-1468.
47. Gray, J. and Princehorn, J. "Htc Grids Improve Mammography Contrast (White Paper)," (Inc., H., Ed.).
48. Vogtmeier, G. et al. (2008) "Two-Dimensional Anti-Scatter Grids for Computed Tomography Detectors," (Jiang, H. and Ehsan, S., Eds.), p 691359, SPIE.
49. Kawrakow, I. and Rogers, D. (2000) "The Egsnrc Code System: Monte Carlo Simulation of Electron and Photon Transport."
50. Yi, Y. et al. (2011) "Radiation Doses in Cone-Beam Breast Computed Tomography: A Monte Carlo Simulation Study," *Med. Phys.* 38(2), 589-597.
51. Varian. (2010) "The Truebeam Technical Reference Guide-Volume 2: Imaging," Varian Medical Systems, Inc, Palo Alto, CA
52. Johns, P. C. and Yaffe, M. (1982) "Scattered Radiation in Fan Beam Imaging Systems," *Med. Phys.* 9(2), 231-239.
53. Abella, M. et al. (2012) "Software Architecture for Multi-Bed Fdk-Based Reconstruction in X-Ray Ct Scanners," *Comput. Methods Programs Biomed.* 107(2), 218-232.
54. Hsieh, J. (2009) in *Computed Tomography: Principles, Design, Artifacts, and Recent Advances*, SPIE Press, Bellingham, Washington
55. Starman, J. et al. (2011) "Investigation into the Optimal Linear Time-Invariant Lag Correction for Radar Artifact Removal," *Med. Phys.* 38(5), 2398-2411.
56. Altunbas, C. et al. (2014) "Reduction of Ring Artifacts in Cbct: Detection and Correction of Pixel Gain Variations in Flat Panel Detectors," *Med. Phys.* 41(9), 091913.
57. Sharpe, M. B. et al. (2006) "The Stability of Mechanical Calibration for a Kv Cone Beam Computed Tomography System Integrated with Linear Acceleratora)," *Med. Phys.* 33(1), 136-144.
58. Bissonnette, J. P. et al. (2008) "Quality Assurance for the Geometric Accuracy of Cone-Beam Ct Guidance in Radiation Therapy," *Int. J. Radiat. Oncol. Biol. Phys.* 71(1 Suppl), S57-61.
59. Gao, S. et al. (2014) "Evaluation of Isocal Geometric Calibration System for Varian Linacs Equipped with on-Board Imager and Electronic Portal Imaging Device Imaging Systems," *J. Appl. Clin. Med. Phys.* 15(3), 4688.
60. Zheng, D. et al. (2011) "Bow-Tie Wobble Artifact: Effect of Source Assembly Motion on Cone-Beam Ct," *Med. Phys.* 38(5), 2508-2514.
61. Jaffray, D. A. et al. (2002) "Flat-Panel Cone-Beam Computed Tomography for Image-Guided Radiation Therapy," *International Journal of Radiation Oncology, Biology, Physics* 53(5), 1337-1349.
62. Stankovic, U. et al. (2014) "Improved Image Quality of Cone Beam Ct Scans for Radiotherapy Image Guidance Using Fiber-Interspaced Antiscatter Grid," *Med. Phys.* 41(6).
63. Sijbers, J. and Andrei, P. (2004) "Reduction of Ring Artefacts in High Resolution Micro-Ct Reconstructions," *Phys. Med. Biol.* 49(14), N247.
64. Star-Lack, J. et al. (2006) "Su-Ff-I-04: A Fast Variable-Intensity Ring Suppression Algorithm," *Med. Phys.* 33(6), 1997.
65. Hatton, J. et al. (2009) "Cone Beam Computerized Tomography: The Effect of Calibration of the Hounsfield Unit Number to Electron Density on Dose Calculation Accuracy for Adaptive Radiation Therapy," *Phys. Med. Biol.* 54(15), N329.
66. Altunbas, C. et al. (2013) "Dosimetric Errors During Treatment of Centrally Located Lung Tumors with Stereotactic Body Radiation Therapy: Monte Carlo Evaluation of Tissue Inhomogeneity Corrections," *Med. Dosim.* 38(4), 436-441.
67. Miften, M. et al. (2001) "Comparison of Rtp Dose Distributions in Heterogeneous Phantoms with the Beam Monte Carlo Simulation System," *J. Appl. Clin. Med. Phys.* 2(1), 21-31.
68. Gayou, O. et al. (2007) "Patient Dose and Image Quality from Mega-Voltage Cone Beam Computed Tomography Imaging," *Med. Phys.* 34(2), 499-506.
69. Fogliata, A. et al. (2007) "On the Dosimetric Behaviour of Photon Dose Calculation Algorithms in the Presence of Simple Geometric Heterogeneities: Comparison with Monte Carlo Calculations," *Phys. Med. Biol.* 52(5), 1363.
70. Knöös, T. et al. (2006) "Comparison of Dose Calculation Algorithms for Treatment Planning in External Photon Beam Therapy for Clinical Situations," *Phys. Med. Biol.* 51(22), 5785.
71. Altunbas, C. et al. (2016) "We-Ab-207a-10: Transmission Characteristics of a Two Dimensional Antiscatter Grid Prototype for Cbct," *Med. Phys.* 43(6), 3799-3800.
72. Kwan, A. L. C. et al. (2005) "Evaluation of X-Ray Scatter Properties in a Dedicated Cone-Beam Breast Ct Scanner," *Med. Phys.* 32(9), 2967-2975.
73. Graham, S. A. et al. (2007) "Compensators for Dose and Scatter Management in Cone-Beam Computed Tomography," *Med. Phys.* 34(7), 2691-2703.
74. Mail, N. et al. (2009) "The Influence of Bowtie Filtration on Cone-Beam Ct Image Quality," *Med. Phys.* 36(1), 22-32.
75. Menser, B. et al. (2010) "Use of Beam Shapers for Cone-Beam Ct with Off-Centered Flat Detector," pp 762233-762233-762212.
76. Ning, R. et al. (2002) "X-Ray Scatter Suppression Algorithm for Cone-Beam Volume Ct," pp 774-781.
77. Sun, M. et al. (2011) "Correction for Patient Table-Induced Scattered Radiation in Cone-Beam Computed Tomography (Cbct)," *Med. Phys.* 38(4), 2058-2073.
78. Zhu, L. et al. (2006) "Scatter Correction Method for X-Ray Ct Using Primary Modulation: Theory and Preliminary Results," *IEEE Trans. Med. Imaging* 25(12), 1573-1587.
79. Zbijewski, W. and Beekman, F. J. (2006) "Efficient Monte Carlo Based Scatter Artifact Reduction in Cone-Beam Micro-Ct," *IEEE Trans. Med. Imaging* 25(7), 817-827.
80. Siewerdsen, J. H. et al. (2006) "A Simple, Direct Method for X-Ray Scatter Estimation and Correction in Digital Radiography and Cone-Beam Ct," *Med. Phys.* 33(1), 187-197.
81. Bertram, M. et al. (2006) "Scatter Correction for Cone-Beam Computed Tomography Using Simulated Object Models," pp 61421C-61421C-61412.
82. Wiegert, J. et al. (2008) "Iterative Scatter Correction Based on Artifact Assessment," pp 69132B-69132B-69112.
83. Poludniowski, G. et al. (2009) "An Efficient Monte Carlo-Based Algorithm for Scatter Correction in Key Cone-Beam Ct," *Phys. Med. Biol.* 54(12), 3847-3864.
84. Sechopoulos, I. (2012) "X-Ray Scatter Correction Method for Dedicated Breast Computed Tomography," *Med. Phys.* 39(5), 2896-2903.
85. Landry, G. et al. (2015) "Investigating Ct to Cbct Image Registration for Head and Neck Proton Therapy as a Tool for Daily Dose Recalculation," *Med. Phys.* 42(3), 1354-1366.
86. Makarova, O. V. et al. (2002) "Focused Two-Dimensional Antiscatter Grid for Mammography," pp 148-155.
87. Patel, T. et al. (2016) "Effects on Image Quality of a 2D Antiscatter Grid in X-Ray Digital Breast Tomosynthesis: Initial Experience Using the Dual Modality (X-Ray and Molecular) Breast Tomosynthesis Scanner," *Med. Phys.* 43(4), 1720.
88. Vogtmeier, G. et al. (2008) "Two-Dimensional Anti-Scatter Grids for Computed Tomography Detectors," *Proc. SPIE-Int. Soc. Opt. Eng.* 6913, 691359-691359-691311.
89. Draper, N. R. and Smith, H. (2014) *Applied Regression Analysis*, Third Edition ed., John Wiley & Sons.
90. Lazos, D. and Williamson, J. F. (2012) "Impact of Flat Panel-Imager Veiling Glare on Scatter-Estimation Accuracy and Image Quality of a Commercial on-Board Cone-Beam Ct Imaging System," *Med. Phys.* 39(9), 5639-5651.
91. Chan, H. P. and Doi, K. (1982) "Investigation of the Performance of Antiscatter Grids: Monte Carlo Simulation Studies," *Phys. Med. Biol.* 27(6), 785-803.
92. Chan, H. P. et al. (1985) "Performance of Antiscatter Grids in Diagnostic Radiology: Experimental Measurements and Monte Carlo Simulation Studies," *Med. Phys.* 12(4), 449-454.
93. Persliden, J. and Carlsson, G. A. (1997) "Scatter Rejection by Air Gaps in Diagnostic Radiology. Calculations Using a Monte Carlo Collision Density Method and Consideration of Molecular Interference in Coherent Scattering," *Phys. Med. Biol.* 42(1), 155-175.
94. Bootsma, G. J. et al. (2011) "The Effects of Compensator and Imaging Geometry on the Distribution of X-Ray Scatter in Cbct," *Med. Phys.* 38(2), 897-914.
95. Wiegert, J. and Bertram, M. (2006) "Scattered Radiation in Flat-Detector Based Cone-Beam Ct: Analysis of Voxelized Patient Simulations," pp 614235-614235-614212.
96. Patel, T. et al. (2016) "Design and Evaluation of a Grid Reciprocation Scheme for Use in Digital Breast Tomosynthesis," pp 978805-978805-978819.

97. Lin, C.-Y. et al. (2006) "A Study of Grid Artifacts Formation and Elimination in Computed Radiographic Images," *J. Digit. Imaging* 19(4), 351-361.
98. Sasada, R. et al. (2003) "Stationary Grid Pattern Removal Using 2D Technique for Moire-Free Radiographic Image Display," pp 688-697.
99. Tang, H. et al. (2015) "A New Stationary Gridline Artifact Suppression Method Based on the 2D Discrete Wavelet Transform," *Med. Phys.* 42(4), 1721-1729.
100. Sun, X.-D. "X-Ray Detectors with a Grid Structured Scintillators," United States Patent Application Publication Number US 2004-0251420 A1, application Ser. No. 10/866,408, filed Jun. 12, 2004. (published Dec. 16, 2004).
101. Tang, C.-M. "Two-Dimensional, Anti-Scatter Grid and Collimator Designs, and Its Motion, Fabrication and Assembly," U.S. Pat. No. 6,252,938, application Ser. No. 09/459,597, filed Dec. 13, 1999. (issued Jun. 26, 2001).
102. Altunbas, C. et al. (2017) "Transmission Characteristics of a Two Dimensional Antiscatter Grid Prototype for Cbct," *Med. Phys.* 44(8), 3952-3964.

What is claimed is:

1. A method of operating an x-ray imaging system, the method comprising:
   arranging an x-ray source and a detector having an antiscatter grid (ASG) in a centered geometry wherein through-holes of the ASG are aligned with x-rays emission paths of the x-ray source;
   positioning an object between the detector and the x-ray source;
   imaging the object in a first field of view (FOV) with the detector and the x-ray source arranged in the centered geometry;
   arranging the x-ray source and the detector in an offset geometry wherein the through-holes of the ASG are at least partially unaligned with the x-rays emission paths of the x-ray source; and
   moving the detector in the offset geometry to realign the through-holes of the ASG with the x-ray emission paths of the x-ray source.

2. The method of claim 1 further comprising imaging the object in at least a second FOV with the detector and the x-ray source arranged in the offset geometry.

3. The method of claim 1, wherein the detector is a flat panel detector.

4. The method of claim 1, wherein arranging the x-ray source and the detector in the offset geometry comprises shifting the detector laterally by a first distance x.

5. The method of claim 4, wherein the moving step comprises tilting the detector upward toward the x-ray source by an angle ($\theta$).

6. The method of claim 5, wherein the angle ($\theta$) is defined as:

$$\theta = \arcsin\frac{x}{SDD}$$

7. The method of claim 5, wherein the moving step further comprises upwardly shifting, by the tilting step, a center of the detector by a second distance (y).

8. The method of claim 7, wherein the second distance (y) is defined as:

$$y = SDD - \sqrt{SDD^2 - x^2}.$$

* * * * *